(12) United States Patent
Funane

(10) Patent No.: US 11,639,362 B2
(45) Date of Patent: May 2, 2023

(54) TETRADENTATE DIAMINODIPHOSPHINE LIGAND AND TRANSITION METAL COMPLEX, AND METHOD FOR MANUFACTURING SAME AND APPLICATION FOR SAME

(71) Applicant: Takasago International Corporation, Tokyo (JP)

(72) Inventor: Shigeru Funane, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 17/272,811

(22) PCT Filed: Sep. 3, 2019

(86) PCT No.: PCT/JP2019/034621
§ 371 (c)(1),
(2) Date: Mar. 2, 2021

(87) PCT Pub. No.: WO2020/050271
PCT Pub. Date: Mar. 12, 2020

(65) Prior Publication Data
US 2022/0081454 A1    Mar. 17, 2022

(30) Foreign Application Priority Data
Sep. 4, 2018    (JP) .............................. JP2018-165166

(51) Int. Cl.
C07F 9/00        (2006.01)
C07F 9/50        (2006.01)
B01J 31/24       (2006.01)

(52) U.S. Cl.
CPC ............ *C07F 9/5022* (2013.01); *B01J 31/24* (2013.01); *C07F 9/5013* (2013.01);
(Continued)

(58) Field of Classification Search
None
See application file for complete search history.

(56) References Cited

U.S. PATENT DOCUMENTS

| 2003/0018070 A1 | 1/2003 | Yonetani et al. |
| 2011/0237814 A1 | 9/2011 | Kuriyama et al. |

(Continued)

FOREIGN PATENT DOCUMENTS

| WO | WO-98/52551 A1 | 11/1998 |
| WO | WO-2011/048727 A1 | 4/2011 |

(Continued)

OTHER PUBLICATIONS

Ward et al. Angew. Chem. Int. Ed., 47, 70-705 (Year: 2008).*
(Continued)

*Primary Examiner* — Yun Qian
(74) *Attorney, Agent, or Firm* — Foley & Lardner LLP

(57) ABSTRACT

The present invention relates to a transition metal complex having a PNNP4 ligand, which is easy to manufacture and handle and is relatively inexpensively available, and a method for manufacturing the same, as well as a method using this transition metal complex as a catalyst for hydrogenation reduction of ketones, esters and amides to manufacture corresponding alcohols, aldehydes, hemiacetals and hemiaminals, a method using this transition metal complex as a catalyst for oxidation of alcohols, hemiacetals and hemiaminals to manufacture corresponding carbonyl compounds, and a method using this transition metal complex as a catalyst for dehydrogenation condensation between alcohols and amines to manufacture alkylamines.

14 Claims, 4 Drawing Sheets

(52) U.S. Cl.
CPC ..... *C07F 9/5018* (2013.01); *B01J 2531/0255* (2013.01); *B01J 2531/821* (2013.01)

(56) References Cited

U.S. PATENT DOCUMENTS

| | | |
|---|---|---|
| 2014/0288641 A1 | 9/2014 | Levy et al. |
| 2017/0044196 A1 | 2/2017 | Ogata et al. |
| 2017/0088571 A1 | 3/2017 | Dub et al. |

FOREIGN PATENT DOCUMENTS

| | | |
|---|---|---|
| WO | WO-2012/039098 A1 | 3/2012 |
| WO | WO-2012/144650 A1 | 10/2012 |
| WO | WO-2015/163440 A1 | 10/2015 |
| WO | WO-2015/191505 A1 | 12/2015 |

OTHER PUBLICATIONS

Ambundo et al., "Kinetics and Mechanism of Copper(II) Complex formation with Tripodal Aminopolythiaether and Aminopolypyridyl Ligands in Aqueous Solution," Inorg. Chem., 2000, 39(6):1171-1179.

Castillo et al., "Synthesis, spectroscopic, and structural characterization of mixed thioether-benzimidazole copper complexes," Polyhedron, 2015, 85:824-829.

Corbin et al., "Preparation and Properties of Tripodal and Linear Tetradentate N,S-Donor Ligands and their Complexes Containing the $MoO_2^{2}$ Core," Inorganic Chimica Acta, 1984, 90(1):41-51.

Konrad et al., "Dinucleating Hybrid Ligands Providing a 'Soft' PnN and an Adjacent N-Rich Coordination Pocket—Controlled Synthesis of Unsymmetric Homodinuclear and Heterodinuclear Complexes," Eur. J. Inorg. Chem., 2001, 9:2233-2240.

Liebeling et al., "Hysteretic Magnetic Bistability Based on a Molecular Azide Switch," Angewandte Chemie, International Edition, 2005, 44(43):7111-7114.

Xu et al., "Naphthalimide as Highly Selective Fluorescent Sensor for Ag Ions," Chinese Journal of Chemistry, 2007, 25(6):778-783.

Kuriyama et al., "Catalytic Hydrogenation of Esters. Development of an Efficient Catalyst and Processes for Synthesising (R)-1,2-Propanediol and 2(1-Menthoxy)ethanol," Organic Process Research & Development, Dec. 22, 2011, 16(1):166-171.

Ogata et al., "N-Monomethylation of Aromatic Amines with Methanol via PNHP-Pincer Ru Catalysts," Organic Letters, Jul. 6, 2018, 20(13):3866-3870.

* cited by examiner

TETRADENTATE DIAMINODIPHOSPHINE LIGAND AND TRANSITION METAL COMPLEX, AND METHOD FOR MANUFACTURING SAME AND APPLICATION FOR SAME

CROSS-REFERENCE TO RELATED APPLICATIONS

This application is the U.S. National Stage of PCT/JP2019/034621, filed Sep. 3, 2019, which claims priority to JP 2018-165166, filed Sep. 4, 2018.

TECHNICAL FIELD

The present invention relates to a novel tetradentate diaminodiphosphine ligand and a method for manufacturing the same, a transition metal complex having this ligand and a method for manufacturing the same, as well as a method using this complex as a catalyst for hydrogenation reduction of ketones, esters and amides to manufacture alcohols, aldehydes, hemiacetals and hemiaminals, a method using this complex as a catalyst for oxidation of alcohols, hemiacetals and hemiaminals to manufacture carbonyl compounds, and a method using this complex as a catalyst for dehydrogenation condensation between alcohols and amines to manufacture alkylamines.

BACKGROUND ART

Techniques for hydrogenation reduction of ketones, esters and amides to obtain alcohols are industrially important reactions. In particular, reduction by catalytic hydrogenation is useful as a method for manufacturing alcohols, in terms of fewer by-products, good operability, working safety, etc. Moreover, optically active alcohols are important as physiologically active substances (e.g., medicaments, agrochemicals, perfumes) and as intermediates for their synthesis, and asymmetric hydrogenation of ketones or hydrogenation reduction of optically active esters is useful as a method for manufacturing optically active alcohols.

Moreover, techniques for oxidation of alcohols to obtain carbonyl compounds are also industrially important. Peroxides commonly used as oxidizing agents are explosive and are therefore accompanied by danger on an industrial scale. However, techniques using a transition metal as a catalyst require no peroxide and are therefore advantageous in terms of safety.

Catalysts for reduction include heterogeneous catalysts in which platinum, chromium or the like is used as a metal, and homogeneous catalysts in which ruthenium, iridium, rhodium or the like is used as a metal. Reactions using heterogeneous catalysts usually require high temperature and high pressure, and therefore have a problem in terms of safety, so that homogeneous catalysts are industrially advantageous. In particular, complexes containing ruthenium as a metal are more advantageous than complexes containing iridium or rhodium as a metal, in terms of costs.

As a reduction catalyst for carbonyl groups such as ketones or esters, there has been reported a ruthenium complex which has a tridentate aminodiphosphine ligand consisting of two phosphino groups and an imino group, and has carbon monoxide or a tertiary phosphine as an additional ligand (Patent Literature 1). Moreover, there have been reported hydrogenation reaction of amides and oxidation reaction of alcohols, each using a ruthenium complex which has a tridentate aminodiphosphine ligand having two phosphino groups and an imino group, and has carbon monoxide as an additional ligand (Patent Literatures 2 and 3).

CITATION LIST

Patent Literatures

Patent Literature 1: WO2011/048727
Patent Literature 2: WO2012/039098
Patent Literature 3: WO2012/144650

SUMMARY OF INVENTION

Technical Problem

The present invention aims to provide a transition metal complex which is easy to manufacture and handle and is relatively inexpensively available, and a method for manufacturing the same, and further aims to provide a method using this transition metal complex as a catalyst for hydrogenation reduction of ketones, esters and amides to manufacture corresponding alcohols, aldehydes, hemiacetals and hemiaminals, a method using this transition metal complex as a catalyst for oxidation of alcohols to manufacture corresponding carbonyl compounds, and a method using this transition metal complex as a catalyst for dehydrogenation condensation between alcohols and amines to manufacture alkylamines. In terms of costs and residual metal problems, a complex showing higher catalytic activity is required in these reactions for industrial use.

Solution to Problem

As a result of extensive and intensive efforts made under the circumstances stated above, the inventors of the present invention have found a transition metal complex characterized by having a novel PNNP tetradentate ligand of simple structure. The ligand and complex can be easily handled.

Moreover, the inventors of the present invention have found that the transition metal complex found in the present invention shows high catalytic activity in hydrogenation reduction reaction of ketones, esters and amides, oxidation reaction of alcohols, and alkylation reaction of amines using alcohols as carbon sources. These findings led to the completion of the present invention.

The present invention relates to [1] to [21] shown below.
[1] A compound represented by general formula (1) or a Bronsted acid salt thereof:

[Formula 1]

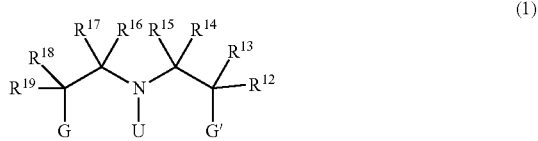

(1)

wherein $R^{12}$, $R^{13}$, $R^{14}$, $R^{15}$, $R^{16}$, $R^{17}$, $R^{18}$ and $R^{19}$ each independently represent a hydrogen atom, an optionally substituted alkyl group, an optionally substituted cycloalkyl group, an optionally substituted aryl group, or an optionally substituted aralkyl group, U represents a group represented by the following general formula ($2^A$) or ($2^B$):

[Formula 2]

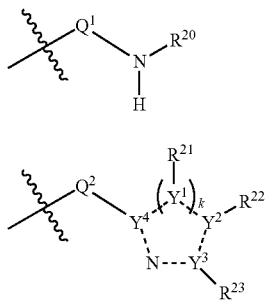

($2^A$)

($2^B$)

wherein the dotted lines each independently represent a single bond or a double bond, and the solid line intersected with the wavy line represents a binding hand to the adjacent atom, $Q^1$ and $Q^2$ each independently represent an optionally substituted alkylene group, an optionally substituted aralkylene group or an optionally substituted arylene group, $R^{20}$ represents a hydrogen atom, an alkyl group, a cycloalkyl group, an optionally substituted alkenyl group, an optionally substituted alkynyl group, an optionally substituted aryl group, an optionally substituted heteroaryl group, or an optionally substituted aralkyl group, $Y^1$, $Y^2$, $Y^3$ and $Y^4$ each independently represent a carbon atom, a nitrogen atom, an oxygen atom or a sulfur atom, provided that at least two of $Y^1$, $Y^2$, $Y^3$ and $Y^4$ are carbon atoms, $R^{21}$, $R^{22}$ and $R^{23}$ each independently represent a hydrogen atom, an alkyl group, a cycloalkyl group, an optionally substituted alkenyl group, an optionally substituted alkynyl group, an optionally substituted aryl group, an optionally substituted aryloxy group, an optionally substituted heteroaryl group, an optionally substituted aralkyl group, an optionally substituted alkoxy group, an optionally substituted aryloxy group, an optionally substituted aralkyloxy group, an optionally substituted amino group or a halogeno group, or $R^{21}$ and $R^{22}$, or $R^{22}$ and $R^{23}$ may be joined together to form an optionally substituted aromatic ring or an optionally substituted heteroaromatic ring, and k is 1 or 2, G and G' each independently represent a hydrogen atom, or at least one of G and G' represents a group represented by the following general formula ($G^P$):

[Formula 3]

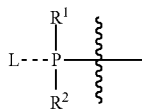

($G^P$)

wherein the dotted line represents a coordinate bond, and the solid line intersected with the wavy line represents a binding hand to the adjacent atom, L represents a lone electron pair or $BH_3$, and $R^1$ and $R^2$ each independently represent an optionally substituted alkyl group, an optionally substituted cycloalkyl group, an optionally substituted alkenyl group, an optionally substituted alkynyl group, an optionally substituted aryl group, an optionally substituted aryloxy group, an optionally substituted heteroaryl group, an optionally substituted aralkyl group, an optionally substituted alkoxy group, an optionally substituted aryloxy group, an optionally substituted aralkyloxy group or an optionally substituted amino group, or $R^1$ and $R^2$ may be joined together to form an optionally substituted ring together with their adjacent phosphorus atom, or a group represented by the following general formula ($G^S$):

[Formula 4]

($G^S$)

wherein the solid line intersected with the wavy line represents a binding hand to the adjacent atom, and $R^3$ represents an optionally substituted alkyl group, an optionally substituted cycloalkyl group, an optionally substituted alkenyl group, an optionally substituted alkynyl group, an optionally substituted aryl group, an optionally substituted heteroaryl group, or an optionally substituted aralkyl group, or a group represented by the following general formula ($G^{C-1}$) or ($G^{C-2}$):

[Formula 5]

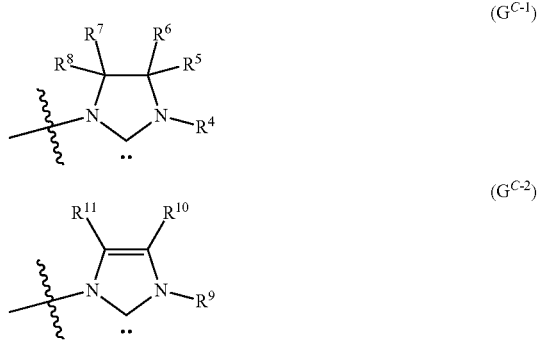

($G^{C-1}$)

($G^{C-2}$)

wherein the double line represents a double bond, and the solid line intersected with the wavy line represents a binding hand to the adjacent atom, $R^4$ and $R^9$ each independently represent an optionally substituted alkyl group, an optionally substituted cycloalkyl group, an optionally substituted alkenyl group, an optionally substituted aryl group, an optionally substituted heteroaryl group, or an optionally substituted aralkyl group, and $R^5$, $R^6$, $R^7$, $R^8$, $R^{10}$ and $R^{11}$ each independently represent a hydrogen atom, an alkyl group, a cycloalkyl group, an optionally substituted alkenyl group, an optionally substituted aryl group, an optionally substituted heteroaryl group, an optionally substituted aralkyl group, an optionally substituted alkoxy group, an optionally substituted aryloxy group, an optionally substituted aralkyloxy group, or an optionally substituted amino group.

[2] The compound or Bronsted acid salt thereof according to [1] above, wherein in general formula (1), $R^{12}$, $R^{13}$, $R^{14}$, $R^{15}$, $R^{16}$, $R^{17}$, $R^{18}$ and $R^{19}$ are all hydrogen atoms.

[3] The compound or Bronsted acid salt thereof according to [2] above, wherein $Q^1$ is an ethylene group and $R^{20}$ is a hydrogen atom.

[4] The compound or Bronsted acid salt thereof according to [2] above, wherein $Q^2$ is a methylene group, $Y^1$, $Y^2$, $Y^3$ and $Y^4$ are all carbon atoms, $R^{21}$, $R^{22}$ and $R^{23}$ are all hydrogen atoms, and k is 2.

[5] The compound or Bronsted acid salt thereof according to [3] or [4] above, wherein G is $G^P$.

[6] The compound or Bronsted acid salt thereof according to [5] above, wherein L in $G^P$ is a lone electron pair.

[7] The compound or Bronsted acid salt thereof according to [6] above, wherein $R^1$ and $R^2$ are each independently an optionally substituted alkyl group, an optionally substituted cycloalkyl group, or an optionally substituted aryl group.

[8] The compound or Bronsted acid salt thereof according to [7] above, wherein $R^1$ and $R^2$ are phenyl groups.

[9] A transition metal complex having the compound or Bronsted acid salt thereof according to any one of [1] to [8] above as a ligand.

[10] The transition metal complex according to [9] above, wherein the metal species is one or more selected from the group consisting of manganese, a transition metal of Group 8, a transition metal of Group 9 and a transition metal of Group 10.

[11] The transition metal complex according to [10] above, which is represented by general formula (8):

$$[M^8X^1X^2(L^1)_k(L^2)_l(L^3)]_n \quad (8)$$

wherein $M^8$ represents Fe, Ru or Os, $X^1$ and $X^2$ each independently represent a monovalent anionic monodentate ligand, $L^1$ and $L^2$ each independently represent a neutral monodentate ligand, k and l represent the coordination numbers of $L^1$ and $L^2$, respectively, and each independently represent 0 or 1, $L^3$ represents the compound or Bronsted acid salt thereof according to any one of [1] to [8] above, and n represents 1 or 2, provided that n represents 1 when the sum total of k and l is an integer of 1 to 2 or n represents 1 or 2 when this sum total is 0.

[12] The transition metal complex according to [10] above, which is represented by the following general formula (9):

$$M^9X^1X^2X^3(L^1)_k(L^2)_l(L^3) \quad (9)$$

wherein $M^9$ represents Co, Rh or Ir, $X^1$, $X^2$ and $X^3$ each independently represent a monovalent anionic monodentate ligand, $L^1$ and $L^2$ each independently represent a neutral monodentate ligand, k and l represent the coordination numbers of $L^1$ and $L^2$, respectively, and each independently represent 0 or 1, and $L^3$ represents the compound or Bronsted acid salt thereof according to any one of [1] to [8] above.

[13] The transition metal complex according to [10] above, which is represented by the following general formula (10):

$$M^{10}X^1X^2(L^3) \quad (10)$$

wherein $M^{10}$ represents Ni, Pd or Pt, $X^1$ and $X^2$ each independently represent a monovalent anionic monodentate ligand, and $L^3$ represents the compound or Bronsted acid salt thereof according to any one of [1] to [8] above.

[14] The transition metal complex according to [10] above, which is represented by the following general formula (11):

$$MnX(L^1)_k(L^2)_l(L^3) \quad (11)$$

wherein X represents a monovalent anionic monodentate ligand, $L^1$ and $L^2$ each independently represent a neutral monodentate ligand, k and l represent the coordination numbers of $L^1$ and $L^2$, respectively, and each independently represent 0 or 1, and $L^3$ represents the compound or Bronsted acid salt thereof according to any one of [1] to [8] above.

[15] The transition metal complex according to [11] above, wherein $M^8$ is Ru.

[16] The transition metal complex according to [15] above, wherein $L^1$ is CO, k is 1, l is 0, and n is 1.

[17] A method for manufacturing alcohols, aldehydes or hemiacetals, the method comprising hydrogenation reduction of esters in the presence of the transition metal complex according to any one of [9] to [16] above.

[18] A method for manufacturing alcohols, aldehydes, hemiaminals or amines, the method comprising hydrogenation reduction of amides in the presence of the transition metal complex according to any one of [9] to [16] above.

[19] A method for manufacturing alcohols, the method comprising hydrogenation reduction of ketones in the presence of the transition metal complex according to any one of [9] to [16] above.

[20] A method for manufacturing carbonyl compounds, the method comprising dehydrogenation of alcohols, hemiacetals or hemiaminals in the presence of the transition metal complex according to any one of [9] to [16] above.

[21] A method for manufacturing alkylamines, the method comprising dehydration condensation between alcohols and amines in the presence of the transition metal complex according to any one of [9] to [16] above.

Moreover, the present invention relates to [1] to [19] shown below.

[1] A compound characterized by being represented by general formula (1).

[Formula 6]

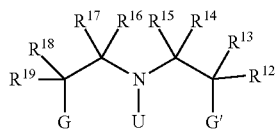

(1)

$R^{12}$, $R^{13}$, $R^{14}$, $R^{15}$, $R^{16}$, $R^{17}$, $R^{18}$ and $R^{19}$ each independently represent a hydrogen atom, an alkyl group, a cycloalkyl group, an aryl group and an aralkyl group.

U represents a group represented by the following general formula ($2^A$) or ($2^B$)

[Formula 7]

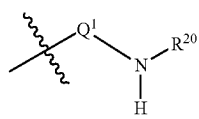

($2^A$)

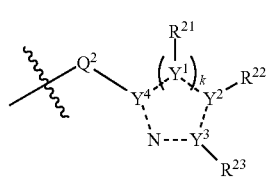

($2^B$)

wherein the dotted lines each independently represent a single bond or a double bond, and the solid line intersected with the wavy line represents a binding hand to the adjacent atom.

$Q^1$ and $Q^2$ each independently represent an optionally substituted alkylene group, an optionally substituted aralkylene group, or an optionally substituted arylene group.

$R^{20}$ represents a hydrogen atom, an alkyl group, a cycloalkyl group, an optionally substituted alkenyl group, an optionally substituted alkynyl group, an optionally substituted aryl group, an optionally substituted heteroaryl group and an optionally substituted aralkyl group.

$Y^1$ to $Y^4$ each independently represent a carbon atom, a nitrogen atom, an oxygen atom and a sulfur atom, provided that at least two of $Y^1$ to $Y^4$ are carbon atoms.

$R^{21}$ to $R^{23}$ each independently represent a hydrogen atom, an alkyl group, a cycloalkyl group, an optionally substituted alkenyl group, an optionally substituted alkynyl group, an optionally substituted aryl group, an optionally substituted aryloxy group, an optionally substituted heteroaryl group, an optionally substituted aralkyl group, an optionally substituted alkoxy group, an optionally substituted aryloxy group, an optionally substituted aralkyloxy group, an optionally substituted amino group and a halogeno group. $R^{21}$ and $R^{22}$, or $R^{22}$ and $R^{23}$ may be joined together to form an optionally substituted aromatic ring and an optionally substituted heteroaromatic ring.

k is 1 or 2.

G represents a group represented by the following general formula ($G^P$)

[Formula 8]

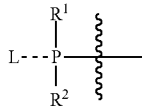

(G^P)

wherein the dotted line represents a coordinate bond, and the solid line intersected with the wavy line represents a binding hand to the adjacent atom.

L represents a lone electron pair or $BH_3$.

$R^1$ and $R^2$ each independently represent an alkyl group, a cycloalkyl group, an optionally substituted alkenyl group, an optionally substituted alkynyl group, an optionally substituted aryl group, an optionally substituted aryloxy group, an optionally substituted heteroaryl group, an optionally substituted aralkyl group, an optionally substituted alkoxy group, an optionally substituted aryloxy group, an optionally substituted aralkyloxy group and an optionally substituted amino group. $R^1$ and $R^2$ may be joined together to form an optionally substituted ring together with their adjacent phosphorus atom
and a group represented by the following general formula ($G^S$)

[Formula 9]

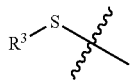

($G^S$)

wherein the solid line intersected with the wavy line represents a binding hand to the adjacent atom.

$R^3$ represents an alkyl group, a cycloalkyl group, an optionally substituted alkenyl group, an optionally substituted alkynyl group, an optionally substituted aryl group, an optionally substituted heteroaryl group, and an optionally substituted aralkyl group and groups represented by the following general formulae ($G^{C-1}$) and ($G^{C-2}$)

[Formula 10]

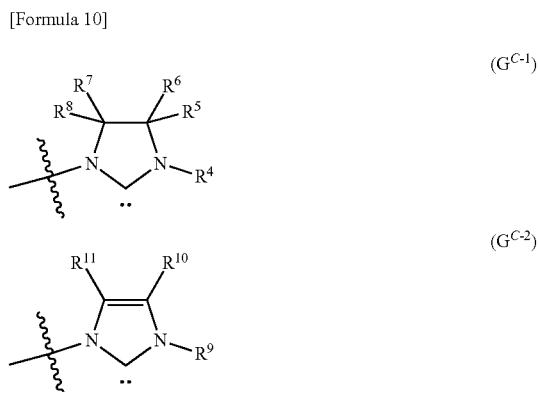

wherein the double line represents a double bond, and the solid line intersected with the wavy line represents a binding hand to the adjacent atom.

$R^4$ and $R^9$ each independently represent an alkyl group, a cycloalkyl group, an optionally substituted alkenyl group, an optionally substituted aryl group, an optionally substituted heteroaryl group and an optionally substituted aralkyl group. $R^5$, $R^6$, $R^7$, $R^8$, $R^{10}$ and $R^{11}$ each independently represent a hydrogen atom, an alkyl group, a cycloalkyl group, an optionally substituted alkenyl group, an optionally substituted aryl group, an optionally substituted heteroaryl group, an optionally substituted aralkyl group, an optionally substituted alkoxy group, an optionally substituted aryloxy group, an optionally substituted aralkyloxy group and an optionally substituted amino group.

[2] The compound according to [1] above, wherein in general formula (1), $R^{12}$ to $R^{19}$ are all hydrogen atoms.

[3] The compound according to [2] above, wherein $Q^1$ is an ethylene group and $R^{20}$ is a hydrogen atom.

[4] The compound according to [2] above, wherein $Q^2$ is a methylene group, $Y^1$ to $Y^4$ are all carbon atoms, $R^{21}$ to $R^{23}$ are all hydrogen atoms, and k is 2.

[5] The compound according to any one of [3] or [4] above, wherein G is $G^P$.

[6] The compound according to [5] above, characterized in that $G^P$ is $PR^1R^2$.

[7] The compound according to [6] above, characterized in that $R^1$ and $R^2$ are each independently an alkyl group, a cycloalkyl group or an optionally substituted aryl group.

[8] The compound according to [7] above, wherein $R^1$ and $R^2$ are phenyl groups.

[9] A metal complex having the compound according to any one of [1] to [8] above as a ligand.

[10] The metal complex according to [9] above, characterized in that the metal species comprises a transition metal of Group 8, a transition metal of Group 9 and a transition metal of Group 10.

[11] The metal complex according to [10] above, characterized by being represented by general formula (8):

$$[M^8X^1X^2(L^1)_k(L^2)_l(L^3)]_n \quad (8)$$

wherein $M^8$ represents Fe, Ru and Os. $X^1$ and $X^2$ each independently represent a monovalent anionic monodentate ligand, and $L^1$ and $L^2$ each independently represent a neutral monodentate ligand. k and l represent the coordination numbers of $L^1$ and $L^2$, respectively, and each independently represent 0 or 1. $L^3$ represents the compound according to any one of [1] to [8] above. n represents 1 or 2, provided that n represents 1 when the sum total of k and l is 1 to 2 or n represents 1 or 2 when the sum total is 0.

[12] The metal complex according to [10] above, characterized by being represented by the following general formula (9):

$$M^9X^1X^2X^3(L^1)_k(L^2)_l(L^3) \quad (9)$$

wherein $M^9$ represents Co, Rh and Ir. $X^1$, $X^2$ and $X^3$ each independently represent a monovalent anionic monodentate ligand, and $L^1$ and $L^2$ each independently represent a neutral monodentate ligand. k and l represent the coordination numbers of $L^1$ and $L^2$, respectively, and each independently represent 0 or 1. $L^3$ represents the compound according to any one of [1] to [8] above.

[13] The metal complex according to [10] above, characterized by being represented by the following general formula (10):

$$M^{10}X^1X^2(L^3) \quad (10)$$

wherein $M^{10}$ represents Ni, Pd and Pt. $X^1$ and $X^2$ each independently represent a monovalent anionic monodentate ligand. $L^3$ represents the compound according to any one of [1] to [8] above.

[14] The metal complex according to [11] above, characterized in that $M^8$ is Ru.

[15] The metal complex according to [14] above, characterized in that $L^1$ is CO, k is 1, l is 0 and n is 1.

[16] A method for manufacturing alcohols, aldehydes or hemiacetals, characterized by hydrogenation reduction of esters in the presence of the metal complex according to any one of [9] to [15] above.

[17] A method for manufacturing alcohols, aldehydes, hemiaminals or amines, characterized by hydrogenation reduction of amides in the presence of the metal complex according to any one of [9] to [15] above.

[18] A method for manufacturing carbonyl compounds, characterized by dehydrogenation of alcohols, hemiacetals or hemiaminals in the presence of the metal complex according to any one of [9] to [15] above.

[19] A method for manufacturing alkylamines, characterized by dehydration condensation between alcohols and amines in the presence of the metal complex according to any one of [9] to [15] above.

Advantageous Effects of Invention

According to a preferred embodiment of the present invention, the novel compound of the present invention represented by general formula (1) functions as a tetradentate ligand and may be reacted with various transition metal compounds to thereby synthesize transition metal complexes showing advantageous catalytic activity in various organic synthesis reactions.

For example, the novel ruthenium complex of the present invention can be easily prepared from a tetradentate diaminodiphosphine represented by PNNP and a ruthenium compound, and is suitable for industrial use. According to a preferred embodiment of the present invention, the ruthenium complex of the present invention has high catalytic activity and is capable of catalyzing, e.g., hydrogenation reduction of ketones, esters and amides in the presence of a hydrogen donor to manufacture alcohols, aldehydes, hemiacetals and hemiaminals in high yields. Moreover, the ruthenium complex of the present invention is also capable of catalyzing oxidation reaction of alcohols, hemiacetals and hemiaminals or alkylation reaction of amines using alcohols as carbon sources.

DESCRIPTION OF EMBODIMENTS

[The Compound of the Present Invention]

Figure 1:
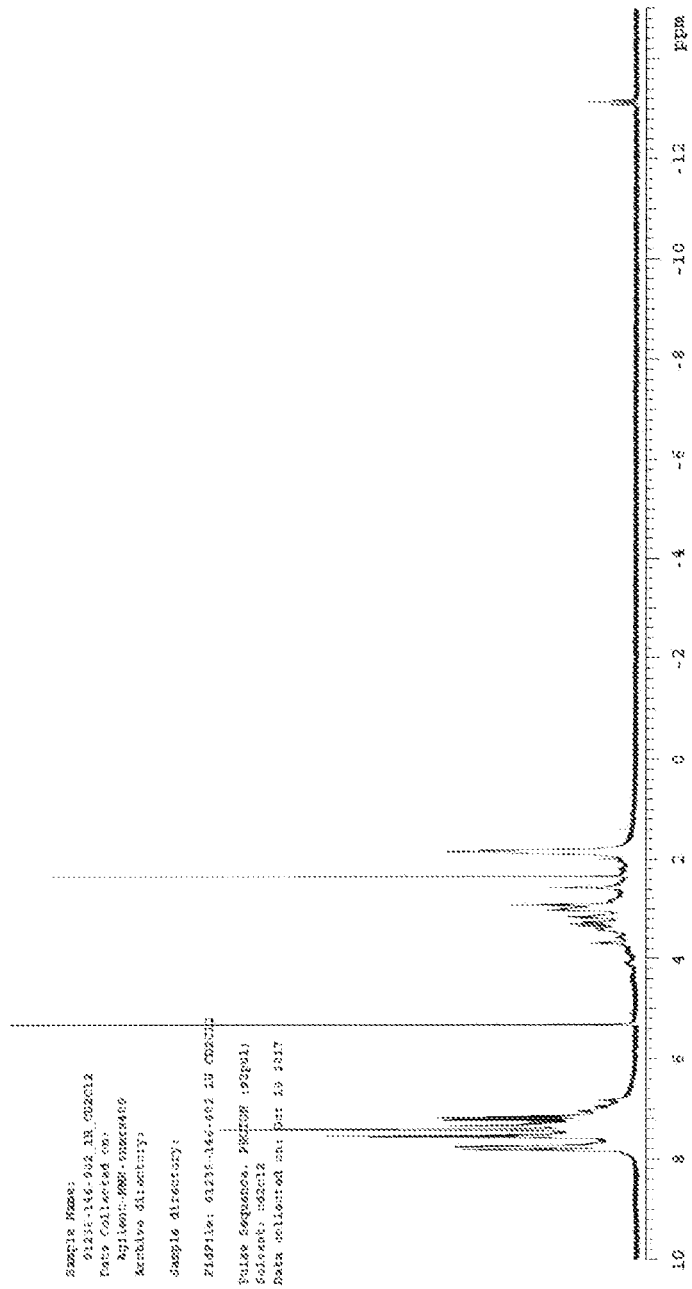
FIG. 1 shows a $^1$H-NMR spectrum of complex $8^Y$-1 obtained in Example 8.

The compound of the present invention represented by general formula (1) (herein also referred to as "the compound of the present invention" or "the compound (1) of the present invention") will be described below.

The compound of the present invention is characterized by being represented by general formula (1):

[Formula 11]

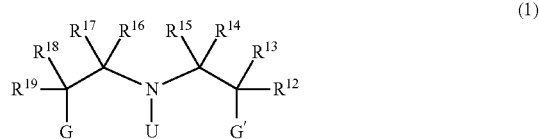

(1)

wherein $R^{12}$, $R^{13}$, $R^{14}$, $R^{15}$, $R^{16}$, $R^{17}$, $R^{18}$ and $R^{19}$ each independently represent a hydrogen atom, an optionally substituted alkyl group, an optionally substituted cycloalkyl group, an optionally substituted aryl group, or an optionally substituted aralkyl group, U represents a group represented by the following general formula ($2^A$) or ($2^B$):

[Formula 12]

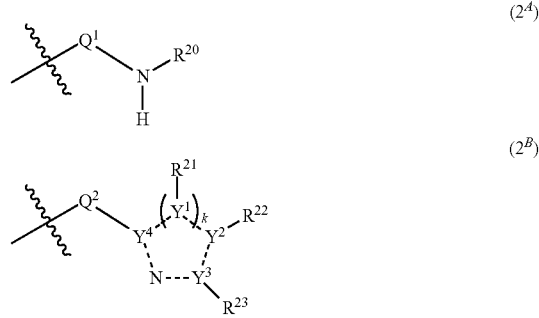

wherein the dotted lines each independently represent a single bond or a double bond, and the solid line intersected with the wavy line represents a binding hand to the adjacent atom, $Q^1$ and $Q^2$ each independently represent an optionally substituted alkylene group, an optionally substituted aralkylene group or an optionally substituted arylene group, $R^{20}$ represents a hydrogen atom, an alkyl group, a cycloalkyl group, an optionally substituted alkenyl group, an optionally substituted alkynyl group, an optionally substituted aryl group, an optionally substituted heteroaryl group, or an optionally substituted aralkyl group, $Y^1$, $Y^2$, $Y^3$ and $Y^4$ each independently represent a carbon atom, a nitrogen atom, an oxygen atom or a sulfur atom, provided that at least two of $Y^1$, $Y^2$, $Y^3$ and $Y^4$ are carbon atoms, $R^{21}$, $R^{22}$ and $R^{23}$ each independently represent a hydrogen atom, an alkyl group, a cycloalkyl group, an optionally substituted alkenyl group, an optionally substituted alkynyl group, an optionally substituted aryl group, an optionally substituted aryloxy group, an optionally substituted heteroaryl group, an optionally substituted aralkyl group, an optionally substituted alkoxy group, an optionally substituted aryloxy group, an optionally substituted aralkyloxy group, an optionally substituted amino group or a halogeno group, or $R^{21}$ and $R^{22}$, or $R^{22}$ and $R^{23}$ may be joined together to form an optionally substituted aromatic ring or an optionally substituted heteroaromatic ring, and k is 1 or 2, G and G' each independently represent a hydrogen atom, or at least one of G and G' represents a group represented by the following general formula ($G^P$):

[Formula 13]

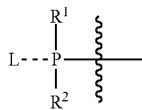

($G^P$)

wherein the dotted line represents a coordinate bond, and the solid line intersected with the wavy line represents a binding hand to the adjacent atom, L represents a lone electron pair or $BH_3$, and $R^1$ and $R^2$ each independently represent an optionally substituted alkyl group, an optionally substituted cycloalkyl group, an optionally substituted alkenyl group, an optionally substituted alkynyl group, an optionally substituted aryl group, an optionally substituted aryloxy group, an optionally substituted heteroaryl group, an optionally substituted aralkyl group, an optionally substituted alkoxy group, an optionally substituted aryloxy group, an optionally substituted aralkyloxy group or an optionally substituted amino group, or $R^1$ and $R^2$ may be joined together to form an optionally substituted ring together with their adjacent phosphorus atom, or a group represented by the following general formula ($G^S$):

[Formula 14]

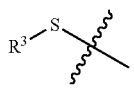

($G^S$)

wherein the solid line intersected with the wavy line represents a binding hand to the adjacent atom, $R^3$ represents an optionally substituted alkyl group, an optionally substituted cycloalkyl group, an optionally substituted alkenyl group, an optionally substituted alkynyl group, an optionally substituted aryl group, an optionally substituted heteroaryl group, or an optionally substituted aralkyl group, or a group represented by the following general formula ($G^{C-1}$) or ($G^{C-2}$):

[Formula 15]

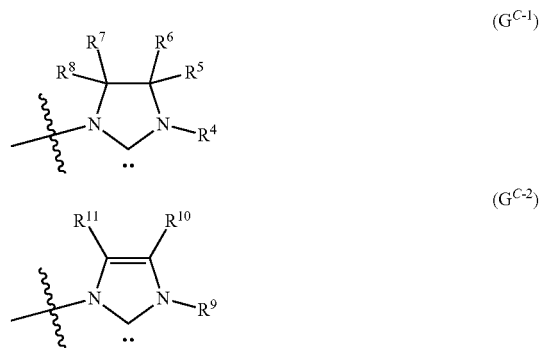

wherein the double line represents a double bond, and the solid line intersected with the wavy line represents a binding hand to the adjacent atom, $R^4$ and $R^9$ each independently represent an optionally substituted alkyl group, an optionally substituted cycloalkyl group, an optionally substituted alkenyl group, an optionally substituted aryl group, an optionally substituted heteroaryl group, or an optionally substituted aralkyl group, and $R^5$, $R^6$, $R^7$, $R^8$, $R^9$, $R^{10}$ and $R^{11}$ each independently represent a hydrogen atom, an alkyl group, a cycloalkyl group, an optionally substituted alkenyl group, an optionally substituted aryl group, an optionally substituted heteroaryl group, an optionally substituted aralkyl group, an optionally substituted alkoxy group, an optionally substituted aryloxy group, an optionally substituted aralkyloxy group, or an optionally substituted amino group.

First, an explanation will be made of $R^{12}$, $R^{13}$, $R^{14}$, $R^{15}$, $R^{16}$, $R^{17}$, $R^{18}$ and $R^{19}$ in general formula (1).

$R^{12}$, $R^{13}$, $R^{14}$, $R^{15}$, $R^{16}$, $R^{17}$, $R^{18}$ and $R^{19}$ are each independently selected from a hydrogen atom, an alkyl group, a cycloalkyl group, an aryl group, or an aralkyl group.

Moreover, these alkyl, cycloalkyl, aryl and aralkyl groups are optionally substituted.

Alkyl groups in $R^{12}$, $R^{13}$, $R^{14}$, $R^{15}$, $R^{16}$, $R^{17}$, $R^{18}$ and $R^{19}$ may be either linear or branched, as exemplified by alkyl groups containing 1 to 50 carbon atoms, preferably 1 to 20 carbon atoms, more preferably 1 to 10 carbon atoms. Examples include a methyl group, an ethyl group, a n-propyl group, a 2-propyl group, a n-butyl group, a 2-butyl group, an isobutyl group, a tert-butyl group, a n-pentyl group, a 2-pentyl group, a 3-pentyl group, a 2-methylbutyl group, a 3-methylbutyl group, a 2-methylbutan-2-yl group, a 2-methylbutan-3-yl group, a 2,2-dimethylpropyl group, a n-hexyl group, a 2-hexyl group, a 3-hexyl group, a 2-methylpentyl group, a 3-methylpentyl group, a 4-methylpentyl group, a 2-methylpentan-2-yl group, a 2-methylpentan-3-yl group, a 2-methylpentan-4-yl group, a 3-methylpentan-2-yl group, a 3-methylpentan-3-yl group, a 2,2-dimethylbutyl group, a 3,3-dimethylbutyl group, a 2,2-dimethylbutan-3-yl group, a n-heptyl group, a n-octyl group, a n-nonyl group and a n-decyl group, with a methyl group being preferred.

Examples of cycloalkyl groups in $R^{12}$, $R^{13}$, $R^{14}$, $R^{15}$, $R^{16}$, $R^{17}$, $R^{18}$ and $R^{19}$ include a cyclopropyl group, a cyclopentyl group, a cyclohexyl group, a cyclooctyl group, a bicyclo[1.1.0]butyl group, a tricyclo[2.2.1.0]heptyl group, a bicyclo[3.2.1]octyl group, a bicyclo[2.2.2]octyl group, an adamantyl group (i.e., a tricyclo[3.3.1.1]decyl group), a bicyclo[4.3.2]undecyl group, a tricyclo[5.3.1.1]dodecyl group and so on.

Examples of aryl groups in $R^{12}$, $R^{13}$, $R^{14}$, $R^{15}$, $R^{16}$, $R^{17}$, $R^{18}$ and $R^{19}$ include monocyclic, polycyclic or fused ring aryl groups containing 6 to 36 carbon atoms, preferably 6 to 18 carbon atoms, more preferably 6 to 14 carbon atoms, as specifically exemplified by a phenyl group, a naphthyl group, an anthryl group, a phenanthryl group, a biphenyl group and so on.

Aralkyl groups in $R^{12}$, $R^{13}$, $R^{14}$, $R^{15}$, $R^{16}$, $R^{17}$, $R^{18}$ and $R^{19}$ may be alkyl groups as discussed above whose at least one hydrogen atom has been replaced with an aryl group as discussed above. Examples include aralkyl groups containing 7 to 37 carbon atoms, preferably 7 to 20 carbon atoms, more preferably 7 to 15 carbon atoms, as specifically exemplified by a benzyl group, a 1-phenylethyl group, a 2-phenylethyl group, a 1-phenylpropyl group, a 3-naphthylpropyl group and so on.

Moreover, substituents which may be substituted on these alkyl, cycloalkyl, aryl and aralkyl groups include an alkyl group as discussed above, an aryl group as discussed above, an aralkyl group as discussed above, an alkenyl group, an alkynyl group, an alkyloxy group, an aryloxy group, an aralkyloxy group, a heteroaryl group, an amino group, a halogeno group, a silyl group, and an optionally protected hydroxyl group, etc.

Such an alkenyl group may be linear, branched or cyclic, as exemplified by alkenyl groups containing 2 to 20 carbon atoms, preferably 2 to 15 carbon atoms, more preferably 2 to 10 carbon atoms. Specific examples include an ethenyl group, a propenyl group, a 1-butenyl group, a pentenyl group, a hexenyl group, a heptenyl group, an octenyl group, a nonenyl group, a decenyl group and so on, as well as a cyclobutenyl group, a cyclopentenyl group, a cyclohexenyl group, a cycloheptenyl group, or a cyclooctenyl group.

Such an alkynyl group may be linear, branched or cyclic, as exemplified by alkynyl groups containing 2 to 20 carbon atoms, preferably 2 to 15 carbon atoms, more preferably 2 to 10 carbon atoms. Specific examples include an ethynyl group, a propynyl group, a 1-butynyl group, a pentynyl group, a hexynyl group, a heptynyl group, an octynyl group, a nonynyl group, a decynyl group and so on, as well as a cyclobutynyl group, a cyclopentynyl group, a cyclohexynyl group, a cycloheptynyl group, or a cyclooctynyl group.

Alkyloxy, aryloxy and aralkyloxy groups may be exemplified by alkyloxy, aryloxy and aralkyloxy groups corresponding to alkyl, aryl and aralkyl groups as discussed above, respectively.

A heteroaryl group may be exemplified by heteroaryl groups derived from a 5- to 6-membered aromatic heterocyclic ring containing 1 to 4 heteroatoms selected from the group consisting of a nitrogen atom, an oxygen atom and a sulfur atom, and heteroaryl groups derived from a polycyclic aromatic heterocyclic ring generated upon annelation of the above aromatic heterocyclic ring with an aryl group as discussed above. Specific examples include a 2-furyl group, a 3-furyl group, a 2-thienyl group, a 3-thienyl group, a 2-benzofuryl group, a 3-benzofuryl group, a 2-benzothienyl group and a 3-benzothienyl group, etc., with a 2-furyl group being preferred.

An amino group may be optionally substituted, and substituents which may be substituted on such an amino group include an alkyl group as discussed above, an aryl group as discussed above, an aralkyl group as discussed above, an alkenyl group as discussed above, an alkynyl group as discussed above, an alkyloxy group as discussed above, an aryloxy group as discussed above, an aralkyloxy group as discussed above, and a heteroaryl group as discussed above.

A halogen atom as a substituent includes a fluorine atom, a chlorine atom, a bromine atom and an iodine atom.

A silyl group as a substituent includes silyl groups whose three hydrogen atoms have been replaced with alkyl groups as discussed above, aryl groups as discussed above, aralkyl groups as discussed above, etc. Specific examples include a trimethylsilyl group, a triethylsilyl group, a t-butyldimethylsilyl group, a t-butyldiphenylsilyl group, a triphenylsilyl group and so on.

An optionally protected hydroxyl group as a substituent includes an unprotected hydroxyl group, or hydroxyl groups which may be protected with protective groups commonly used for hydroxyl groups, as described in a document (Protective Groups in Organic Synthesis Second Edition, JOHN WILEY & SONS, INC. 1991), and such protective groups include tri-substituted silyl groups (e.g., a trimethylsilyl group, a tert-butyldimethylsilyl group, a tert-butyldiphenylsilyl group), a benzyl group and a methoxymethyl group, etc.

An explanation will then be made of $Q^1$ in general formula ($2^4$). $Q^1$ represents a divalent group, as exemplified by an optionally substituted alkylene group, an optionally substituted aralkylene group, and an optionally substituted arylene group.

Such an alkylene group in $Q^1$ may be linear, branched or cyclic, as exemplified by divalent groups consisting of alkylene groups containing 1 to 20 carbon atoms, preferably 1 to 10 carbon atoms, more preferably 1 to 6 carbon atoms. Specific examples include a methylene group, an ethylene group, a trimethylene group, a tetramethylene group, a pentamethylene group, a cyclopropylene group, a cyclobutylene group, a cyclopentylene group, or a cyclohexylene group, etc.

Such an aralkylene group in $Q^1$ may be exemplified by divalent groups containing 7 to 11 carbon atoms configured such that one hydrogen has been removed from an aryl group in an aralkyl group (e.g., a benzyl group, a phenethyl group). Specific examples include a benzylene group (-Ph-CH$_2$—), a 2-phenylethylene group (-Ph-CH$_2$CH$_2$—), a 1-naphthylmethylene group (—Np—CH$_2$—), and a 2-naphthylmethylene group (—Np—CH$_2$—) (wherein -Ph- represents a phenylene group and —Np— represents a naphthylene group), etc.

Such an arylene group in $Q^1$ may be exemplified by divalent groups consisting of monocyclic or fused ring aryl groups containing 6 to 12 carbon atoms. Examples include a phenylene group, a 2,3-naphthalenediyl group and so on. Such a phenylene group includes an o- or m-phenylene group.

Substituents which may be substituted on these alkylene, aralkylene and arylene groups include an alkyl group, an aryl group, an aralkyl group, an alkyloxy group, an aryloxy group, an aralkyloxy group and a heteroaryl group, as well as a halogeno group, a silyl group, an amino group and an optionally protected hydroxyl group, etc., as discussed above for $R^{12}$, $R^{13}$, $R^{14}$, $R^{15}$, $R^{16}$, $R^{17}$, $R^{18}$ and $R^{19}$.

An explanation will be made of $R^{20}$ in general formula ($2^A$). $R^{20}$ is selected from a hydrogen atom, an alkyl group, a cycloalkyl group, an aryl group, an aralkyl group, an alkenyl group, an alkynyl group or a heteroaryl group. These aryl, aralkyl, alkenyl, alkynyl and heteroaryl groups are optionally substituted. These alkyl, cycloalkyl, aryl, aralkyl, alkenyl, alkynyl and heteroaryl groups are selected from an alkyl group, a cycloalkyl group, an aryl group, an aralkyl group, an alkenyl group, an alkynyl group or a heteroaryl group as discussed above for $R^{12}$, $R^{13}$, $R^{14}$, $R^{15}$, $R^{16}$, $R^{17}$, $R^{18}$ and $R^{19}$ in general formula (1). Substituents which may be substituted on these alkyl, cycloalkyl, aryl, aralkyl, alkenyl, alkynyl and heteroaryl groups include an alkyl group, a cycloalkyl group, an aryl group, an aralkyl group, an alkyloxy group, an aryloxy group, an aralkyloxy group and a heteroaryl group, as well as a halogeno group, a silyl group, an amino group and an optionally protected hydroxyl group, etc., as discussed above for $R^{12}$, $R^{13}$, $R^{14}$, $R^{15}$, $R^{16}$, $R^{17}$, $R^{18}$ and $R^{19}$.

An explanation will be made of $Q^2$ in general formula ($2^B$). $Q^2$ represents a divalent group, as exemplified by an optionally substituted alkylene group, an optionally substituted aralkylene group, and an optionally substituted arylene group.

Such alkylene, aralkylene and arylene groups in $Q^2$ may be exemplified by an alkylene group, an aralkylene group and an arylene group as discussed above for $Q^1$.

Substituents which may be substituted on these alkylene, aralkylene and arylene groups include an alkyl group, an aryl group, an aralkyl group, an alkyloxy group, an aryloxy group, an aralkyloxy group and a heteroaryl group, as well as a halogeno group, a silyl group, an amino group and an optionally protected hydroxyl group, etc., as discussed above for $R^{12}$, $R^{13}$, $R^{14}$, $R^{15}$, $R^{16}$, $R^{17}$, $R^{18}$ and $R^{19}$.

An explanation will be made of the structural moiety $(-(Y^1)_k(R^{21})Y^2(R^{22})Y^3(R^{23})NY^4-)$ bonded to $Q^2$ in general formula ($2^B$).

$Y^1$, $Y^2$, $Y^3$ and $Y^4$ each independently represent a carbon atom, a nitrogen atom, an oxygen atom or a sulfur atom, and at least two of $Y^1$, $Y^2$, $Y^3$ and $Y^4$ are carbon atoms.

The structural moiety $(-(Y^1)_k(R^{21})Y^2(R^{22})Y^3(R^{23})NY^4-)$ may be exemplified by an aliphatic heterocyclic group and an aromatic heterocyclic group. Examples of an aliphatic heterocyclic group include a 3- to 8-membered, preferably 4- to 6-membered, monocyclic aliphatic heterocyclic group and a polycyclic or fused ring aliphatic heterocyclic group, each containing 2 to 14 carbon atoms and containing at least one, preferably 1 to 3 heteroatoms such as a nitrogen atom, an oxygen atom and/or a sulfur atom. Specific examples of such an aliphatic heterocyclic group include an azetidyl group, an azetidino group, a pyrrolidyl group, a pyrrolidino group, a piperidinyl group, a piperidino group, a piperazinyl group, a piperazino group, a morpholinyl group, a morpholino group, a tetrahydrofuryl group, a tetrahydropyranyl group, a tetrahydrothiophenyl group and so on. Examples of an aromatic heterocyclic group include a 5- or 6-membered monocyclic heteroaryl group and a polycyclic or fused ring heteroaryl group, each containing 2 to 15 carbon atoms and containing at least one, preferably 1 to 3 heteroatoms such as a nitrogen atom, an oxygen atom and/or a sulfur atom. Specific examples include a furyl group, a thienyl group, a pyridyl group, a pyrimidyl group, a pyrazyl group, a pyridazyl group, a pyrazolyl group, an imidazolyl group, an oxazolyl group, a thiazolyl group, a benzofuryl group, a benzothienyl group, a quinolyl group, an isoquinolyl group, a quinoxalyl group, a phthalazyl group, a quinazolyl group, a naphthyridyl group, a cinnolyl group, a benzoimidazolyl group, a benzoxazolyl group, a benzothiazolyl group, an acridyl group, an acridinyl group and so on. More preferred examples include 5- or 6-membered monocyclic nitrogen-containing heteroaryl groups, as specifically exemplified by a pyridyl group, a pyrimidyl group, a pyrazyl group, a pyridazyl group, a pyrazolyl group, an imidazolyl group, an oxazolyl group, a thiazolyl group and so on.

An explanation will be made of $R^{21}$, $R^{22}$ and $R^{23}$ in general formula ($2^B$). $R^{21}$, $R^{22}$ and $R^{23}$ are each independently selected from a hydrogen atom, an alkyl group, a cycloalkyl group, an aryl group, an aralkyl group, an alkenyl group, an alkynyl group, an alkoxy group, an aryloxy group, an aralkyloxy group, a heteroaryl group, an amino group or a halogeno group. These aryl, aralkyl, alkenyl, alkynyl, alkoxy, aryloxy, aralkyloxy, heteroaryl and amino groups are optionally substituted. These alkyl, cycloalkyl, aryl, aralkyl, alkenyl, alkynyl, alkoxy, aryloxy, aralkyloxy, heteroaryl, amino and halogeno groups are selected from an alkyl group, an aryl group, an aralkyl group, an alkenyl group, an alkynyl group, an alkyloxy group, an aryloxy group, an aralkyloxy group, a heteroaryl group, an amino group and a halogeno group as discussed above for $R^{12}$, $R^{13}$, $R^{14}$, $R^{15}$, $R^{16}$, $R^{17}$, $R^{18}$ and $R^{19}$ in general formula (1). Substituents which may be substituted on these aryl, aralkyl, alkenyl, alkynyl, alkyloxy, aryloxy, aralkyloxy, heteroaryl and amino groups include an alkyl group, an aryl group, an aralkyl group, an alkyloxy group, an aryloxy group, an aralkyloxy group and a heteroaryl group, as well as a halogeno group, a silyl group, an amino group and an optionally protected hydroxyl group, etc., as discussed above for $R^{12}$, $R^{13}$, $R^{14}$, $R^{15}$, $R^{16}$, $R^{17}$, $R^{18}$ and $R^{19}$.

An explanation will be made of $R^1$ and $R^2$ in general formula ($G^P$). $R^1$ and $R^2$ are each independently selected from an alkyl group, a cycloalkyl group, an aryl group, an aralkyl group, an alkenyl group, an alkynyl group, an alkyloxy group, an aryloxy group, an aralkyloxy group, a heteroaryl group, or an amino group. These $R^1$ and $R^2$ may be joined together to form an optionally substituted ring together with their adjacent atom. Moreover, these alkyl, cycloalkyl, aryl, aralkyl, alkenyl, alkynyl, alkyloxy, aryloxy, aralkyloxy, heteroaryl and amino groups are optionally substituted. These alkyl, cycloalkyl, aryl, aralkyl, alkenyl, alkynyl, alkyloxy, aryloxy, aralkyloxy, heteroaryl and amino groups are selected from an alkyl group, a cycloalkyl group, an aryl group, an aralkyl group, an alkenyl group, an alkynyl group, an alkyloxy group, an aryloxy group, an aralkyloxy group, a heteroaryl group and an amino group as discussed above for $R^{12}$, $R^{13}$, $R^{14}$, $R^{15}$, $R^{16}$, $R^{17}$, $R^{18}$ and $R^{19}$ in general formula (1). Substituents which may be substituted on these alkyl, cycloalkyl, aryl, aralkyl, alkenyl, alkynyl, alkyloxy, aryloxy, aralkyloxy, heteroaryl and amino groups include an alkyl group, a cycloalkyl group, an aryl group, an aralkyl group, an alkyloxy group, an aryloxy group, an aralkyloxy group and a heteroaryl group, as well as a halogeno group, a silyl group, an amino group and an optionally protected hydroxyl group, etc., as discussed above for $R^{12}$, $R^{13}$, $R^{14}$, $R^{15}$, $R^{16}$, $R^{17}$, $R^{18}$ and $R^{19}$.

An explanation will be made of $R^3$ in general formula ($G^S$). $R^3$ is selected from an alkyl group, a cycloalkyl group, an aryl group, an aralkyl group, an alkenyl group, an alkynyl group, or a heteroaryl group. Moreover, these alkyl, cycloalkyl, aryl, aralkyl, alkenyl, alkynyl, aralkyloxy and heteroaryl groups are optionally substituted. These alkyl, cycloalkyl, aryl, aralkyl, alkenyl, alkynyl, aralkyloxy and heteroaryl groups are selected from an alkyl group, a cycloalkyl group, an aryl group, an aralkyl group, an alkenyl group, an alkynyl group, an aralkyloxy group and a heteroaryl group as discussed above for $R^{12}$, $R^{13}$, $R^{14}$, $R^{15}$, $R^{16}$, $R^{17}$, $R^{18}$ and $R^{19}$ in general formula (1). Substituents which may be substituted on these alkyl, cycloalkyl, aryl, aralkyl, alkenyl, alkynyl, aralkyloxy and heteroaryl groups include an alkyl group, a cycloalkyl group, an aryl group, an aralkyl group, an alkyloxy group, an aryloxy group, an aralkyloxy group and a heteroaryl group, as well as a halogeno group, a silyl group, an amino group and an optionally protected hydroxyl group, etc., as discussed above for $R^{12}$, $R^{13}$, $R^{14}$, $R^{15}$, $R^{16}$, $R^{17}$, $R^{18}$ and $R^{19}$.

An explanation will be made of $R^4$ and $R^9$ in general formulae ($G^{C-1}$) and ($G^{C-2}$). $R^4$ and $R^9$ are each independently selected from an alkyl group, a cycloalkyl group, an aryl group, an aralkyl group, an alkenyl group, or a heteroaryl group. Moreover, these alkyl, cycloalkyl, aryl, aralkyl, alkenyl and heteroaryl groups are optionally substituted. These alkyl, cycloalkyl, aryl, aralkyl, alkenyl and heteroaryl groups are selected from an alkyl group, a cycloalkyl group, an aryl group, an aralkyl group, an alkenyl group and a heteroaryl group as discussed above for $R^{12}$, $R^{13}$, $R^{14}$, $R^{15}$, $R^{16}$, $R^{17}$, $R^{18}$ and $R^{19}$ in general formula (1). Substituents which may be substituted on these alkyl, cycloalkyl, aryl, aralkyl, alkenyl and heteroaryl groups include an alkyl group, a cycloalkyl group, an aryl group, an aralkyl group, an alkyloxy group, an aryloxy group, an aralkyloxy group and a heteroaryl group, as well as a halogeno group, a silyl group, an amino group and an optionally protected hydroxyl group, etc., as discussed above for $R^{12}$, $R^{13}$, $R^{14}$, $R^{15}$, $R^{16}$, $R^{17}$, $R^{18}$ and $R^{19}$.

An explanation will be made of $R^5$, $R^6$, $R^7$, $R^8$, $R^{10}$ and $R^{11}$ in general formulae ($G^{C-1}$) and ($G^{C-2}$). $R^5$, $R^6$, $R^7$, $R^8$, $R^{10}$ and $R^{11}$ are each independently selected from a hydrogen atom, an alkyl group, a cycloalkyl group, an aryl group, an aralkyl group, an alkenyl group, an alkoxy group, an aryloxy group, an aralkyloxy group, a heteroaryl group, or an amino group. Moreover, these alkyl, cycloalkyl, aryl, aralkyl, alkenyl, alkoxy, aryloxy, aralkyloxy, heteroaryl and amino groups are optionally substituted. These alkyl, cycloalkyl, aryl, aralkyl, alkenyl, alkoxy, aryloxy, aralkyloxy, heteroaryl and amino groups are selected from an alkyl group, a cycloalkyl group, an aryl group, an aralkyl group, an alkenyl group, an alkyloxy group, an aryloxy group, an aralkyloxy group, a heteroaryl group and an amino group, respectively, as discussed above for $R^{12}$, $R^{13}$, $R^{14}$, $R^{15}$, $R^{16}$, $R^{17}$, $R^{18}$ and $R^{19}$ in general formula (1). Substituents which may be substituted on these alkyl, cycloalkyl, aryl, aralkyl, alkenyl, alkoxy, aryloxy, aralkyloxy, heteroaryl and amino groups include an alkyl group, a cycloalkyl group, an aryl group, an aralkyl group, an alkyloxy group, an aryloxy group, an aralkyloxy group and a heteroaryl group, as well as a halogeno group, a silyl group, an amino group and an optionally protected hydroxyl group, etc., as discussed above for $R^{12}$, $R^{13}$, $R^{14}$, $R^{15}$, $R^{16}$, $R^{17}$, $R^{18}$ and $R^{19}$.

In a preferred embodiment, the compound of the present invention is specifically exemplified by a compound of general formula (1) wherein $R^{12}$, $R^{13}$, $R^{14}$, $R^{15}$, $R^{16}$, $R^{17}$, $R^{18}$ and $R^{19}$ are all hydrogen atoms, i.e., a compound represented by the following general formula (3):

[Formula 16]

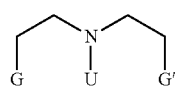

(3)

wherein G, G' and U are as defined above in general formula (1).

In a more preferred embodiment, the compound of the present invention is specifically exemplified by a compound represented by general formula ($4^A$) or ($4^B$)

[Formula 17]

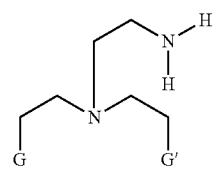

($4^A$)

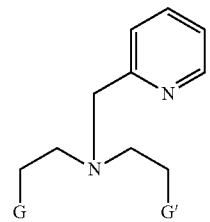

($4^B$)

wherein G and G' are as defined above in general formula (1).

In an even more preferred embodiment, the compound of the present invention is specifically exemplified by a compound represented by general formula ($5^A$) or ($5^B$):

[Formula 18]

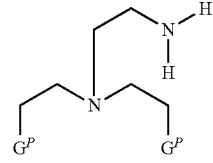

($5^A$)

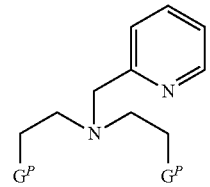

($5^B$)

wherein each $G^P$ is independently as defined above in general formula (1), and more preferably exemplified by compounds represented by general formulae ($6^A$) and ($6^B$):

[Formula 19]

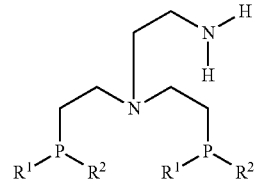

($6^A$)

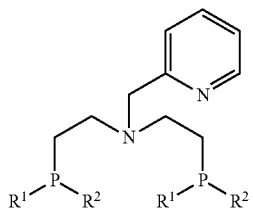

(6$^B$)

wherein R$^1$ and R$^2$ are as defined above in general formula (1). It should be noted that R$^1$ and R$^2$ appearing twice or more may be either the same or different.

Among these compounds represented by general formulae (1), (3), (4$^A$) (4$^B$) (5$^A$), (5$^B$), (6$^A$) and (6$^B$) according to the present invention, some are unstable in air, and some are difficult to purify and weigh because they are highly viscous liquid substances. Thus, for easy handling, these compounds may be reacted with a Bronsted acid, as specifically exemplified by a halogenated hydroacid, perchloric acid, nitric acid, sulfuric acid, a sulfonic acid, a carboxylic acid, phenols, phosphoric acid, hexafluorophosphoric acid, boric acid and tetrafluoroboric acid, etc., and thereby converted into corresponding Bronsted acid salts.

Specific examples of a halogenated hydroacid include hydrofluoric acid, hydrochloric acid, hydrobromic acid and hydroiodic acid, etc. Specific examples of a sulfonic acid include methanesulfonic acid, trifluoromethanesulfonic acid, p-toluenesulfonic acid and 10-camphorsulfonic acid, etc. Specific examples of a carboxylic acid include formic acid, acetic acid, trifluoroacetic acid, benzoic acid, salicylic acid, oxalic acid and tartaric acid, etc. Specific examples of phenols include phenol, p-cresol, p-nitrophenol and pentafluorophenol, etc.

When a Bronsted acid salt of the compound (1) of the present invention is used in the manufacture of a transition metal complex having the compound (1) of the present invention as a ligand (hereinafter referred to as the transition metal complex of the present invention), the Bronsted acid salt may be directly used in the reaction, or may be treated with a base outside the reaction system to liberate the compound (1) of the present invention before use in the reaction, or may be treated with a base within the reaction system to liberate the compound (1) of the present invention during the reaction.

Further, in a case where at least one of G and G' in the compound (1) of the present invention is represented by general formula (G$^P$) and L in general formula (G$^P$) is boron trihydride (BH$_3$), when the compound (1) of the present invention is used in the manufacture of the transition metal complex of the present invention, it may be directly used in the reaction, or may be treated to dissociate boron trihydride outside the reaction system before use in the reaction, or may be treated within the reaction system to dissociate boron trihydride during the reaction. For dissociation of boron trihydride, a dissociating agent is preferably used together, and examples of a dissociating agent for boron trihydride include amines such as diethylamine, triethylamine, morpholine and 1,4-diazabicyclo[2,2,2]octane.

Particularly preferred embodiments of the compound of the present invention specifically include the following compounds and so on.

[Formula 20]

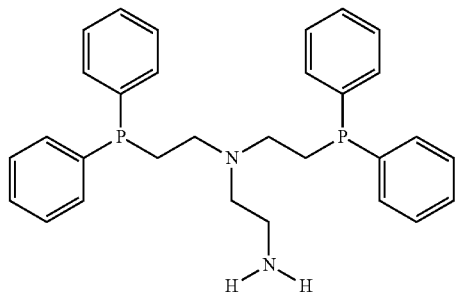

(7$^A$)

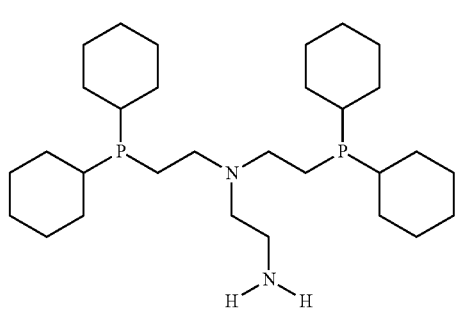

(6$^A$-1)

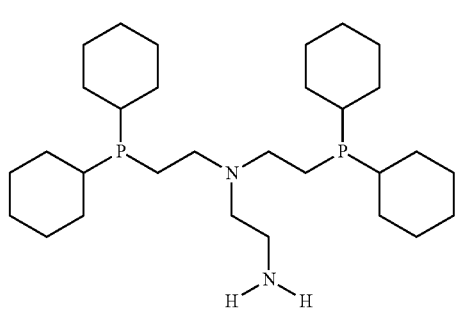

(6$^A$-2)

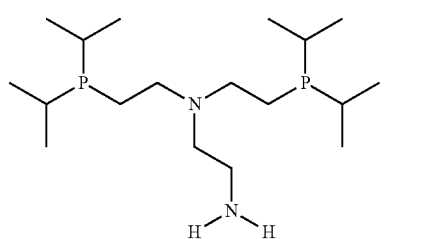

(6$^A$-3)

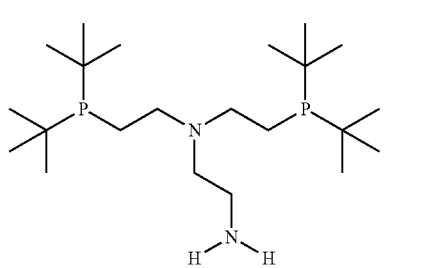

(6$^A$-4)

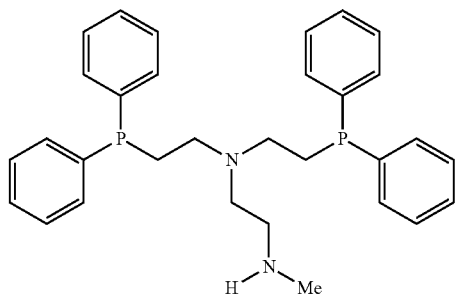

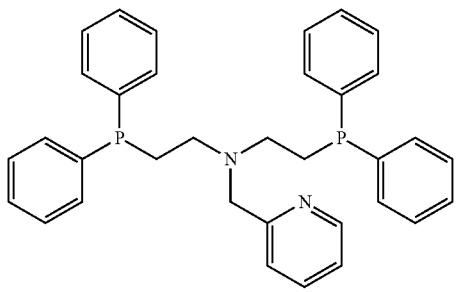

(7^B)

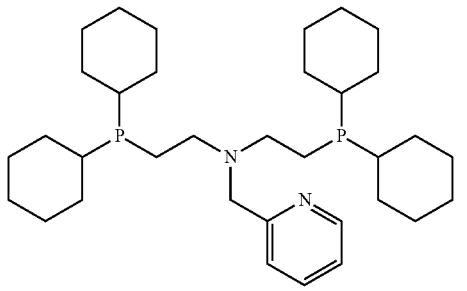

(6^B-1)

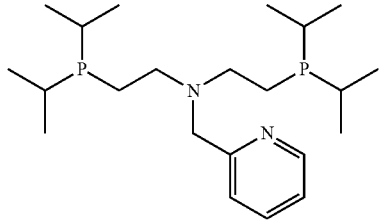

(6^B-2)

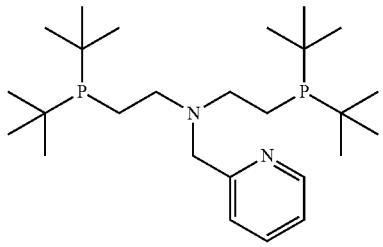

(6^B-3)

According to a preferred embodiment of the present invention, the compound of the present invention can function as a ligand, particularly a tetradentate ligand, in a transition metal complex, and may be reacted with various transition metal compounds to obtain transition metal complexes showing catalytic activity advantageous to various organic synthesis reactions.

[The Transition Metal Complex of the Present Invention]

The transition metal complex of the present invention will then be described in more detail below. The metal species in the transition metal complex of the present invention is not limited in any way as long as it is capable of coordinating to the compound (1) of the present invention. However, in terms of catalytic activity in organic synthesis reactions, preferred are metal species selected from the group consisting of manganese, which is a transition metal of Group 7, and transition metals of Groups 8 to 11, more preferred are metal species selected from the group consisting of manganese, transition metals of Group 8, transition metals of Group 9 and transition metals of Group 10, even more preferred are metal species selected from transition metals of Group 8, and particularly preferred metal species are iron and ruthenium, etc. The transition metal complex of the present invention is obtained when the compound (1) of the present invention is reacted with a transition metal compound serving as a transition metal source. Such a transition metal compound is also not limited in any way as long as it can be reacted with the compound (1) of the present invention, but preferred are compounds of manganese, which is a transition metal of Group 7, as well as compounds of transition metals of Groups 8 to 11, i.e., iron compounds, ruthenium compounds, osmium compounds, cobalt compounds, rhodium compounds, iridium compounds, nickel compounds, palladium compounds, platinum compounds, copper compounds, silver compounds and gold compounds, etc., more preferred are compounds of manganese, which is a transition metal of Group 7, as well as compounds of transition metals of Groups 8 to 10, i.e., iron compounds, ruthenium compounds, osmium compounds, cobalt compounds, rhodium compounds, iridium compounds, nickel compounds, palladium compounds and platinum compounds, etc., even more preferred are compounds of transition metals of Group 8, i.e., iron compounds, ruthenium compounds and osmium compounds, etc., and particularly preferred transition metal compounds are iron compounds and ruthenium compounds, etc. Preferred transition metal compounds will be further described in more detail below.

Examples of manganese compounds include monovalent, divalent and trivalent manganese compounds. Specific examples include manganese(II) chloride, manganese(II) chloride tetrahydrate, manganese(II) cyclohexabutyrate, manganese(II) formate, manganese(II) formate hydrate, manganese(II) perchlorate hydrate, manganese(II) fluoride, manganese(III) fluoride, manganese(II) iodide, manganese(II) sulfate monohydrate, manganese(II) carbonate, manganese(II) carbonate hydrate, manganese(II) nitrate hydrate, manganese(II) bromide, manganese(II) bromide tetrahydrate, manganese(III) acetylacetonate, manganese(II) acetylacetonate, manganese(II) phthalocyanine, bis(cyclopentadienyl)manganese(II), tris(2,2,6,6-tetramethyl-3,5-heptanedionato)manganese(III), manganese(II) oxalate dihydrate, manganese(III) 2,4-pentanedionate, tris(2,2,6,6-tetramethyl-3,5-heptanedionato)manganese(III), bis(hexafluoroacetylacetonato)manganese(II), manganese(II) benzoate tetrahydrate, manganese(II) acetate, manganese (III) acetate dihydrate, bis(ethylcyclopentadienyl)manganese(II), bis(pentamethylcyclopentadienyl)manganese(II), manganese(III) phosphate hydrate, manganese(III) tetraphenylporphyrin acetate, manganese(II) hypophosphite monohydrate, manganese(III) tetrakis(4-benzoic acid)porphyrin and bromopentacarbonylmanganese(I), etc., with bromopentacarbonylmanganese(I) being preferred.

Examples of iron compounds include zero-valent, divalent and trivalent iron compounds. Specific examples include pentacarbonyliron(0), nonacarbonyldiiron(0), dodecacarbonyltriiron(0), iron(II) fluoride, iron(II) chloride, iron(II) chloride tetrahydrate, iron(II) bromide, iron(II) iodide, iron(II) sulfate monohydrate, iron(II) sulfate heptahydrate, iron(II) perchlorate hexahydrate, iron(II) trifluoromethanesulfonate, iron(II) tetrafluoroborate hexahydrate, iron(II) acetate, ammonium iron(II) sulfate hexahydrate, iron(II) acetylacetonate, iron(III) fluoride, iron(III) fluoride trihydrate, iron(III) chloride, iron(III) chloride hexahydrate, iron(III) bromide, iron(III) sulfate hydrate, iron(III) nitrate nonahydrate, iron(III) perchlorate hydrate, iron(III) trifluoromethanesulfonate, iron(III) phosphate hydrate, iron(III) acetylacetonate and iron(III) trifluoroacetylacetonate, etc., with iron(II) chloride being preferred.

Examples of ruthenium compounds include zero-valent, divalent and trivalent ruthenium compounds. Specific examples include triruthenium(0) dodecacarbonyl, dichloro (benzene)ruthenium(II) dimer, dichloro(p-cymene)ruthenium(II) dimer, dichloro(mesitylene)ruthenium(II) dimer, dichloro(hexamethylbenzene)ruthenium(II) dimer, diiodo (p-cymene)ruthenium(II) dimer, dipivalato(p-cymene)ruthenium(II), bis(7-methallyl)(1,5-cyclooctadiene)ruthenium (II), dichloro(1,5-cyclooctadiene)ruthenium(II) polymer, dichloro(norbornadiene)ruthenium(II) polymer, dichlorotris (triphenylphosphine)ruthenium(II), chlorohydridotris(triphenylphosphine)ruthenium(II) toluene adduct, dihydridotetrakis(triphenylphosphine)ruthenium(II), carbonylchlorohydridotris(triphenylphosphine)ruthenium (II), carbonyldihydridotris(triphenylphosphine)ruthenium (II), dichlorotetrakis(dimethyl sulfoxide)ruthenium(II), ruthenium(III) chloride, ruthenium(III) chloride hydrate, ruthenium(III) iodide, ruthenium(III) iodide hydrate, hexaammineruthenium(III) trichloride and ruthenium(III) acetylacetonate, etc., with dichloro(p-cymene)ruthenium(II) dimer, dichlorotris(triphenylphosphine)ruthenium(II) and dipivalato(p-cymene)ruthenium(II) being preferred.

Examples of osmium compounds include divalent and trivalent osmium compounds. Specific examples include dichloro(p-cymene)osmium(II) dimer, carbonylchlorohydridotris(triphenylarsine)osmium(II), osmium(III) chloride and osmium(III) chloride trihydrate, etc.

Examples of cobalt compounds include divalent and trivalent cobalt compounds. Specific examples include cobalt(II) fluoride, cobalt(II) fluoride tetrahydrate, cobalt(II) chloride, cobalt(II) chloride dihydrate, cobalt(II) chloride hexahydrate, cobalt(II) bromide, cobalt(II) bromide dihydrate, cobalt(II) iodide, cobalt(II) sulfate monohydrate, cobalt(II) sulfate heptahydrate, cobalt(II) nitrate hexahydrate, cobalt(II) perchlorate hexahydrate, cobalt(II) tetrafluoroborate hexahydrate, cobalt(II) acetate, cobalt(II) acetate tetrahydrate, cobalt(II) cyanide dihydrate, cobalt(II) acetylacetonate, cobalt(II) acetylacetonate hydrate, cobalt (II) hexafluoroacetylacetonate hydrate, cobalt(III) fluoride, cobalt(III) acetylacetonate and hexaamminecobalt(III) trichloride, etc.

Examples of rhodium compounds include monovalent, divalent and trivalent rhodium compounds. Specific examples include chloro(1,5-hexadiene)rhodium(I) dimer, chloro(1,5-cyclooctadiene)rhodium(I) dimer, chlorobis(cyclooctene)rhodium(I) dimer, bis(1,5-cyclooctadiene)rhodium(I) trifluoromethanesulfonate, bis(1,5-cyclooctadiene) rhodium(I) hexafluoroantimonate, bis(1,5-cyclooctadiene) rhodium(I) tetrafluoroborate, bis(norbornadiene)rhodium(I) trifluoromethanesulfonate, (acetylacetonato)bis(ethylene) rhodium(I), (acetylacetonato)(1,5-cyclooctadiene)rhodium (I), (acetylacetonato)(norbornadiene)rhodium(I), bis(acetonitrile)(1,5-cyclooctadiene)rhodium(I) tetrafluoroborate, bis(1,5-cyclooctadiene)rhodium(I) tetrakis[bis(3,5-trifluoromethyl)phenyl]borate, tetrakis(triphenylphosphine)rhodium(I) hydride, (acetylacetonato)dicarbonylrhodium(I), rhodium(III) chloride, rhodium(III) chloride trihydrate, rhodium(III) nitrate hydrate, tetrakis(μ-trifluoroacetato)dirhodium(II), tetrakis(μ-acetato)dirhodium(II), tetrakis(μ-acetato)dirhodium(II) dihydrate, tetrakis(μ-trimethylacetato) dirhodium(II), tetrakis(μ-octanoato)dirhodium(II), tetrakis (triphenylacetato)dirhodium(II) and rhodium(III) acetylacetonate, etc.

Examples of iridium compounds include monovalent and trivalent iridium compounds. Specific examples include chloro(1,5-cyclooctadiene)iridium(I) dimer, (1,5-cyclooctadiene)(methoxy)iridium(I) dimer, bis(cyclooctadiene)iridium(I) tetrakis[3,5-bis(trifluoromethyl)phenyl]borate, bis(1,5-cyclooctadiene)iridium(I) tetrafluoroborate, (1,5-cyclooctadiene)(hexafluoroacetylacetonato)iridium(I), (acetylacetonato)(1,5-cyclooctadiene)iridium(I), (acetylacetonato)dicarbonyliridium(I), iridium(III) chloride, iridium (III) chloride hydrate and iridium(III) acetylacetonate, etc.

Examples of nickel compounds include zero-valent and divalent nickel compounds. Specific examples include bis (1,5-cyclooctadiene)nickel(0), tetrakis(triphenylphosphine) nickel(0), dichlorobis(triphenylphosphine)nickel(II), nickel (II) fluoride, nickel(II) chloride, nickel(II) chloride monohydrate, nickel(II) chloride hexahydrate, nickel(II) bromide, nickel(II) bromide trihydrate, nickel(II) iodide, nickel(II) trifluoromethanesulfonate, nickel(II) sulfate, nickel(II) sulfate hexahydrate, nickel(II) sulfate heptahydrate, nickel(II) nitrate hexahydrate, nickel(II) perchlorate hexahydrate, nickel(II) oxalate dihydrate, nickel(II) acetate tetrahydrate, nickel(II) acetylacetonate and nickel(II) hexafluoroacetylacetonate hydrate, etc.

Examples of palladium compounds include zero-valent and divalent palladium compounds. Specific examples include bis(dibenzylideneacetone)palladium(0), tris(dibenzylideneacetone)dipalladium(0), tetrakis(triphenylphosphine)palladium(0), bis(acetonitrile)dichloropalladium(II), bis(acetonitrile)dibromopalladium(II), bis(benzonitrile)dichloropalladium(II), bis(benzonitrile)dibromopalladium(II), dichloro(1,5-cyclooctadiene)palladium(II), bis(triphenylphosphine)dichloropalladium(II), (π-allyl)palladium(II) chloride dimer, (π-methallyl)palladium(II) chloride dimer, (π-cinnamyl)palladium(II) chloride dimer, palladium(II) chloride, palladium(II) bromide, palladium(II) iodide, palladium(II) sulfate, palladium(II) nitrate dihydrate, palladium (II) trifluoroacetate, palladium(II) acetate, palladium(II) propionate, palladium(II) pivalate, palladium(II) cyanide, palladium(II) acetylacetonate, palladium(II) hexafluoroacetylacetonate, tetrakis(acetonitrile)palladium(II) tetrafluoroborate, sodium tetrachloropalladate(II) and potassium tetrachloropalladate(II), etc.

Examples of platinum compounds include divalent and tetravalent platinum compounds. Specific examples include platinum(II) chloride, platinum(II) bromide, platinum(II) iodide, platinum(II) cyanide, platinum(II) acetylacetonate, potassium tetrachloroplatinate(II), dichloro(1,5-cyclooctadiene)platinum(II), cis-bis(acetonitrile)dichloroplatinum(II), trans-bis(acetonitrile)dichloroplatinum(II), cis-bis(benzonitrile)dichloroplatinum(II), platinum(IV) chloride and potassium hexachloroplatinate(IV), etc.

Examples of copper compounds include monovalent and divalent copper compounds. Specific examples include copper(I) oxide, copper(I) chloride, copper(I) bromide, copper (I) iodide, copper(I) trifluoromethanesulfonate benzene complex, copper(I) acetate, copper(I) cyanide, tetrakisacetonitrile copper(I) tetrafluoroborate, tetrakisacetonitrile copper(I) hexafluorophosphate, copper(II) oxide, copper(II) fluoride, copper(II) fluoride dihydrate, copper(II) chloride, copper(II) chloride dihydrate, copper(II) bromide, copper (II) trifluoromethanesulfonate, copper(II) sulfate, copper(II) sulfate pentahydrate, copper(II) nitrate trihydrate, copper(II) perchlorate hexahydrate, copper(II) tetrafluoroborate hexahydrate, copper(II) trifluoroacetate, copper(II) acetate, copper(II) acetate monohydrate, copper(II) acetylacetonate and copper(II) hexafluoroacetylacetonate hydrate, etc.

Examples of silver compounds include monovalent and divalent silver compounds. Specific examples include silver (I) oxide, silver(I) fluoride, silver(I) chloride, silver(I) bromide, silver(I) trifluoromethanesulfonate, silver(I) methanesulfonate, silver(I) p-toluenesulfonate, silver(I) sulfate, silver(I) nitrate, silver(I) perchlorate, silver(I) perchlorate monohydrate, silver(I) tetrafluoroborate, silver(I) hexafluorophosphate, silver(I) trifluoroacetate, silver(I) acetate, silver(I) benzoate, silver(I) carbonate, silver(I) nitrite, silver(I) cyanate, silver(I) acetylacetonate, silver(II) fluoride and silver(II) picolinate, etc.

Examples of gold compounds include monovalent and trivalent gold compounds. Specific examples include gold(I) chloride, gold(I) iodide, gold(I) cyanide, gold(III) chloride, gold(III) chloride dihydrate, gold(III) bromide, chloroauric (III) acid tetrahydrate and potassium chloroaurate(III), etc.

A transition metal complex of Group 8 having the compound of the present invention as a ligand is preferably exemplified by a metal complex represented by general formula (8):

$$[M^8X^1X^2(L^1)_k(L^2)_l(L^3)]_n \quad (8)$$

wherein $M^8$ represents Fe, Ru or Os, $X^1$ and $X^2$ each independently represent a monovalent anionic monodentate ligand, $L^1$ and $L^2$ each independently represent a neutral monodentate ligand, k and l represent the coordination numbers of $L^1$ and $L^2$, respectively, and each independently represent 0 or 1, $L^3$ represents the compound (1) of the present invention or a Bronsted acid salt thereof, and n represents 1 or 2, provided that n represents 1 when the sum total of k and l is an integer of 1 to 2 or n represents 1 or 2 when this sum total is 0.

Likewise, a transition metal complex of Group 9 having the compound of the present invention as a ligand is preferably exemplified by a metal complex represented by the above general formula (9):

$$M^9X^1X^2X^3(L^1)_k(L^2)_l(L^3) \quad (9)$$

wherein $M^9$ represents Co, Rh or Ir, $X^1$, $X^2$ and $X^3$ each independently represent a monovalent anionic monodentate ligand, $L^1$ and $L^2$ each independently represent a neutral monodentate ligand, k and l represent the coordination numbers of $L^1$ and $L^2$, respectively, and each independently represent 0 or 1, and $L^3$ represents the compound (1) of the present invention or a Bronsted acid salt thereof.

Further, a transition metal complex of Group 10 having the compound of the present invention as a ligand is preferably exemplified by a metal complex represented by the above general formula (10):

$$M^{10}X^1X^2(L^3) \quad (10)$$

wherein $M^{10}$ represents Ni, Pd or Pt, $X^1$ and $X^2$ each independently represent a monovalent anionic monodentate ligand, and $L^3$ represents the compound (1) of the present invention or a Bronsted acid salt thereof.

Furthermore, a manganese complex having the compound of the present invention as a ligand is preferably exemplified by a metal complex represented by the above general formula (11):

$$MnX(L^1)_k(L^2)_l(L^3) \quad (11)$$

wherein X represents a monovalent anionic monodentate ligand, $L^1$ and $L^2$ each independently represent a neutral monodentate ligand, k and l represent the coordination numbers of $L^1$ and $L^2$, respectively, and each independently represent 0 or 1, and $L^3$ represents the compound (1) of the present invention or a Bronsted acid salt thereof.

$M^8$ represents a divalent transition metal ion of Group 8 selected from the group consisting of a divalent iron (Fe) ion, a divalent ruthenium (Ru) ion or a divalent osmium (Os) ion, and preferably represents a divalent ruthenium ion. $M^9$ represents a trivalent transition metal ion of Group 9 selected from the group consisting of a trivalent cobalt (Co) ion, a trivalent rhodium (Rh) ion or a trivalent iridium (Ir) ion, while $M^{10}$ represents a divalent transition metal ion of Group 10 selected from the group consisting of a divalent nickel (Ni) ion, a divalent palladium (Pd) ion or a divalent platinum (Pt) ion. Mn represents a monovalent manganese (Mn) ion. $X^1$, $X^2$ and $X^3$ each independently represent a monovalent anionic monodentate ligand, while $L^1$ and $L^2$ each independently represent a neutral monodentate ligand. k and l represent the coordination numbers of $L^1$ and $L^2$, respectively, and each independently represent an integer of 0 or 1. $L^3$ represents the compound of the present invention serving as a tetradentate ligand. In the above general formula (8), n represents 1 when the sum total of k and l in the above general formula (8) is an integer of 1 to 2, or n represents 1 or 2 when this sum total is 0.

A detailed explanation will then be made of $X^1$, $X^2$ and $X^3$ in the above general formulae (8), (9), (10) and (11), i.e., monovalent anionic monodentate ligands. A monovalent anionic monodentate ligand refers to a functional group having a monovalent negative charge and capable of binding via a single bond to a metal in a metal complex, and an anion capable of functioning as a counter ion for a metal complex, as well as a group having both properties simultaneously. Specific examples (expressed as functional group name/anion name, followed by their respective general formulae in parentheses) include a hydrido group/hydride ion (—H/H⁻), a hydroxyl group/hydroxide ion (—OH/HO⁻), an alkoxy group/alkoxide ion (—OR/RO⁻), an aryloxy group/aryloxide ion (—OAr/ArO⁻), an acyloxy group/carboxylate ion (—OC(=O)R/RCO₂⁻), a bicarbonate ion (HCO₃⁻), a mercapto group/hydrogen sulfide ion (—SH/HS⁻), an alkylthio group/alkylthiolate ion (—SR/RS⁻), an arylthio group/arylthiolate ion (—SAr/ArS⁻), a sulfonyloxy group/sulfonate ion (—OSO₂R/RSO₃⁻), a thiocyanate ion (NCS⁻), a halogeno group/halide ion (—X/X⁻), a hypochlorite ion (ClO⁻), a chlorite ion (ClO₂⁻), a chlorate ion (CO₃⁻), a perchlorate ion (ClO₄⁻), a tetrahydroborate ion (BH₄⁻), a tetrafluoroborate ion (BF₄⁻), a tetraarylborate ion (BAr₄⁻), a dihydrogen phosphate ion (H₂PO₄⁻), a hexafluorophosphate ion (PF₆⁻), a hexafluoroantimonate ion (SbF₆⁻), an azi group/azide ion (—N₃/N₃⁻), a cyano group/cyanide ion (—CN/CN⁻), a nitro group/nitrito group/nitrite ion (—NO₂/—ONO/NO₂⁻), a nitrate ion (NO₃⁻), a hydrogen sulfate ion (HSO₄⁻), a tetrahydroxoaluminate ion ([Al(OH)₄]⁻), a tetrahydroxochromate ion ([Cr(OH)₄]⁻), a dicyanoargentate ion ([Ag(CN)₂]⁻) and a chloroaurate ion ([AuCl₄]⁻), etc.

In terms of catalytic activity in the transition metal complex of the present invention, preferred monovalent anionic monodentate ligands are specifically exemplified by a hydrido group/hydride ion, a hydroxyl group/hydroxide ion, an alkoxy group/alkoxide ion, an aryloxy group/aryloxide ion, an acyloxy group/carboxylate ion, a sulfonyloxy group/sulfonate ion, a halogeno group/halide ion, a perchlorate ion, a tetrahydroborate ion, a tetrafluoroborate ion, a tetraarylborate ion, a hexafluorophosphate ion and a hexafluoroantimonate ion, etc., and more preferred are a hydrido group/hydride ion, a halogeno group/halide ion and a tetrahydroborate ion, etc.

Preferred monovalent anionic monodentate ligands will be further described in more detail below. Examples of an alkoxy group/alkoxide ion include alkoxy groups/alkoxide ions containing 1 to 10 carbon atoms, preferably 1 to 4 carbon atoms, as specifically exemplified by a methoxy group/methoxide ion, an ethoxy group/ethoxide ion, a 1-propoxy group/1-propoxide ion, a 2-propoxy group/2- propoxide ion, a 1-butoxy group/1-butoxide ion, a 2-butoxy group/2-butoxide ion and a tert-butoxy group/tert-butoxide ion, etc.

Examples of an aryloxy group/aryloxide ion include aryloxy groups/aryloxide ions containing 6 to 14 carbon atoms, preferably 6 to 10 carbon atoms, as specifically exemplified by a phenoxy group/phenoxide ion, a p-methylphenoxy group/p-methylphenoxide ion, a 2,4,6-trimethylphenoxy group/2,4,6-trimethylphenoxide ion, a p-nitrophenoxy group/p-nitrophenoxide ion, a pentafluorophenoxy group/pentafluorophenoxide ion, a 1-naphthyloxy group/1-naphthyloxide ion and a 2-naphthyloxy group/2-naphthyloxide ion, etc.

Examples of an acyloxy group/carboxylate ion include acyloxy groups/carboxylate ions containing 1 to 18 carbon atoms, preferably 1 to 6 carbon atoms, as specifically exemplified by a formyloxy group/formate ion, an acetoxy group/acetate ion, a trifluoroacetoxy group/trifluoroacetate ion, a propanoyloxy group/propionate ion, an acryloyloxy group/acrylate ion, a butanoyloxy group/butyrate ion, a pivaloyloxy group/pivalate ion, a pentanoyloxy group/valerate ion, a hexanoyloxy group/caproate ion, a benzoyloxy group/benzoate ion and a pentafluorobenzoyloxy group/pentafluorobenzoate ion, etc.

Examples of a sulfonyloxy group/sulfonate ion include sulfonyloxy groups/sulfonate ions containing 1 to 18 carbon atoms, preferably 1 to 10 carbon atoms, as specifically exemplified by a methanesulfonyloxy group/methanesulfonate ion, a trifluoromethanesulfonyloxy group/trifluoromethanesulfonate ion, a n-nonafluorobutanesulfonyloxy group/n-nonafluorobutanesulfonate ion, a p-toluenesulfonyloxy group/p-toluenesulfonate ion and a 10-camphorsulfonyloxy group/10-camphorsulfonate ion, etc.

Specific examples of a halogeno group/halide ion include a fluoro group/fluoride ion, a chloro group/chloride ion, a bromo group/bromide ion and an iodo group/iodide ion, with a chloro group/chloride ion being preferred.

Specific examples of a tetraarylborate ion include a tetraphenylborate ion, a tetrakis(pentafluorophenyl)borate ion and a tetrakis[3,5-bis(trifluoromethyl)phenyl]-borate ion, etc.

Moreover, these monovalent anionic monodentate ligands are not present alone. Thus, in the manufacture of the transition metal complex of the present invention, they are preferably used in the form of corresponding monovalent anionic monodentate ligand sources, i.e., conjugate acids derived from monovalent anionic monodentate ligands or salts derived from monovalent anionic monodentate ligands.

A detailed explanation will then be made of $L^1$ and $L^2$ in the above general formulae (8), (9), (10) and (11), i.e., neutral monodentate ligands. A neutral monodentate ligand refers to an organic compound having at least one nonionic functional group capable of coordinating to a metal, and specific examples (expressed as common name, followed by general formula in parentheses) include water ($H_2O$), an alcohol (ROH), an ether (ROR'), a ketone (RC(=O)R'), an ester (RC(=O)OR'), a thiol (RSH), a sulfide (RSR'), a sulfoxide (RS(=O)R'), an amine (RR'R''N), an amide (RR'NC(=O)R''), a nitrile (RCN), an isonitrile (RNC), a heteroarene (HetArH), a secondary phosphine (RR'PH), a secondary phosphineoxide (RR'P(=O)H), a tertiary phosphine (RR'R''P), a phosphite ((RO)(R'O)(R''O)P), a phosphoroamidite ((RO)(R'O)PNR''R'''), a silylene (RR'Si:), a hydrogen molecule ($H_2$), a nitrogen molecule ($N_2$), carbon monoxide (CO) and nitrogen monoxide (NO), etc.

In terms of the catalytic activity of the transition metal complex of the present invention in organic synthesis reactions, preferred neutral monodentate ligands are exemplified by an alcohol, an ether, a sulfide, a sulfoxide, an amine, an amide, a nitrile, an isonitrile, a heteroarene, a secondary phosphine, a secondary phosphineoxide, a tertiary phosphine, a phosphite, a phosphoroamidite, a tertiary arsine, a carbene, a hydrogen molecule and carbon monoxide, and more preferred are a tertiary phosphine, a phosphite and carbon monoxide, etc.

Preferred neutral monodentate ligands will be further described in more detail below. Specific examples of an alcohol include methanol, ethanol, 2-propanol, 2,2,2-trifluoroethanol and 1,1,1,3,3,3-hexafluoro-2-propanol, etc.

Specific examples of an ether include dimethyl ether, diethyl ether, tetrahydrofuran and 1,4-dioxane, etc.

Specific examples of a sulfide include dimethyl sulfide, diethyl sulfide, diphenyl sulfide and tetrahydrothiophene, etc.

Specific examples of a sulfoxide include dimethyl sulfoxide and tetrahydrothiophene-1-oxide, etc. It should be noted that these sulfoxides may coordinate to a metal species either via the oxygen atom on the sulfur atom or via the sulfur atom.

Specific examples of an amine include ammonia, methylamine, dimethylamine, trimethylamine, ethylamine, diethylamine, triethylamine, isopropylamine, aniline, benzylamine, α-phenethylamine, β-phenethylamine, piperazine, piperidine and morpholine, etc.

Specific examples of an amide include N,N-dimethylformamide and N,N-dimethylacetamide, etc.

Specific examples of a nitrile include acetonitrile and benzonitrile, etc.

Specific examples of an isonitrile include (trimethylsilyl)methylisocyanide, isopropylisocyanide, 1-butylisocyanide, tert-butylisocyanide, 1-pentylisocyanide, 2-pentylisocyanide, cyclohexylisocyanide, 1,1,3,3-tetramethylbutylisocyanide, 1-adamantylisocyanide, 2,6-dimethylphenylisocyanide, 4-methoxyphenylisocyanide, 2-naphthylisocyanide, benzylisocyanide and α-methylbenzylisocyanide, etc., with 4-methoxyphenylisocyanide being preferred.

Specific examples of a heteroarene include furan, benzofuran, isobenzofuran, thiophene, thianaphthene, isothianaphthene, pyridine, quinoline, isoquinoline, 3H-pyrrole, 3H-indole, 2H-pyrrole, 1H-isoindole, oxazole, oxazoline, benzoxazole, isoxazole, isoxazoline, benzoisoxazole, thiazole, thiazoline, benzothiazole, isothiazole, isothiazoline, benzoisothiazole, imidazole, imidazoline, benzimidazole, pyrazole, 2-pyrazoline and indazole, etc.

Specific examples of a secondary phosphine include dimethylphosphine (11-1), diethylphosphine (11-2), diisopropylphosphine (11-3), di-tert-butylphosphine (11-4), dicyclopentylphosphine (11-5), dicyclohexylphosphine (11-6), diphenylphosphine (11-7), bis(2-methylphenyl)phosphine (11-8), bis(4-methylphenyl)phosphine (11-9), bis(3,5-dimethylphenyl)phosphine (11-10), bis(2,4,6-trimethylphenyl)phosphine (11-11), bis(2-methoxyphenyl)phosphine (11-12), bis(4-methoxyphenyl)phosphine (11-13), bis(4-trifluoromethylphenyl)phosphine (11-14), bis[3,5-bis(trifluoromethyl)phenyl]-phosphine (11-15), bis(3,5-di-tert-butyl-4-methoxyphenyl)phosphine (11-16), tert-butylphenylphosphine (11-17), di-1-adamantylphosphine (11-18), (11bS)-4,5-dihydro-3H-dinaphtho[2,1-c:1',2'-e]phosphepin (11-19) and di-2-furylphosphine (11-20), etc., with diphenylphosphine (11-7) being preferred. Specific examples of a secondary phosphine-boron trihydride complex include boron trihydride complexes of the secondary phosphines listed above as specific examples, with a dicyclohexylphosphine-boron trihydride complex (11-21) being preferred.
[Formula 21]
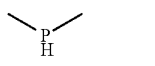
(11-1)
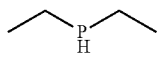
(11-2)
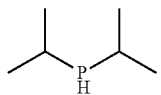
(11-3)
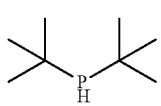
(11-4)
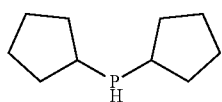
(11-5)
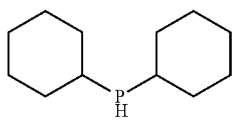
(11-6)
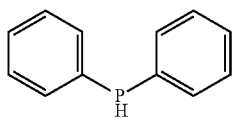
(11-7)
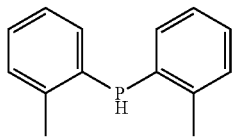
(11-8)
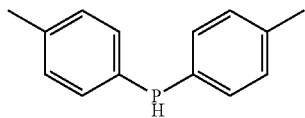
(11-9)
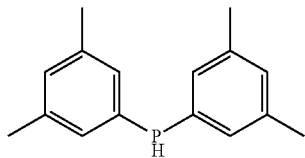
(11-10)
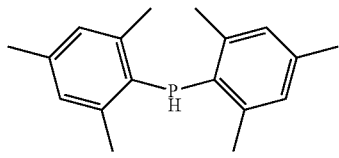
(11-11)
-continued
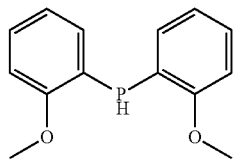
(11-12)
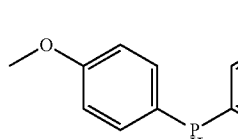
(11-13)
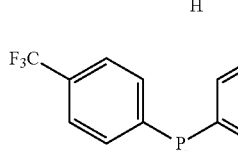
(11-14)
(11-15)
(11-16)
(11-17)
(11-18)
(11-19)
(11-20)

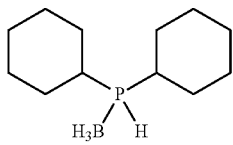

(11-21)

Specific examples of a secondary phosphineoxide include dimethylphosphineoxide, diethylphosphineoxide, diisopropylphosphineoxide, di-tert-butylphosphineoxide, dicyclopentylphosphineoxide, dicyclohexylphosphineoxide, diphenylphosphineoxide, bis(2-methylphenyl)phosphineoxide, bis(4-methylphenyl)phosphineoxide, bis(3,5-dimethylphenyl)phosphineoxide, bis(2,4,6-trimethylphenyl)phosphineoxide, bis(2-methoxyphenyl)phosphineoxide, bis(4-methoxyphenyl)phosphineoxide, bis(4-trifluoromethylphenyl)phosphineoxide, bis[3,5-bis(trifluoromethyl)phenyl]phosphineoxide, bis(3,5-di-tert-butyl-4-methoxyphenyl)-phosphineoxide, tert-butylphenylphosphineoxide, di-1-adamantylphosphineoxide, (11bS)-4,5-dihydro-3H-dinaphtho[2,1-c:1',2'-e]phosphepin-4-oxide and di-2-furylphosphineoxide, etc. It should be noted that these secondary phosphineoxides may coordinate to a metal species either via the oxygen atom on the phosphorus atom or via the phosphorus atom.

Examples of a tertiary phosphine include a compound represented by the following general formula (12):

[Formula 22]

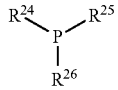

(12)

wherein P represents a phosphorus atom. $R^{24}$, $R^{25}$ and $R^{26}$ each independently represent a group selected from the group consisting of an alkyl group, an optionally substituted alkenyl group, an optionally substituted aryl group, an optionally substituted heteroaryl group or an optionally substituted aralkyl group. Any two or more of $R^{24}$, $R^{25}$ and $R^{26}$ may be joined together to form an optionally substituted ring.

In the above general formula (12), P represents a phosphorus atom. $R^{24}$, $R^{25}$ and $R^{26}$ each independently represent a group selected from the group consisting of an alkyl group, an optionally substituted alkenyl group, an optionally substituted aryl group, an optionally substituted heteroaryl group or an optionally substituted aralkyl group, and each preferably represent a group selected from the group consisting of an alkyl group, an optionally substituted aryl group and an optionally substituted heteroaryl group.

Such an alkyl group may be linear, branched or cyclic, as exemplified by alkyl groups containing 1 to 30 carbon atoms, preferably 1 to 20 carbon atoms, more preferably 1 to 10 carbon atoms. Specific examples include a methyl group, an ethyl group, a n-propyl group, a 2-propyl group, a cyclopropyl group, a n-butyl group, a 2-butyl group, an isobutyl group, a tert-butyl group, a cyclobutyl group, a n-pentyl group, a 2-pentyl group, a 3-pentyl group, a tert-pentyl group, a 2-methylbutyl group, a 3-methylbutyl group, a 2-methylbutan-3-yl group, a 2,2-dimethylpropyl group, a cyclopentyl group, a n-hexyl group, a 2-hexyl group, a 3-hexyl group, a tert-hexyl group, a 2-methylpentyl group, a 3-methylpentyl group, a 4-methylpentyl group, a 2-methylpentan-3-yl group, a 2-methylpentan-4-yl group, a 3-methylpentan-2-yl group, a 3-methylpentan-3-yl group, a 2,2-dimethylbutyl group, a 3,3-dimethylbutyl group, a 2,2-dimethylbutan-3-yl group, a cyclohexyl group, a n-heptyl group, a n-octyl group, a n-nonyl group, a n-decyl group, a 1-adamantyl group and a 2-adamantyl group, etc., with a methyl group, an ethyl group and a cyclohexyl group being preferred.

Such an alkenyl group may be linear, branched or cyclic, as exemplified by alkenyl groups containing 2 to 20 carbon atoms, preferably 2 to 14 carbon atoms, more preferably 2 to 8 carbon atoms. Specific examples include a vinyl group, a 1-propenyl group, a 2-propenyl group, an allyl group, a 1-cyclohexenyl group, a 1-styryl group and a 2-styryl group, etc.

An aryl group may be exemplified by aryl groups containing 6 to 18 carbon atoms, preferably 6 to 14 carbon atoms, more preferably 6 to 10 carbon atoms. Specific examples include a phenyl group, a 1-naphthyl group and a 2-naphthyl group, etc., with a phenyl group being preferred.

A heteroaryl group may be exemplified by heteroaryl groups derived from a 5- to 6-membered aromatic heterocyclic ring containing 1 to 4 heteroatoms selected from the group consisting of a nitrogen atom, an oxygen atom and a sulfur atom, and heteroaryl groups derived from a polycyclic aromatic heterocyclic ring generated upon annelation of the above aromatic heterocyclic ring with an aryl group as discussed above. Specific examples include a 2-furyl group, a 3-furyl group, a 2-thienyl group, a 3-thienyl group, a 2-benzofuryl group, a 3-benzofuryl group, a 2-benzothienyl group and a 3-benzothienyl group, etc., with a 2-furyl group being preferred.

An aralkyl group may be exemplified by aralkyl groups derived from alkyl groups as discussed above by replacement of at least one hydrogen atom with an aryl group as discussed above, and polycyclic aralkyl groups generated upon annelation of cyclic alkyl groups as discussed above with aryl groups as discussed above. Specific examples include a benzyl group, a 1-phenylethyl group, a 2-phenylethyl group, a 1-phenylpropyl group, a 2-phenylpropyl group, a 3-phenylpropyl group, a 1-phenyl-2-propyl group, a 2-phenyl-2-propyl group, a 1-indanyl group, 2-indanyl group and a 9-fluorenyl group, etc. $R^{24}$ to $R^{26}$ may be joined together to form an optionally substituted ring. Specific examples of such a ring include a phosphorane ring, a phosphole ring, a phosphinane ring and a phosphinine ring, etc.

Substituents which may be substituted on alkenyl, aryl, heteroaryl and aralkyl groups in $R^{24}$, $R^{25}$ and $R^{26}$ and on rings formed when $R^{24}$, $R^{25}$ and $R^{26}$ are joined together include an alkyl group, a halogenoalkyl group, an alkenyl group, an aryl group, a heteroaryl group, an aralkyl group, a hydroxyl group, an alkoxy group, an alkoxycarbonyl group, a carboxyl group, an amino group, a sulfo group and a halogeno group, etc. Among these substituents, alkyl, alkenyl, aryl, heteroaryl and aralkyl groups are the same as those in the detailed explanation of $R^{24}$, $R^{25}$ and $R^{26}$.

A halogenoalkyl group may be exemplified by groups derived from alkyl groups as discussed above by replacement of at least one hydrogen atom with a halogen atom. Specific examples include a trifluoromethyl group and a n-nonafluorobutyl group, etc., with a trifluoromethyl group being preferred.

An alkoxy group may be exemplified by alkoxy groups containing 1 to 10 carbon atoms, preferably 1 to 4 carbon atoms. Specific examples include a methoxy group, an ethoxy group, a 1-propoxy group, a 2-propoxy group, a 1-butoxy group, a 2-butoxy group and a tert-butoxy group, etc., with a methoxy group being preferred.

Specific examples of an alkoxycarbonyl group include a methoxycarbonyl group and so on. Specific examples of an amino group include a dimethylamino group and a 4-morpholinyl group, etc.

Specific examples of a halogeno group include a fluoro group, a chloro group, a bromo group and an iodo group, with a fluoro group and a chloro group being preferred.

Preferred specific examples of a tertiary phosphine represented by general formula (12) include trimethylphosphine (12-1), triethylphosphine (12-2), tricyclohexylphosphine (12-3), triphenylphosphine (12-4), tris(4-trifluoromethylphenyl)phosphine (12-5), tris(4-methoxyphenyl)phosphine (12-6) and tris(2-furyl)phosphine (12-7), etc.

[Formula 23]

(12-1)

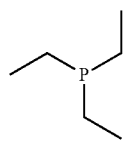
(12-2)

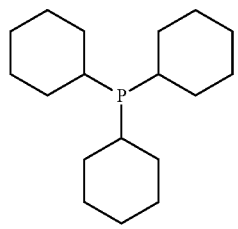
(12-3)

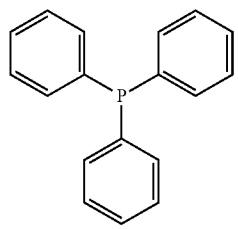
(12-4)

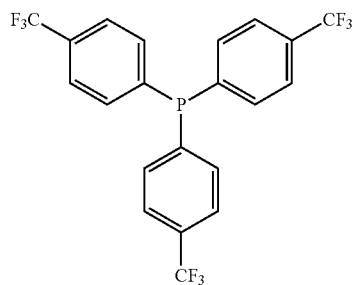
(12-5)

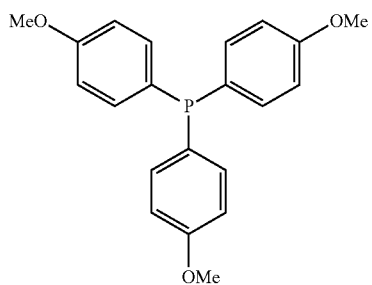
(12-6)

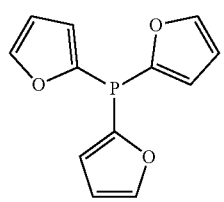
(12-7)

Specific examples of a phosphite include trimethyl phosphite, triethyl phosphite, tris(2,2,2-trifluoroethyl) phosphite, triisopropyl phosphite, triphenyl phosphite and 4-ethyl-2,6,7-trioxa-1-phosphabicyclo[2,2,2]octane, etc., with 4-ethyl-2,6,7-trioxa-1-phosphabicyclo[2,2,2]octane being preferred.

Specific examples of a phosphoroamidite include dimethyl-N,N-diisopropylphosphoroamidite, di-tert-butyl-N,N-diethylphosphoroamidite and dibenzyl-N,N-dimethylphosphoroamidite, etc.

Specific examples of a tertiary arsine include triphenylarsine and so on.

Examples of a carbene include organic compounds in singlet or triplet state which may be linear, branched or cyclic and whose molecule has a carbene carbon, i.e., a nonionic divalent carbon atom having six valence electrons. In terms of the catalytic activity of the metal complex of the present invention in organic synthesis reactions, preferred carbenes are singlet carbenes. Further, in terms of the chemical stability of these carbenes, more preferred carbenes are those in singlet state and containing a carbene carbon in a nitrogen-containing heterocyclic compound, i.e., so-called N-heterocyclic carbenes.

Specific examples of N-heterocyclic carbenes include imidazol-2-ylidene, imidazol-4-ylidene, dihydroimidazol-2-ylidene, tetrahydropyrimidin-2-ylidene, hexahydro-1,3-diazepin-2-ylidene, oxazol-2-ylidene, dihydrooxazol-2-ylidene, thiazol-2-ylidene, dihydrothiazol-2-ylidene, pyrazolylidene, triazolylidene and pyridoylidene, etc.

N-heterocyclic carbenes preferred in terms of their synthesis include imidazol-2-ylidene represented by the following general formula (13):

[Formula 24]

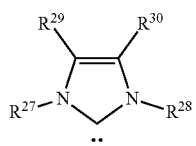
(13)

wherein the two dot leader represents a lone electron pair. $R^{27}$ and $R^{28}$ each independently represent a group selected from the group consisting of an alkyl group, an optionally substituted alkenyl group, an optionally substituted aryl group and an optionally substituted aralkyl group. $R^{29}$ and $R^{30}$ each independently represent a hydrogen atom and a group selected from the group consisting of an alkyl group, an optionally substituted alkenyl group, an optionally substituted aryl group and an optionally substituted aralkyl group. Any two or more of $R^{27}$, $R^{28}$, $R^{29}$ and $R^{30}$ may be joined together to form an optionally substituted ring, as well as dihydroimidazol-2-ylidene represented by the following general formula (14):

[Formula 25]

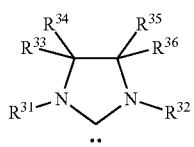
(14)

wherein the two dot leader represents a lone electron pair. $R^{31}$ and $R^{32}$ each independently represent a group selected from the group consisting of an alkyl group, an optionally substituted alkenyl group, an optionally substituted aryl group and an optionally substituted aralkyl group. $R^{33}$, $R^{34}$, $R^{35}$ and $R^{36}$ each independently represent a hydrogen atom and a group selected from the group consisting of an alkyl group, an optionally substituted alkenyl group, an optionally substituted aryl group and an optionally substituted aralkyl group. $R^{31}$ to $R^{36}$ may be joined together to form an optionally substituted ring.

Alkyl, alkenyl, aryl and aralkyl groups in $R^{27}$, $R^{28}$, $R^{29}$, $R^{30}$, $R^{31}$, $R^{32}$, $R^{33}$, $R^{34}$, $R^{35}$ and $R^{36}$ are the same as those in the detailed explanation of $R^{24}$, $R^{25}$ and $R^{26}$ in the above general formula (12). Substituents which may be substituted on alkenyl, aryl and aralkyl groups in $R^{27}$, $R^{28}$, $R^{29}$, $R^{30}$, $R^{31}$, $R^{32}$, $R^{33}$, $R^{34}$, $R^{35}$ and $R^{36}$, on rings formed when any two or more of $R^{27}$, $R^{28}$, $R^{29}$ and $R^{31}$ are joined together and on rings formed when any two or more of $R^{31}$, $R^{32}$, $R^{33}$, $R^{34}$, $R^{35}$ and $R^{36}$ are joined together include an alkyl group, a halogenoalkyl group, an alkenyl group, an aryl group, a heteroaryl group, an aralkyl group, a hydroxyl group, an alkoxy group, an amino group and a halogeno group, etc. These substituents are the same as those in the detailed explanation of alkenyl, aryl, heteroaryl and aralkyl groups in $R^{24}$, $R^{25}$ and $R^{26}$ in the above general formula (12) and in the detailed explanation of substituents which may be substituted on rings formed when any two or more of $R^{24}$, $R^{25}$ and $R^{26}$ are joined together.

Specific examples of imidazol-2-ylidene represented by general formula (13) include 1,3-dimethyl-2H-imidazol-2-ylidene (13-1), 1-ethyl-3-methyl-2H-imidazol-2-ylidene (13-2), 1,3-diisopropyl-2H-imidazol-2-ylidene (13-3), 1,3-di-tert-butyl-2H-imidazol-2-ylidene (13-4), 1,3-dicyclohexyl-2H-imidazol-2-ylidene (13-5), 1,3-bis(1-adamantyl)-2H-imidazol-2-ylidene (13-6), 1,3-dimethyl-2H-benzimidazol-2-ylidene (13-7), 1,3-di-tert-butyl-2H-benzimidazol-2-ylidene (13-8), 1,3-dicyclohexyl-2H-benzimidazol-2-ylidene (13-9), 1,3-bis(1-adamantyl)-2H-benzimidazol-2-ylidene (13-10), 1-methyl-3-(2,4,6-trimethylphenyl)-2H-benzimidazol-2-ylidene (13-11), 1,3-bis(2,6-diisopropylphenyl)-2H-imidazol-2-ylidene (13-12), 1,3-bis(2,4,6-trimethylphenyl)-2H-imidazol-2-ylidene (13-13), 1,3-bis[(1S)-2,2-dimethyl-1-(1-naphthyl)propyl]-2H-imidazol-2-ylidene (13-14), 2-(2,6-diisopropylphenyl)-5-methylimidazo[1,5-a]pyridin-1(2H)-ylidene (13-15), 2-(2,4,6-trimethylphenyl)-5-methylimidazo[1,5-a]pyridin-1(2H)-ylidene (13-16) and 2-benzylimidazo[1,5-a]quinolin-1(2H)-ylidene (13-17), etc.

[Formula 26]

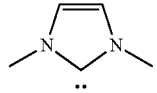
(13-1)

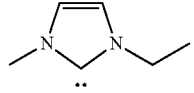
(13-2)

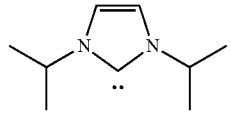
(13-3)

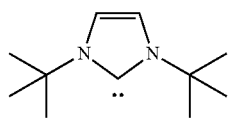
(13-4)

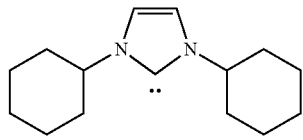
(13-5)

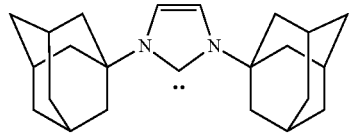
(13-6)

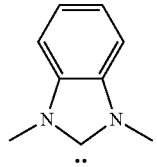
(13-7)

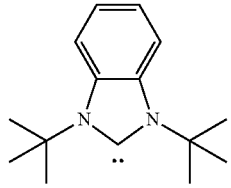
(13-8)

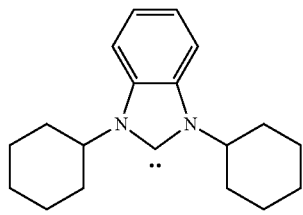
(13-9)

-continued

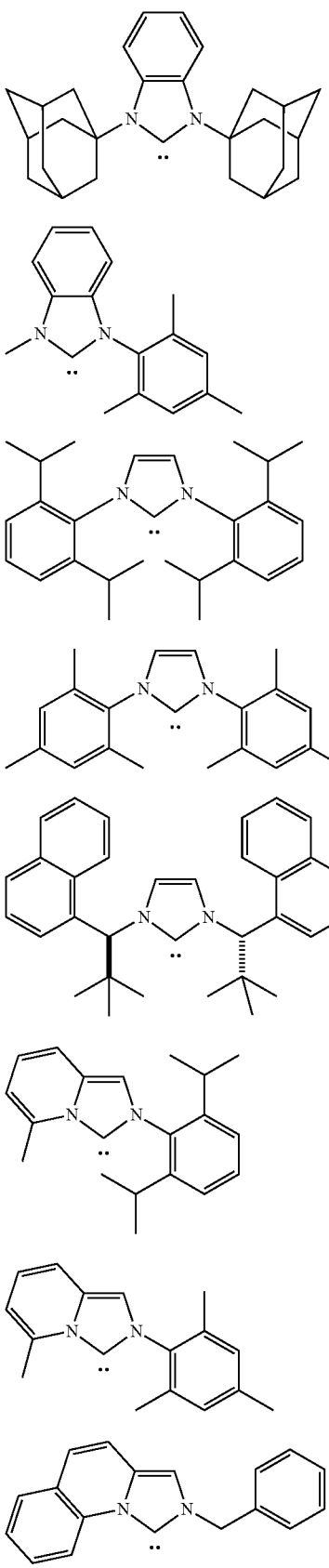

(13-10)
(13-11)
(13-12)
(13-13)
(13-14)
(13-15)
(13-16)
(13-17)

Specific examples of dihydroimidazol-2-ylidene represented by general formula (14) include 1,3-dimethyl-2-imidazolidinylidene (14-1), 1,3-bis(2,4,6-trimethylphenyl)-2-imidazolidinylidene (14-2), 1,3-bis(2,6-diisopropylphenyl)-2-imidazolidinylidene (14-3), 1-(2,6-diisopropylphenyl)-3-(2,4,6-trimethylphenyl)-2-imidazolidinylidene (14-4), 1-(1-adamantyl)-3-(2,4,6-trimethylphenyl)-2-imidazolidinylidene (14-5), 1,3-bis(2,7-diisopropylnaphthalen-1-yl)-2-imidazolidinylidene (14-6), 1,3-bis[(1S)-2,2-dimethyl-1-(1-naphthyl)propyl]-2-imidazolidinylidene (14-7) and 1,3-bis[(1S)-2,2-dimethyl-1-(2-tolyl)propyl]-2-imidazolidinylidene (14-8), etc.

[Formula 27]

(14-1)

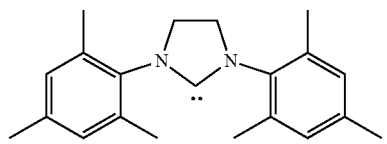

(14-2)

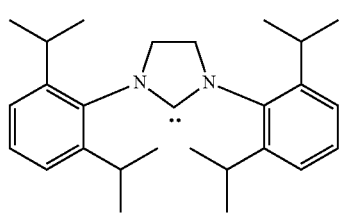

(14-3)

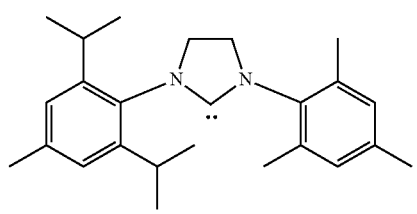

(14-4)

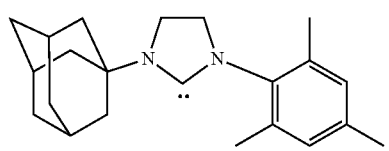

(14-5)

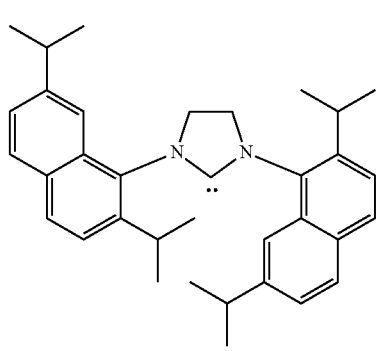

(14-6)

(14-7)

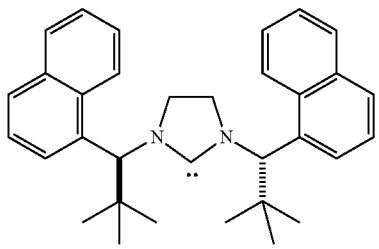

(14-8)

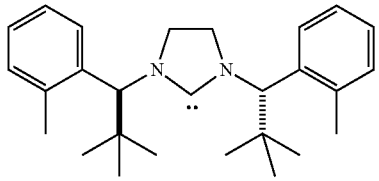

Among the above N-heterocyclic carbenes, some compounds are unstable in air. Thus, for easy handling, these compounds may be reacted with a Bronsted acid, as specifically exemplified by hydrochloric acid, hydrobromic acid, hydroiodic acid and tetrafluoroboric acid, etc., and thereby converted into corresponding Bronsted acid salts. When these Bronsted acid salts are used in the manufacture of the transition metal complex of the present invention, these Bronsted acid salts may be directly used in the reaction, or may be treated with a base outside the reaction system to liberate N-heterocyclic carbenes before use in the reaction, or may be treated with a base within the reaction system to liberate N-heterocyclic carbenes during the reaction.

A detailed explanation will then be made of the correlation between the numerical values represented by k, l and n in the metal complex represented by the above general formula (8) and the structure of the metal complex, by way of the following structural compositional formulae ($8^A$), ($8^B$), ($8^C$), ($8^D$), ($8^E$), ($8^F$), ($8^G$) and ($8^H$) (a structural compositional formula is defined to be a structural formula without consideration of the coordination specificity characteristic of a metal complex having a plurality of ligands). It should be noted that in the following structural compositional formulae ($8^A$) to ($8^H$), G and G' are as defined above in general formula (1), $M^8$, $X^1$, $X^2$, $L^1$ and $L^2$ are as defined above in general formula (8), and each broken line between symbols represents a coordinate bond.

[Formula 28]

($8^A$)

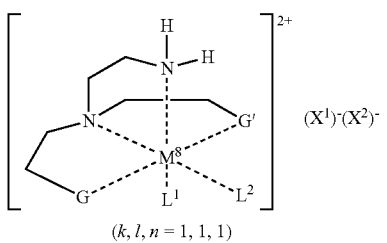

(k, l, n = 1, 1, 1)

($8^B$)

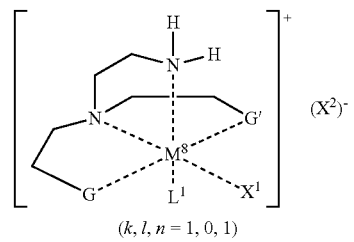

(k, l, n = 1, 0, 1)

($8^C$)

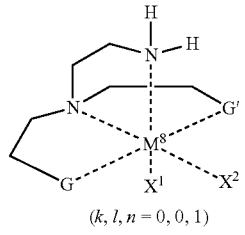

(k, l, n = 0, 0, 1)

($8^D$)

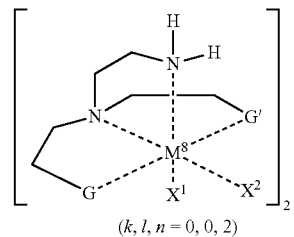

(k, l, n = 0, 0, 2)

($8^E$)

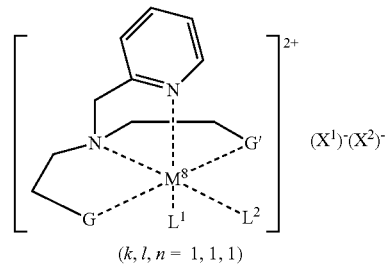

(k, l, n = 1, 1, 1)

($8^F$)

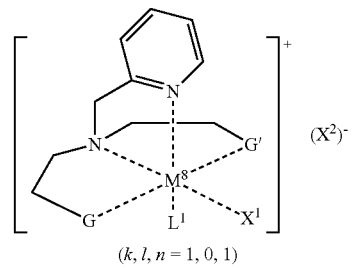

(k, l, n = 1, 0, 1)

($8^G$)

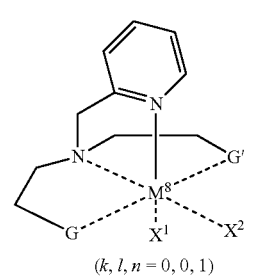

(k, l, n = 0, 0, 1)

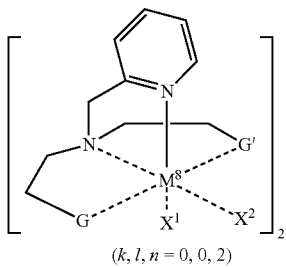

(8^H) (k, l, n = 0, 0, 2)

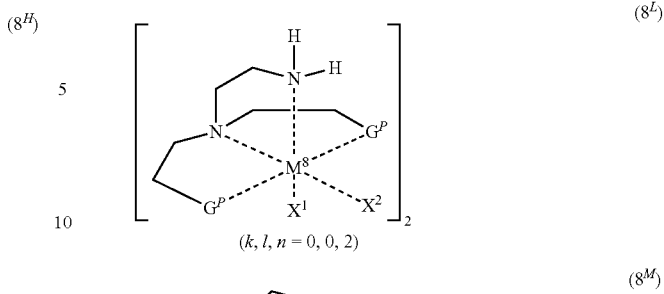

(8^L) (k, l, n = 0, 0, 2)

In the above formulae, the combination of the numerical values represented by k, l and n is expressed as follows: (k, l, n)=((the numerical value of k), (the numerical value of l), (the numerical value of n)). As can be seen from the above structural compositional formulae (8$^A$) to (8$^H$), the above general formula (8) represents a dicationic complex in the case of (k, l, n)=(1, 1, 1), represents a cationic complex in the case of (k, l, n)=(1, 0, 1), and represents a neutral complex in the case of (k, l, n)=(0, 0, 1). Further, the above general formula (8) represents a neutral binuclear complex in the case of (k, l, n)=(0, 0, 2).

Preferred embodiments of the metal complex represented by the above compositional general formula (8) include those of the above structural compositional formulae (8$^A$) to (8$^H$) in which G and G' are each G$^P$, i.e., metal complexes represented by the following structural compositional formulae (8$^I$), (8$^J$), (8$^K$), (8$^L$), (8$^M$), (8$^N$), (8$^O$) and (8$^P$):

[Formula 29]

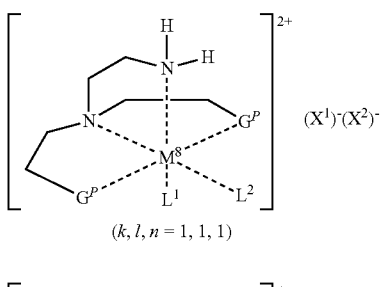

(8$^I$) (k, l, n = 1, 1, 1)

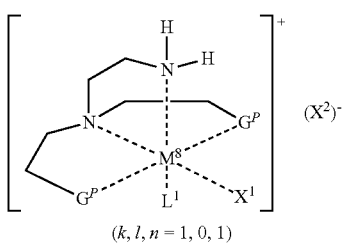

(8$^J$) (k, l, n = 1, 0, 1)

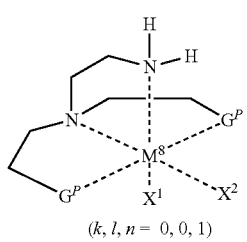

(8$^K$) (k, l, n = 0, 0, 1)

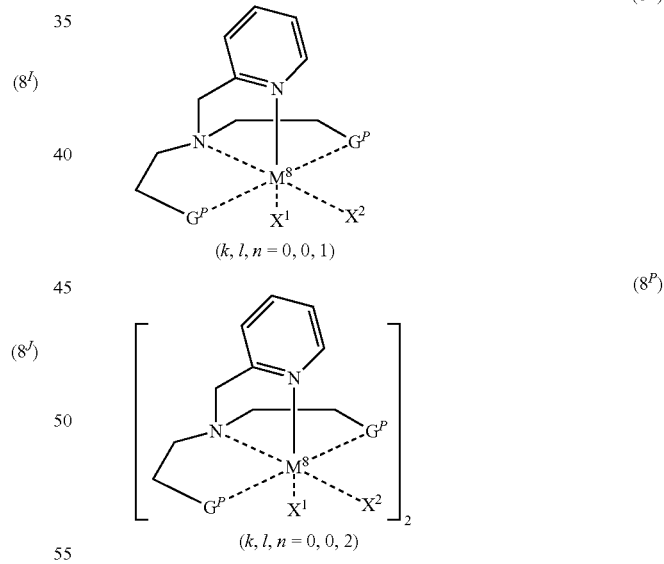

wherein G$^P$, M$^8$, X$^1$, X$^2$, L$^1$ and L$^2$ are as defined above in general formula (8), and each broken line between symbols represents a coordinate bond. It should be noted that G$^P$ appearing twice or more in the same formula may be either the same or different.

More preferred embodiments of the metal complex represented by the above general formula (8) include metal complexes represented by the following structural compositional formulae (8$^Q$), (8$^R$), (8$^S$), (8$^T$), (8$^U$) (8$^V$), (8$^W$) and (8$^X$):

[Formula 30]

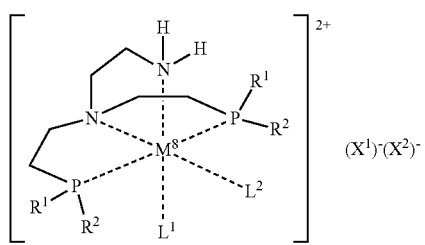 (8<sup>Q</sup>)

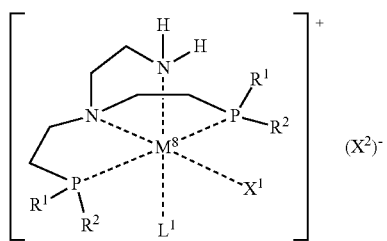 (8<sup>R</sup>)

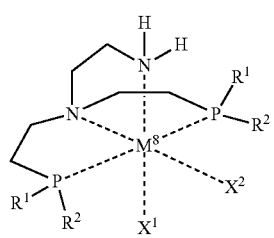 (8<sup>S</sup>)

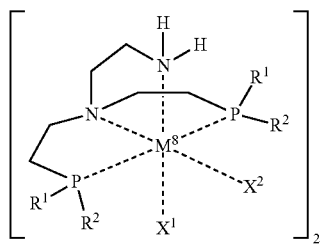 (8<sup>T</sup>)

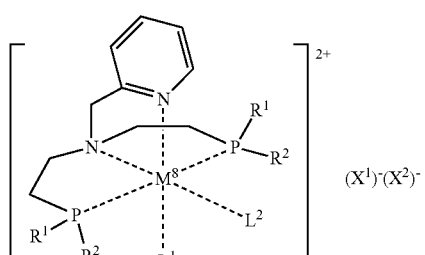 (8<sup>U</sup>)

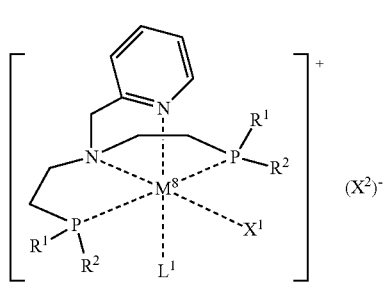 (8<sup>V</sup>)

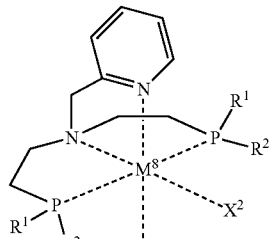 (8<sup>W</sup>)

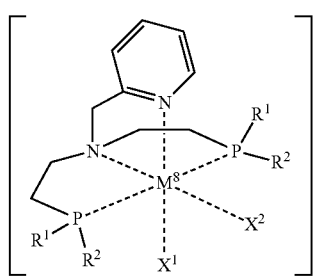 (8<sup>X</sup>)

wherein $M^8$, $X^1$, $X^2$, $L^1$, $L^2$, $R^1$ and $R^2$ are as defined above in general formulae ($G^P$) and (8), and each broken line between symbols represents a coordinate bond. It should be noted that $R^1$ and $R^2$ appearing twice or more in the same formula may be either the same or different.

Particularly preferred embodiments of the metal complex represented by the above general formula (8) include the following structural compositional formulae ($8^Y$), ($8^Z$), ($8^{AA}$), ($8^{AB}$), ($8^{AC}$), ($8^{AD}$), ($8^{AE}$), ($8^{AF}$), ($8^{AG}$), ($8^{AH}$), ($8^{AI}$), ($8^{AJ}$) and ($8^{AK}$)

[Formula 31]

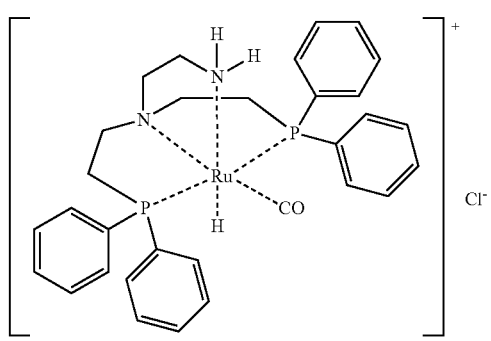 (8<sup>Y</sup>)

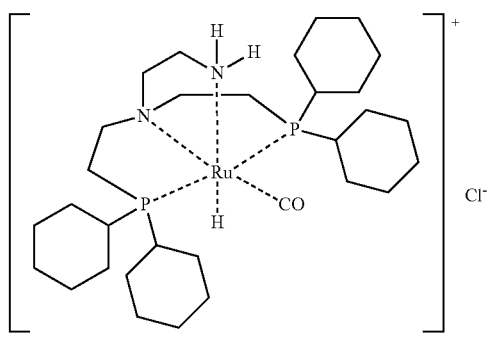 (8<sup>Z</sup>)

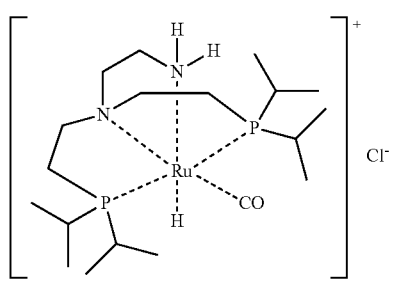 (8^AA)
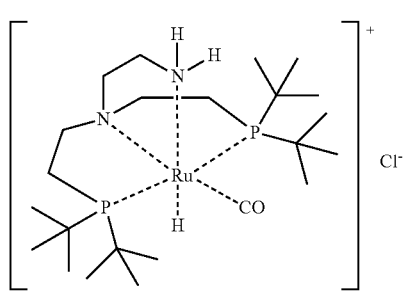 (8^AB)
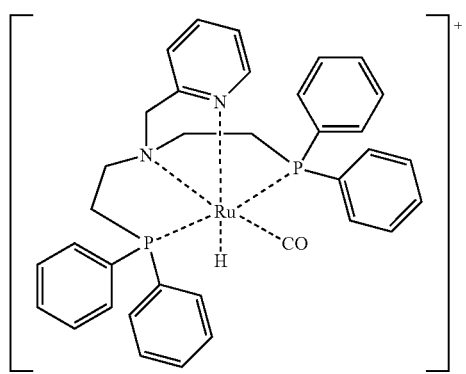 (8^AC)
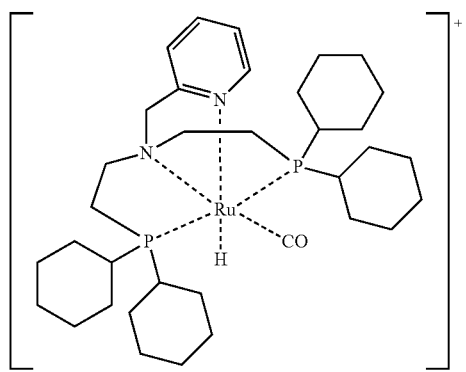 (8^AD)
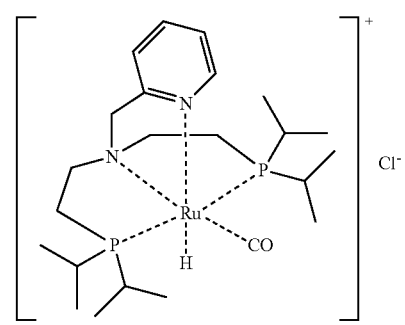 (8^AE)
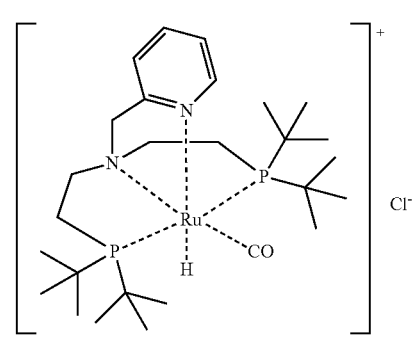 (8^AF)
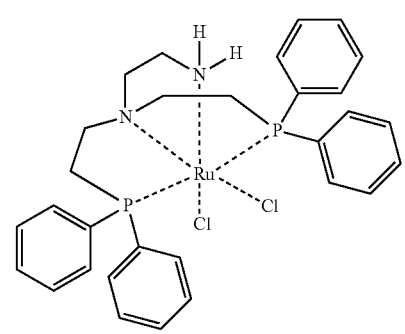 (8^AG)
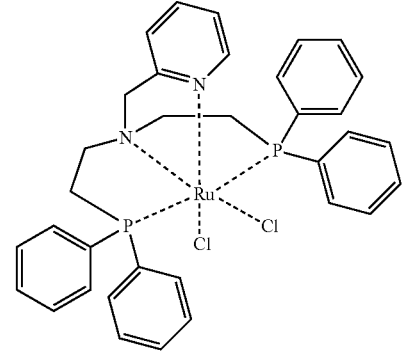 (8^AH)

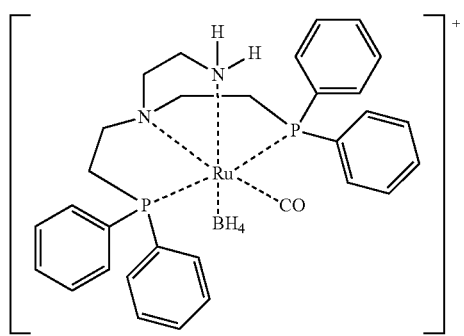

(8^{AI})

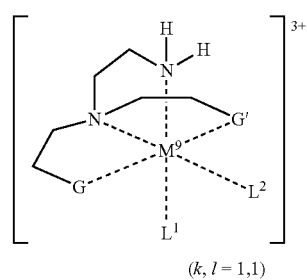

(9^A)

(k, l = 1,1)

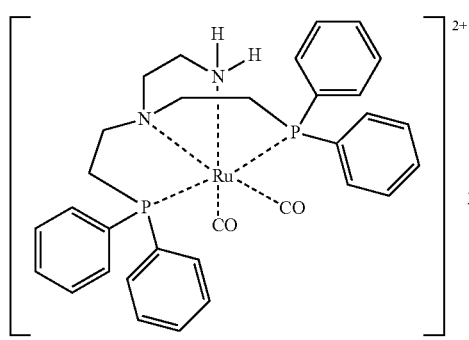

(8^{AJ})

[Formula 32]

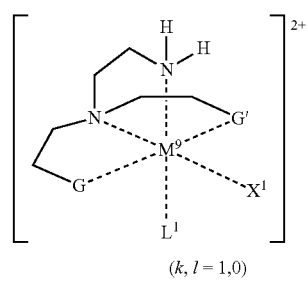

(9^B)

(k, l = 1,0)

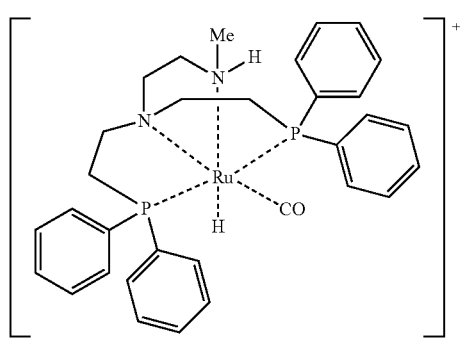

(8^{AK})

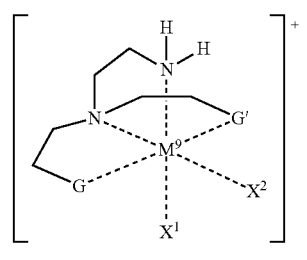

(9^C)

(k, l = 0,0)

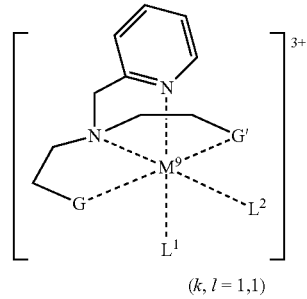

(9^D)

(k, l = 1,1)

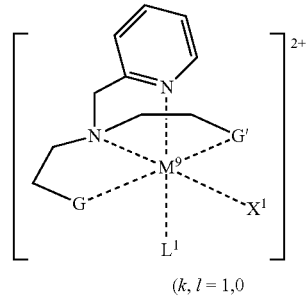

(9^E)

(k, l = 1,0)

An explanation will then be made of the correlation between the numerical values of k and l in the metal complex represented by the above general formula (9) and the structure of the metal complex, by way of the following structural compositional formulae $(9^A)$, $(9^B)$, $(9^C)$, $(9^D)$, $(9^E)$ and $(9^F)$. It should be noted that in the following structural compositional formulae $(9^A)$ to $(9^F)$, G and G' are as defined above in general formula (1), $M^9$, $X^1$, $X^2$, $X^3$, $L^1$ and $L^2$ are as defined above in compositional general formula (9), and each broken line between symbols represents a coordinate bond.

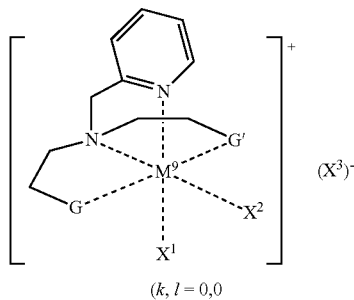

(9^F) (k, l = 0,0)

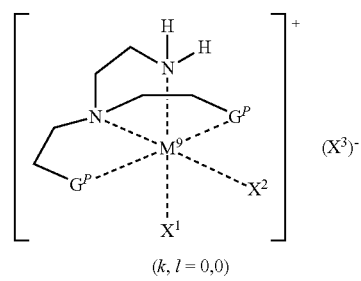

(9^I) (k, l = 0,0)

In the above formulae, the combination of the numerical values represented by k and l is expressed as follows: (k, l)=((the numerical value of k), (the numerical value of l)). As can be seen from the above structural compositional formulae ($9^A$) to ($9^F$), the above general formula (9) represents a tricationic complex in the case of (k, l)=(1, 1) and represents a dicationic complex in the case of (k, l)=(1, 1). Moreover, the above general formula (9) represents a cationic complex in the case of (k, l)=(0, 0).

Preferred embodiments of the metal complex represented by the above general formula (9) include those of the above structural compositional formulae ($9^A$) to ($9^F$) in which G and G' are each G', i.e., metal complexes represented by the following structural compositional formulae ($9^G$), ($9^H$) ($9^I$) ($9^J$) ($9^K$) and ($9^L$):

[Formula 33]

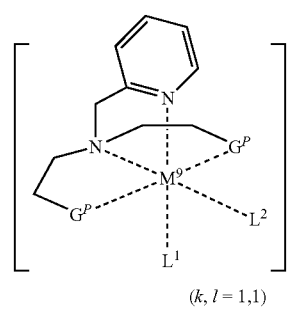

(9^J) (k, l = 1,1)

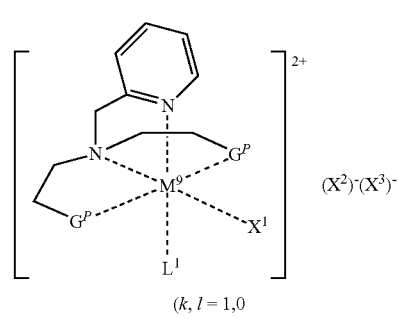

(9^K) (k, l = 1,0)

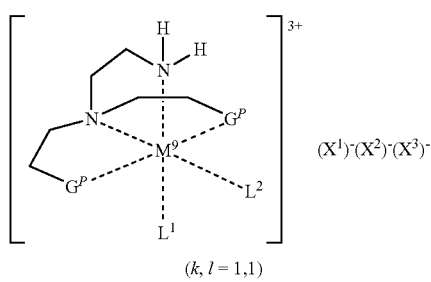

(9^G) (k, l = 1,1)

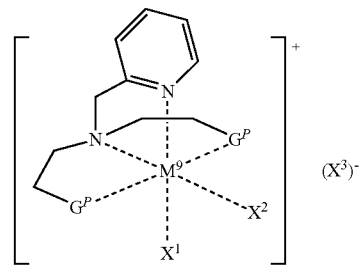

(9^L) (k, l = 0,0)

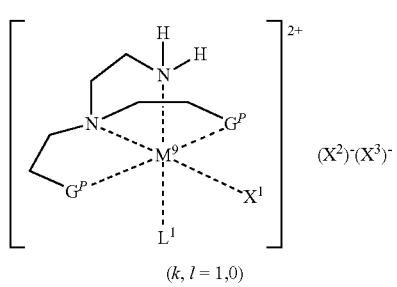

(9^H) (k, l = 1,0)

wherein $G^P$, $M^9$, $X^1$, $X^2$, $L^1$ and $L^2$ are as defined above in general formula (9), and each broken line between symbols represents a coordinate bond. It should be noted that $G^P$ appearing twice or more in the same formula may be either the same or different.

More preferred embodiments of the metal complex represented by the above general formula (9) include metal complexes represented by the following structural compositional formulae ($9^M$), ($9^N$) ($9^O$) ($9^P$) ($9^Q$) and ($9^R$):

[Formula 34]

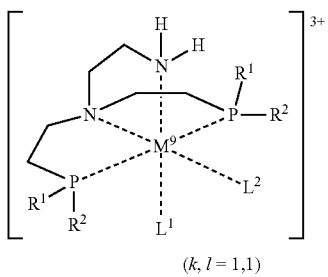 (9$^M$)

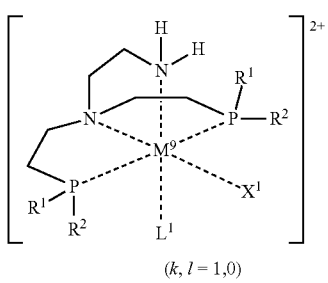 (9$^N$)

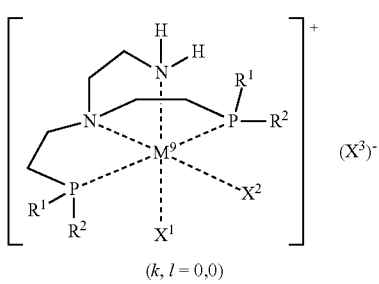 (9$^O$)

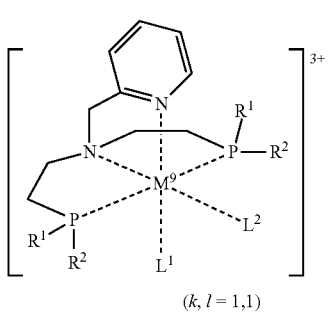 (9$^P$)

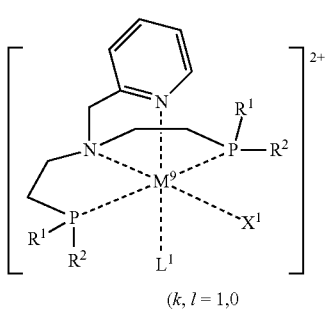 (9$^Q$)

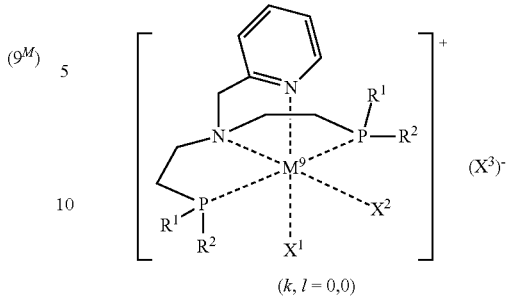 (9$^R$)

wherein $M^9$, $X^1$, $X^2$, $L^1$, $L^2$, $R^1$ and $R^2$ are as defined above in general formulae ($G^P$) and (9), and each broken line between symbols represents a coordinate bond. It should be noted that $R^1$ and $R^2$ appearing twice or more in the same formula may be either the same or different.

An explanation will further be made of the structure of the metal complex represented by the above general formula (10), by way of the following structural compositional formula (10$^A$). It should be noted that in the following structural compositional formula (10$^A$), G and G' are as defined above in general formula (1), $M^{10}$, $X^1$ and $X^2$ are as defined above in compositional general formula (10), and each broken line between symbols represents a coordinate bond.

[Formula 35]

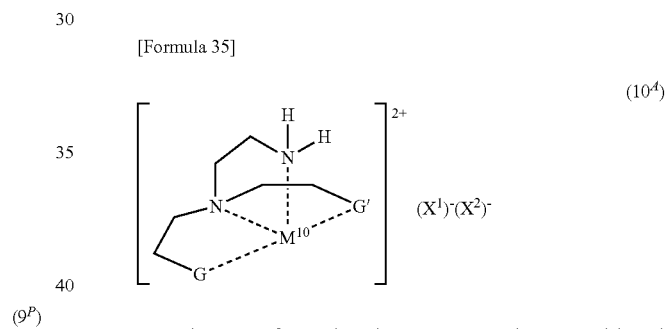 (10$^A$)

As can be seen from the above structural compositional formula (10$^A$), the above general formula (10) represents a dicationic complex.

Preferred embodiments of the metal complex represented by the above general formula (10) include those of structural compositional formula (10$^A$) in which G and G' are each $G^P$, i.e., metal complexes represented by the following structural compositional formula (10$^B$):

[Formula 36]

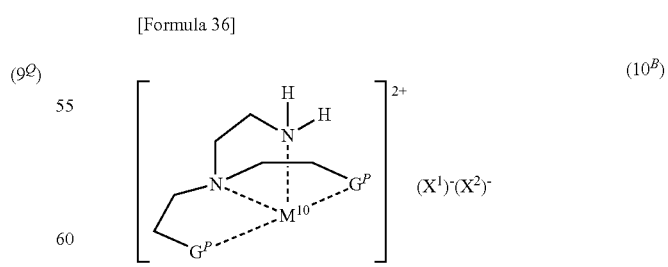 (10$^B$)

wherein $G^P$, $M^{10}$, $X^1$ and $X^2$ are as defined above in general formula (10), and each broken line between symbols represents a coordinate bond. It should be noted that $G^P$ appearing twice or more in the same formula may be either the same or different.

More preferred embodiments of the metal complex represented by the above general formula (8) include metal complexes represented by the following structural compositional formula ($10^C$):

[Formula 37]

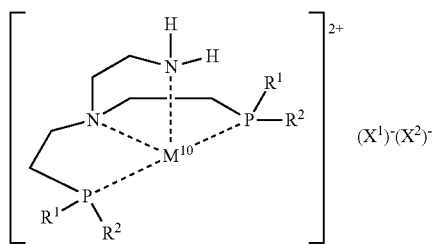

(${10^C}$)

wherein $M^{10}$, $X^1$, $X^2$, $R^1$ and $R^2$ are as defined above in general formulae ($G^P$) and (10), and each broken line between symbols represents a coordinate bond. It should be noted that $R^1$ and $R^2$ appearing twice or more in the same formula may be either the same or different.

An explanation will further be made of the correlation between the numerical values of k and l in the metal complex represented by the above general formula (11) and the structure of the metal complex, by way of the following structural compositional formulae ($11^A$), ($11^B$) ($11^C$) and ($11^D$). It should be noted that in the following structural compositional formulae ($11^A$) to ($11^D$), G and G' are as defined above in general formula (1), X, $L^1$ and $L^2$ are as defined above in compositional general formula (11), and each broken line between symbols represents a coordinate bond.

[Formula 38]

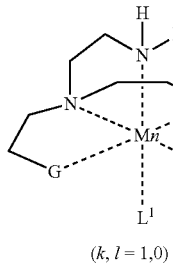

($11^A$)

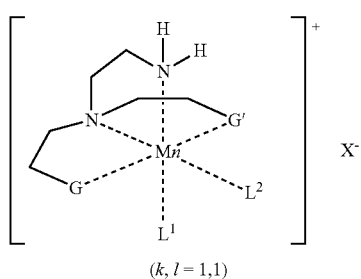

($11^B$)

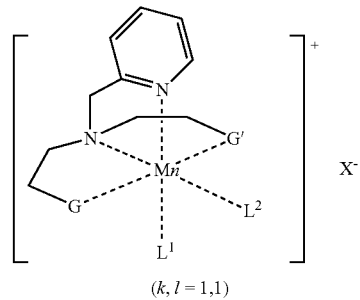

($11^C$)

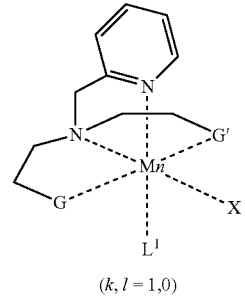

($11^D$)

The combination of the numerical values represented by k and l is expressed as follows: (k, l)=((the numerical value of k), (the numerical value of l)). As can be seen from the above structural compositional formulae ($11^A$) to ($11^D$), the above general formula (11) represents a cationic complex in the case of (k, l)=(1, 1) and represents a neutral complex in the case of (k, l)=(1, 0).

Preferred embodiments of the transition metal complex represented by the above general formula (11) include those of the above structural compositional formulae ($11^A$) to ($11^D$) in which G and G' are each $G^P$, i.e., transition metal complexes represented by the following structural compositional formulae ($11^E$), ($11^F$), ($11^G$) and ($11^H$):

[Formula 39]

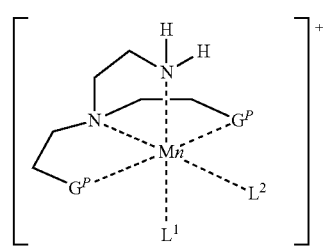

($11^E$)

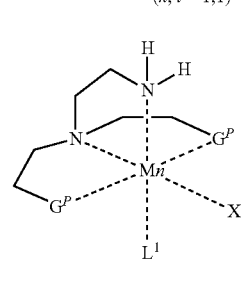

($11^F$)

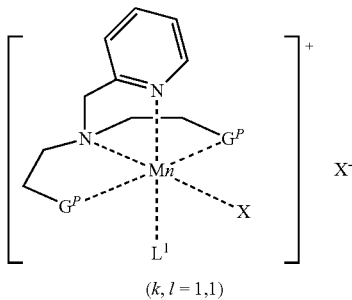

(11^G)

(k, l = 1,1)

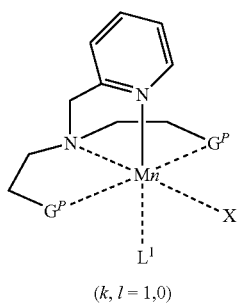

(11^H)

(k, l = 1, 0)

wherein $G^P$, X, $L^1$ and $L^2$ are as defined above in general formula (11), and each broken line between symbols represents a coordinate bond. It should be noted that $G^P$ appearing twice or more in the same formula may be either the same or different.

More preferred embodiments of the transition metal complex represented by the above general formula (11) include metal complexes represented by the following structural compositional formulae (11^I), (11^J), (11^K) and (11^L):

[Formula 40]

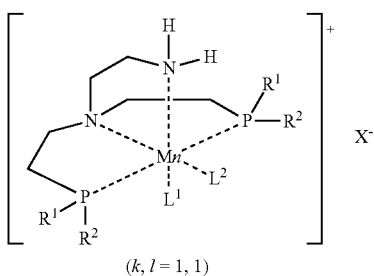

(11^I)

(k, l = 1, 1)

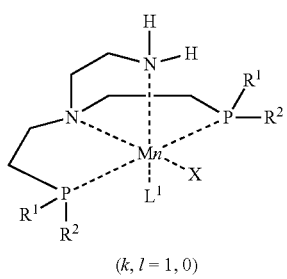

(11^J)

(k, l = 1, 0)

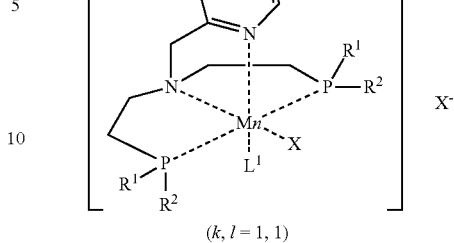

(11^K)

(k, l = 1, 1)

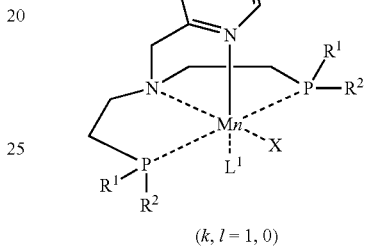

(11^L)

(k, l = 1, 0)

wherein X, $L^1$, $L^2$, $R^1$ and $R^2$ are as defined above in general formulae ($G^P$) and (11), and each broken line between symbols represents a coordinate bond. It should be noted that $R^1$ and $R^2$ appearing twice or more in the same formula may be either the same or different.

It should be noted that due to the coordination effect of metal species, the transition metal complex of the present invention is deprotonated upon treatment with a base, so that the coordinate bond between metal atom and nitrogen atom is converted into a covalent bond in some cases. In more detail, an explanation will be made by taking the case of a transition metal complex represented by the following structural compositional formula (8^B') (wherein each broken line between symbols, G, $M^8$, $X^1$ and $L^1$ are as defined above in structural compositional formula (8^B)) formed upon deprotonation of the transition metal complex (8^B) of the present invention (see scheme (Eq. 1) shown below). The thus deprotonated transition metal complex of the present invention is also very important as an active intermediate in catalytic organic synthesis reactions.

[Formula 41]

Eq. 1

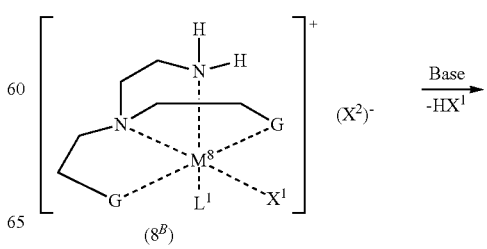

(8^B)

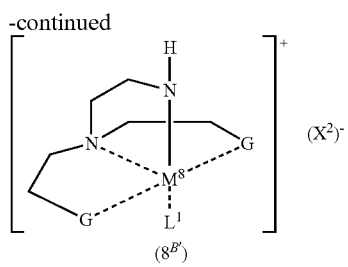

The manufacture of the transition metal complex of the present invention is desirably accomplished in the presence of a solvent. Any solvent may be used for this purpose as long as it does not inhibit the coordinating action of the compound (1) of the present invention, but preferred examples include toluene and tetrahydrofuran, etc. These solvents may each be used alone, or two or more of them may be used in combination as appropriate. The reaction between the compound (1) of the present invention and a transition metal compound may optionally be conducted in the presence of an acid and a base and/or under an inert gas atmosphere such as nitrogen or argon.

The thus obtained transition metal complex of the present invention may optionally be worked up, isolated and purified. Examples of work-up techniques include concentration, solvent replacement, washing, extraction and filtration, etc., and these work-up techniques may be used either alone or in combination. Examples of purification and isolation techniques include decolorization with an adsorbent, column chromatography, crystallization and sublimation, etc., and these techniques may be used either alone or in combination.

It should be noted that when the transition metal complex of the present invention is used as a catalyst in organic synthesis reactions, the transition metal complex of the present invention may be used without being isolated from the reaction mixture between the compound (1) of the present invention and a transition metal compound, or may be used after being optionally treated by the above work-up, isolation and purification techniques, which may each be used alone, or two or more of which may be used in combination as appropriate. Further, the compound (1) of the present invention and a transition metal compound may be directly added into organic synthesis reaction systems to thereby prepare the transition metal complex of the present invention simultaneously with effecting organic synthesis reactions catalyzed by this complex. Moreover, the transition metal complex of the present invention may undergo various chemical transformations including anion exchange reaction before use as a catalyst in organic synthesis reactions.

It should be noted that the compound of the present invention is useful as a tetradentate ligand in various catalytic organic synthesis reactions, and the transition metal complex of the present invention is useful as a catalyst in various organic synthesis reactions. These organic synthesis reactions are not limited in any way, but specific examples include oxidation reaction, reduction reaction, hydrogenation reaction, dehydrogenation reaction, hydrogen transfer reaction, addition reaction, conjugate addition reaction, cyclization reaction, functional group transformation reaction, isomerization reaction, rearrangement reaction, polymerization reaction, bond forming reaction and bond breaking reaction, etc., with hydrogenation reaction being preferred and with hydrogenation reaction of esters being more preferred.

When the compound of the present invention is used as a ligand in catalytic organic synthesis reactions, the compound of the present invention may be added to these reaction systems in any manner, but the compound of the present invention and a metal compound may each be added alone into the reaction systems, or may be added into the reaction systems as a mixture containing the compound of the present invention and the metal compound (and a solvent), or may be added into the reaction systems as a solution containing the transition metal complex of the present invention obtained by reacting the compound of the present invention with the metal compound (optionally together with a monovalent anionic monodentate ligand source as discussed above, a neutral monodentate ligand as discussed above, and a neutral monodentate ligand equivalent such as a Bronsted acid salt of a N-heterocyclic carbene) in a solvent. In these addition embodiments, the above monovalent anionic monodentate ligand source, the above neutral monodentate ligand and the above neutral monodentate ligand equivalent may be added separately so as to adjust catalytic activity and reaction selectivity. Moreover, the compounds of the present invention may each be used alone, or two or more of them may be used in combination as appropriate. When the transition metal complex of the present invention is used as a catalyst in organic synthesis reactions, the transition metal complex of the present invention may be added to these reaction systems in any manner, but the transition metal complex of the present invention may be added alone into the reaction systems, or the transition metal complex of the present invention may be dissolved or suspended in a solvent before being added into the reaction systems. In these addition embodiments, the compound of the present invention, the above monovalent anionic monodentate ligand source, the above neutral monodentate ligand and the above neutral monodentate ligand equivalent may be added separately so as to adjust catalytic activity and reaction selectivity. Moreover, the transition metal complexes of the present invention may each be used alone, or two or more of them may be used in combination as appropriate.

Subsequently, an explanation will be made of a method for manufacturing alcohols by hydrogenation reduction of ketones.

Such a method for manufacturing alcohols by hydrogenation reduction of ketones in the present invention is a method for manufacturing alcohols from ketones using the ruthenium complex represented by general formula (8) and a hydrogen donor, as exemplified by a method as shown in the following scheme (Eq. 2):

[Formula 42]

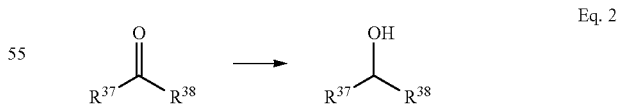

In scheme (Eq. 2), $R^{37}$ and $R^{38}$ are each independently selected from a hydrogen atom, an alkyl group, an aryl group, an aralkyl group, an alkenyl group, an alkynyl group, a heteroaryl group, or a keto group represented by the following general formula (15). Alternatively, $R^{37}$ and $R^{38}$ may be joined together to form a ring together with their adjacent carbon atom. Moreover, these alkyl, aryl, aralkyl, alkenyl, alkynyl and heteroaryl groups are optionally substituted.

An explanation will be made of $R^{37}$ and $R^{38}$ in scheme (Eq. 2). The alkyl, aryl, aralkyl, alkenyl, alkynyl and heteroaryl groups intended here include an alkyl group, an aryl group, an aralkyl group, an alkenyl group, an alkynyl group and a heteroaryl group as discussed above for $R^1$ and $R^2$ in the explanation of general formula $(G^P)$.

Examples of a keto group include those represented by the following general formula (15):

[Formula 43]

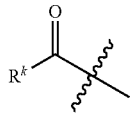

(15)

In general formula (15), $R^k$ represents a hydrogen atom, an alkyl group, an aryl group, an aralkyl group, an alkenyl group, an alkynyl group, or a heteroaryl group. Moreover, these alkyl, aryl, aralkyl, alkenyl, alkynyl and heteroaryl groups are optionally substituted.

The alkyl, aryl, aralkyl, alkenyl, alkynyl and heteroaryl groups intended in $R^k$ include an alkyl group, an aryl group, an aralkyl group, an alkenyl group, an alkynyl group and a heteroaryl group as discussed above for $R^1$ and $R^2$ in the explanation of general formula $(G^P)$, and when these groups have substituents, examples include an alkyl group, an aryl group, an aralkyl group, an alkenyl group, an alkynyl group, an alkyloxy group, an aryloxy group, an aralkyloxy group, a heteroaryl group, an amino group, a halogen atom, a silyl group, an optionally protected hydroxyl group and an amino group as discussed above for $R^1$ and $R^2$ in general formula $(G^P)$. Moreover, they may have the keto group represented by general formula (15) as a substituent.

When $R^{37}$ and/or $R^{38}$ is a keto group or has a keto group as a substituent, a polyhydric alcohol is obtained as a product.

In scheme (Eq. 2), when $R^{37}$ and $R^{38}$ are joined together to form a ring, such a ring is exemplified by those as discussed above in the explanation of general formula (G') where $R^1$ and $R^2$ are joined together to form a ring.

Hydrogenation reaction from ketones into alcohols in the present invention may be accomplished preferably in the absence or presence of a solvent, but it is preferable to use a solvent. Solvents preferred for use are those in which a substrate can be dissolved, and a single solvent or a mixed solvent is used for this purpose. Specific examples include aromatic hydrocarbons (e.g., toluene, xylene), aliphatic hydrocarbons (e.g., hexane, heptane), halogenated hydrocarbons (e.g., methylene chloride, chlorobenzene), ethers (e.g., diethyl ether, tetrahydrofuran, methyl tert-butyl ether, cyclopentyl methyl ether), alcohols (e.g., methanol, ethanol, isopropyl alcohol, n-butyl alcohol, 2-butanol, tert-butyl alcohol), and polyhydric alcohols (e.g., ethylene glycol, propylene glycol, 1,2-propanediol and glycerin).

The amount of such a solvent to be used may be selected as appropriate depending on the reaction conditions, etc. The reaction may optionally be conducted under stirring conditions.

Examples of a hydrogen donor available for use in the method of the present invention include a hydrogen gas, formic acid, a primary alcohol (e.g., methanol, ethanol, butanol) and a secondary alcohol (e.g., isopropanol), etc. Preferred are a hydrogen gas and a secondary alcohol.

The amount of the catalyst to be used will vary depending on the type of substrate, the reaction conditions and/or the type of catalyst, etc. However, it is usually in the range of 0.0001 mol % to 10 mol %, preferably in the range of 0.005 mol % to 5 mol %, expressed as a molar ratio of ruthenium metal to the substrate.

The reaction temperature is 0° C. to 200° C., preferably 30° C. to 150° C. If the reaction temperature is too low, unreacted starting materials may remain in abundance. If the reaction temperature is too high, the starting materials, catalyst and others may be decomposed. Such too high and too low temperatures are not desirable.

The pressure of a hydrogen gas during hydrogenation reduction is 0.1 MPa to 10 MPa, preferably 3 MPa to 6 MPa.

The reaction time is 30 minutes to 72 hours, preferably 2 hours to 48 hours, which is sufficient to obtain a reaction product with a high starting material conversion rate.

After completion of the reaction, commonly used purification techniques such as extraction, filtration, crystallization, distillation, and various types of chromatography may be used alone or in combination, as appropriate, to obtain a desired product.

During hydrogenation reduction of ketones in the present invention, additives may be added as appropriate. Examples of additives include basic compounds and metal hydride reagents, etc.

Specific examples of basic compounds include amines such as triethylamine, diisopropylethylamine, N,N-dimethylaniline, piperidine, pyridine, 4-dimethylamino-pyridine, 1,5-diazabicyclo[4.3.0]non-5-ene, 1,8-diazabicyclo[5.4.0]undec-7-ene, tri-n-butylamine and N-methylmorpholine, etc.; alkali metal carbonates such as potassium carbonate, sodium carbonate, lithium carbonate, cesium carbonate, etc.; alkaline earth metal carbonates such as magnesium carbonate, calcium carbonate, etc.; alkali metal bicarbonates such as sodium bicarbonate, potassium bicarbonate, etc.; alkali metal hydroxides such as sodium hydroxide, potassium hydroxide, lithium hydroxide, etc.; alkaline earth metal hydroxides such as magnesium hydroxide, calcium hydroxide, etc.; alkali metal alkoxides such as sodium methoxide, sodium ethoxide, sodium isopropoxide, sodium tert-butoxide, potassium methoxide, potassium ethoxide, potassium isopropoxide, potassium tert-butoxide, lithium methoxide, lithium isopropoxide, lithium tert-butoxide, etc.; alkaline earth metal alkoxides such as magnesium methoxide, magnesium ethoxide, etc.; and metal hydrides such as sodium hydride, calcium hydride, etc. A particularly preferred base is sodium methoxide or potassium tert-butoxide.

Examples of metal hydride reagents include lithium borohydride, sodium borohydride, potassium borohydride, lithium aluminum hydride and so on.

In addition, NHC and derivatives thereof may be added as additives. Even when used in an amount of 10 mol % or less relative to the substrate, these additives are sufficient to give a high conversion rate.

Subsequently, an explanation will be made of a method for manufacturing alcohols, aldehydes or hemiacetals by hydrogenation reduction of esters.

Such a method for manufacturing alcohols, aldehydes or hemiacetals by hydrogenation reduction of esters in the present invention may be exemplified by a method for manufacturing alcohols from esters as shown in the following scheme (Eq. 3):

[Formula 44]

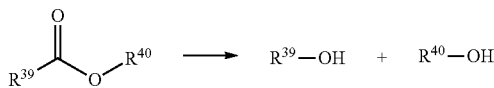

Eq. 3

In scheme (Eq. 3), $R^{39}$ and $R^{40}$ are each independently selected from an alkyl group, an aryl group, an aralkyl group, an alkenyl group, an alkynyl group, a heteroaryl group, or a keto group represented by general formula (15) as discussed above, provided that $R^{39}$ may also be hydrogen, and alkyl, aryl, aralkyl, alkenyl, alkynyl and heteroaryl groups are optionally substituted. Alternatively, $R^{39}$ and $R^{40}$ may be joined together to form a ring together with their adjacent atoms.

An explanation will be made of $R^{39}$ and $R^{40}$ in scheme (Eq. 3). The alkyl, aryl, aralkyl, alkenyl, alkynyl and heteroaryl groups represented by $R^{39}$ and $R^{40}$ include an alkyl group, an aryl group, an aralkyl group, an alkenyl group, an alkynyl group and a heteroaryl group as discussed above for $R^1$ and $R^2$ in the explanation of general formula ($G^P$).

Moreover, substituents which may be substituted on $R^{39}$ and $R^{40}$ in scheme (Eq. 3) include an alkyl group, an aryl group, an aralkyl group, an alkenyl group, an alkynyl group, an alkyloxy group, an aryloxy group, an aralkyloxy group, a halogen atom, a silyl group, a heteroaryl group, an optionally protected hydroxyl group and an amino group as discussed above for $R^1$ and $R^2$ in the explanation of general formula (Eq. 2), as well as a keto group as discussed above in the explanation of $R^{37}$ and $R^{38}$ in scheme (Eq. 2), an alkoxycarbonyl group, an aryloxycarbonyl group, an aralkyloxycarbonyl group, an alkenyloxy group and an alkynyloxy group. However, if the protective group in the optionally protected hydroxyl group is an acyl group, the protective group may be reduced in the resulting products in some cases. Moreover, when $R^{39}$ and/or $R^{40}$ is a keto group or has a keto group, an alkoxycarbonyl group, an aryloxycarbonyl group, an aralkyloxycarbonyl group, an alkenyloxycarbonyl group or an alkynyloxycarbonyl group as a substituent, these groups may be hydrogenated and reduced in the resulting polyhydric alcohols in some cases.

Examples of an alkoxycarbonyl group, an aryloxycarbonyl group, an aralkyloxycarbonyl group, an alkenyloxycarbonyl group and an alkynyloxycarbonyl group, each serving as a substituent, include those represented by the following general formula (16):

[Formula 45]

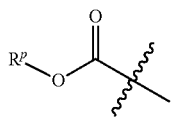

(16)

In general formula (16), R represents an alkyl group, an aryl group, an aralkyl group, an alkenyl group, an alkynyl group, or a heteroaryl group. Moreover, these alkyl, aryl, aralkyl, alkenyl, alkynyl and heteroaryl groups are optionally substituted.

An explanation will be made of $R^P$ in general formula (16). The alkyl, aryl, aralkyl, alkenyl, alkynyl and heteroaryl groups intended here include an alkyl group, an aryl group, an aralkyl group, an alkenyl group, an alkynyl group and a heteroaryl group as discussed above for $R^1$ and $R^2$ in the explanation of general formula ($G^P$).

Substituents which may be substituted on $R^P$ in general formula (16) include an alkyl group, an aryl group, an aralkyl group, an alkenyl group, an alkynyl group and a heteroaryl group as discussed above for $R^1$ and $R^2$ in general formula ($G^P$).

Moreover, in scheme (Eq. 3), when $R^{39}$ and $R^{40}$ are joined together to form a ring, such a ring is exemplified by those as discussed above in the explanation of general formula ($G^P$) where $R^1$ and $R^2$ are joined together to form a ring, and the ester compound appearing in scheme (Eq. 3) is a lactone in this case. Moreover, when the ester compound is a lactone, its reduction product is a polyhydric alcohol in which $R^{39}$ and $R^{40}$ are joined together.

Hydrogenation reduction from esters into alcohols, aldehydes or hemiacetals in the present invention may be accomplished preferably in the absence or presence of a solvent, but it is preferable to use a solvent. The type and amount of solvent to be used may be those as discussed above for hydrogenation reduction from ketones into alcohols.

Examples of a hydrogen donor include the same hydrogen donors as discussed above for hydrogenation reduction from ketones into alcohols.

Likewise, the amount of the catalyst to be used, the reaction temperature, the pressure of hydrogen during hydrogenation reduction, and the reaction time may be those as discussed above for hydrogenation reduction from ketones into alcohols.

After completion of the reaction, commonly used purification techniques such as extraction, filtration, crystallization, distillation, and various types of chromatography may be used alone or in combination, as appropriate, to obtain a desired product.

During hydrogenation reduction of esters, additives may also be added as appropriate, as in the case of hydrogenation reduction of ketones, and examples of additives include the same additives as discussed above for hydrogenation reduction from ketones into alcohols.

Subsequently, an explanation will be made of a method for manufacturing alcohols, aldehydes, hemiaminals or amines by hydrogenation reduction of amides.

Such a method for manufacturing alcohols, aldehydes, hemiaminals or amines by hydrogenation reduction of amides in the present invention may be exemplified by a method starting from amide compounds to manufacture corresponding alcohols and/or amines as shown in the following scheme (Eq. 4):

[Formula 46]

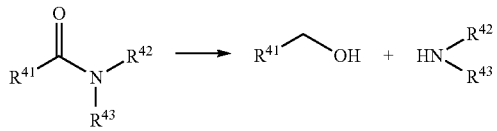

Eq. 4

In scheme (Eq. 4), $R^{41}$ represents a hydrogen atom, an alkyl group, an aryl group, an aralkyl group, a heteroaryl group, an alkenyl group or an alkynyl group, and these alkyl, aryl, aralkyl, heteroaryl, alkenyl and alkynyl groups are optionally substituted. $R^{42}$ and $R^{43}$ are each independently selected from a hydrogen atom, an alkyl group, an aryl group, an aralkyl group, an alkenyl group, an alkynyl group, a heteroaryl group, an alkyloxy group, an aryloxy group, an aralkyloxy group, an alkoxycarbonyl group, an aryloxycarbonyl group, an aralkyloxycarbonyl group, an alkenyloxycarbonyl group or an alkynyloxycarbonyl group, and these alkyl, aryl, aralkyl, alkenyl, alkynyl, heteroaryl, alkyloxy, aryloxy, aralkyloxy, alkoxycarbonyl, aryloxycarbonyl, aralkyloxycarbonyl, alkenyloxycarbonyl and alkynyloxycarbonyl groups are optionally substituted. Further, $R^{41}$ and $R^{42}$ and/or $R^{43}$, or $R^{42}$ and $R^{43}$ may be joined together to a form ring.

An explanation will be made of $R^{41}$, $R^{42}$ and $R^{43}$ in scheme (Eq. 4). The alkyl, aryl, aralkyl, alkenyl, alkynyl and heteroaryl groups intended in $R^{41}$ include an alkyl group, an aryl group, an aralkyl group, an alkenyl group, an alkynyl group and a heteroaryl group as discussed above in the explanation of $R^1$ and $R^2$ in general formula ($G^P$). Substituents which may be substituted on these alkyl, aryl, aralkyl, alkenyl, alkynyl and heteroaryl groups include an alkyl group, an aryl group, an aralkyl group, an alkenyl group, an alkynyl group, an alkyloxy group, an aryloxy group, an aralkyloxy group, a halogen atom, a silyl group, a heteroaryl group and an optionally protected hydroxyl group, etc., and an amino group as discussed above in the explanation of $R^1$ and $R^2$ in general formula ($G^P$), a keto group as discussed above in the explanation of $R^K$ in general formula (15), as well as an alkoxycarbonyl group, an aryloxycarbonyl group, an aralkyloxycarbonyl group and an alkenyloxy group as discussed above in the explanation of $R^{39}$ and $R^{40}$ in scheme (Eq. 3). If the protective group in the optionally protected hydroxyl group is an acyl group, the protective group may be detached from the resulting products in some cases. Moreover, when $R^{41}$ has a keto group, an alkoxycarbonyl group, an aryloxycarbonyl group, an aralkyloxycarbonyl group, an alkenyloxycarbonyl group or an alkynyloxycarbonyl group as a substituent, these groups may be hydrogenated and reduced in the resulting products in some cases.

The alkyl, aryl, aralkyl, alkenyl, alkynyl, alkyloxy, aryloxy, aralkyloxy and heteroaryl groups intended in $R^{42}$ and $R^{43}$ include an alkyl group, an aryl group, an aralkyl group, an alkenyl group, an alkynyl group, an alkyloxy group, an aryloxy group, an aralkyloxy group and a heteroaryl group as discussed above in the explanation of $R^1$ and $R^2$ in general formula ($G^P$). Substituents which may be substituted on these alkyl, aryl, aralkyl, alkenyl, alkynyl, alkyloxy, aryloxy, aralkyloxy and heteroaryl groups include an alkyl group, an aryl group, an aralkyl group, an alkenyl group, an alkynyl group, an alkyloxy group, an aryloxy group, an aralkyloxy group, a halogen atom, a silyl group, a heteroaryl group, an optionally protected hydroxyl group, etc., and an amino group as discussed above in the explanation of $R^1$ and $R^2$ in general formula ($G^P$), a keto group as discussed above in the explanation of $R^K$ in general formula (15), as well as an alkoxycarbonyl group, an aryloxycarbonyl group, an aralkyloxycarbonyl group, an alkenyloxy group and an alkynyloxy group as discussed above in the explanation of $R^{39}$ and $R^{40}$ in scheme (Eq. 3). However, if the protective group in the optionally protected hydroxyl group is an acyl group, the protective group may be detached from the resulting products in some cases. Moreover, when $R^{42}$ and/or $R^{43}$ has a keto group, an alkoxycarbonyl group, an aryloxycarbonyl group, an aralkyloxycarbonyl group, an alkenyloxycarbonyl group or an alkynyloxycarbonyl group as a substituent, these groups may be hydrogenated and reduced in the resulting products in some cases.

Moreover, in scheme (Eq. 4), when $R^{42}$ and $R^{43}$, or $R^{41}$ and $R^{42}$ and/or $R^{43}$ in the amide compound are joined together to form a ring, such a ring is exemplified by those as discussed above in the explanation of general formula ($G^P$) where $R^1$ and $R^2$ are joined together to form a ring. When $R^{41}$ and $R^{42}$ and/or $R^{43}$ are joined together to form a ring, the amide compound appearing in scheme (Eq. 4) is a lactam. Moreover, when the amide compound is a lactam, its reduction product is an amino alcohol in which $R^{41}$ and $R^{42}$ and/or $R^{43}$ are joined together.

Hydrogenation reduction from amides into alcohols, aldehydes, hemiaminals or amines in the present invention may be accomplished preferably in the absence or presence of a solvent, but it is preferable to use a solvent. The type and amount of solvent to be used may be those as discussed above for hydrogenation reduction from ketones into alcohols.

Examples of a hydrogen donor include the same hydrogen donors as discussed above for hydrogenation reduction from ketones into alcohols.

Likewise, the amount of the catalyst to be used, the reaction temperature, the pressure of hydrogen during hydrogenation reduction, and the reaction time may be those as discussed above for hydrogenation reduction from ketones into alcohols.

After completion of the reaction, commonly used purification techniques such as extraction, filtration, crystallization, distillation, and various types of chromatography may be used alone or in combination, as appropriate, to obtain a desired product.

During hydrogenation reduction of amides, additives may also be added as appropriate, as in the case of hydrogenation reduction of ketones, and examples of additives include the same additives as discussed above for hydrogenation reduction from ketones into alcohols.

An explanation will be made of a method for manufacturing carbonyl compounds by oxidation of alcohols (i.e., a method for manufacturing carbonyl compounds, which comprises dehydrogenation of alcohols), a method for manufacturing carbonyl compounds, which comprises dehydrogenation of hemiacetals, or a method for manufacturing carbonyl compounds, which comprises dehydrogenation of hemiaminals.

Such a method for manufacturing carbonyl compounds in the present invention is as shown in the following scheme (Eq. 5), (Eq. 6) or (Eq. 7):

[Formula 47]

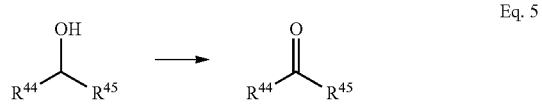

Eq. 5

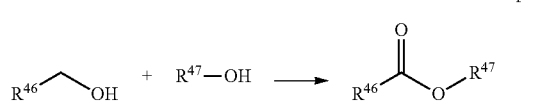

Eq. 6

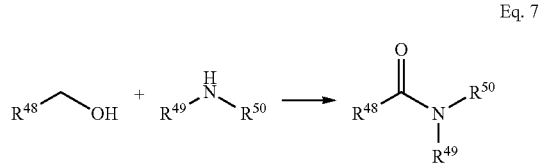

Eq. 7

In schemes (Eq. 5), (Eq. 6) and (Eq. 7), $R^{44}$, $R^{45}$, $R^{46}$, $R^{47}$ and $R^{48}$ are each independently selected from a hydrogen atom, an alkyl group, an aryl group, an aralkyl group, an alkenyl group, an alkynyl group, an alkyloxy group, an aryloxy group, an aralkyloxy group, a heteroaryl group, a keto group, an alkoxycarbonyl group, an aryloxycarbonyl group, an aralkyloxycarbonyl group, an alkenyloxycarbonyl group or an alkynyloxycarbonyl group, and preferably selected from a hydrogen atom, an alkyl group, an aryl group, an aralkyl group, an alkenyl group, an alkynyl group or a heteroaryl group. These alkyl, aryl, aralkyl, alkenyl, alkynyl, alkyloxy, aryloxy, aralkyloxy, heteroaryl, keto, alkoxycarbonyl, aryloxycarbonyl, aralkyloxycarbonyl, alkenyloxycarbonyl and alkynyloxycarbonyl groups are optionally substituted.

$R^{49}$ and $R^{50}$ are each independently selected from a hydrogen atom, an alkyl group, an aryl group, an aralkyl group, an alkenyl group, an alkynyl group, an alkyloxy group, an aryloxy group, an aralkyloxy group or a heteroaryl group, and these alkyl, aryl, aralkyl, alkenyl, alkynyl, alkyloxy, aryloxy, aralkyloxy and heteroaryl groups are optionally substituted.

Moreover, $R^{44}$ and $R^{45}$ in the reaction product appearing in scheme (Eq. 5) may be joined together to form a ring. Likewise, $R^{46}$ and $R^{47}$ in the reaction product appearing in scheme (Eq. 6) may be joined together to form a ring, while $R^{48}$ and $R^{49}$ and/or $R^{50}$ in the reaction product appearing in scheme (Eq. 7) may be joined together to form a ring, or $R^{49}$ and $R^{50}$ may be joined together to form a ring.

An explanation will be made of $R^{44}$, $R^{45}$, $R^{46}$, $R^{47}$ and $R^{48}$ in schemes (Eq. 5), (Eq. 6) and (Eq. 7). The alkyl, aryl, aralkyl, alkenyl, alkynyl, alkyloxy, aryloxy, aralkyloxy and heteroaryl groups intended in $R^{44}$, $R^{45}$, $R^{46}$, $R^{47}$ and $R^{48}$ include an alkyl group, an aryl group, an aralkyl group, an alkenyl group, an alkynyl group, an alkyloxy group, an aryloxy group, an aralkyloxy group and a heteroaryl group as discussed above in the explanation of $R^1$ and $R^2$ in general formula ($G^P$). The keto group intended here includes a keto group as discussed above in the explanation of $R^K$ in general formula (15), while the alkoxycarbonyl, cycloalkyloxycarbonyl, aryloxycarbonyl, aralkyloxycarbonyl, alkenyloxy and alkynyloxy groups intended here include an alkoxycarbonyl group, an aryloxycarbonyl group, an aralkyloxycarbonyl group, an alkenyloxy group and an alkynyloxy group as discussed above in the explanation of $R^{39}$ and $R^{40}$ in scheme (Eq. 3). Substituents which may be substituted on these alkyl, aryl, aralkyl, alkenyl, alkynyl, alkyloxy, aryloxy, aralkyloxy and heteroaryl groups include an alkyl group, an aryl group, an aralkyl group, an alkenyl group, an alkynyl group, an alkyloxy group, an aryloxy group, an aralkyloxy group, a halogen atom, a silyl group, a heteroaryl group, an optionally protected hydroxyl group, etc., and an amino group as discussed above in the explanation of $R^1$ and $R^2$ in general formula ($G^P$), a keto group as discussed above in the explanation of $R^K$ in general formula (15), as well as an alkoxycarbonyl group, an aryloxycarbonyl group, an aralkyloxycarbonyl group and an alkenyloxycarbonyl group as discussed above in the explanation of $R^{39}$ and $R^{40}$ in scheme (Eq. 3).

An explanation will be made of $R^{49}$ and $R^{50}$ in scheme (Eq. 7). The alkyl, aryl, aralkyl, alkenyl, alkynyl, alkyloxy, aryloxy, aralkyloxy and heteroaryl groups intended in $R^{49}$ and $R^{50}$ include an alkyl group, an aryl group, an aralkyl group, an alkenyl group, an alkynyl group, an alkyloxy group, an aryloxy group, an aralkyloxy group and a heteroaryl group as discussed above in the explanation of $R^1$ and $R^2$ in general formula ($G^P$). Substituents which may be substituted on these alkyl, aryl, aralkyl, alkenyl, alkynyl, alkyloxy, aryloxy, aralkyloxy and heteroaryl groups include an alkyl group, an aryl group, an aralkyl group, an alkenyl group, an alkynyl group, an alkyloxy group, an aryloxy group, an aralkyloxy group, a halogen atom, a silyl group, a heteroaryl group, an optionally protected hydroxyl group, etc., and an amino group as discussed above in the explanation of $R^1$ and $R^2$ in general formula ($G^P$), a keto group as discussed above in the explanation of $R^K$ in general formula (15), as well as an alkoxycarbonyl group, an aryloxycarbonyl group, an aralkyloxycarbonyl group and an alkenyloxycarbonyl group as discussed above in the explanation of $R^{39}$ and $R^{40}$ in scheme (Eq. 3).

When $R^{44}$ and $R^{45}$ are joined together to form a ring, such a ring is exemplified by those as discussed above in the explanation of general formula ($G^P$) where $R^1$ and $R^2$ are joined together to form a ring.

In scheme (Eq. 6), when $R^{46}$ and $R^{47}$ are joined together to form a ring, such a ring is exemplified by those as discussed above in the explanation of general formula ($G^P$) where $R^1$ and $R^2$ are joined together to form a ring. In this case, the reaction product appearing in scheme (Eq. 6) is a lactone.

In scheme (Eq. 7), when $R^{48}$ and $R^{49}$ and/or $R^{50}$ are joined together to form a ring, preferably when $R^{48}$ and $R^{49}$ or $R^{50}$ are joined together to form a ring, such a ring is exemplified by those as discussed above in the explanation of general formula ($G^P$) where $R^1$ and $R^2$ are joined together to form a ring. In this case, the reaction product appearing in scheme (Eq. 7) is a lactam.

Oxidation of alcohols into carbonyl compounds by dehydrogenation of alcohols in the present invention may be accomplished preferably in the absence or presence of a solvent, but it is preferable to use a solvent. The same goes for oxidation of hemiacetals into carbonyl compounds by dehydrogenation of hemiacetals. The same also goes for oxidation of hemiaminals into carbonyl compounds by dehydrogenation of hemiaminals.

Solvents preferred for use are those in which a substrate can be dissolved, and a single solvent or a mixed solvent is used for this purpose. Specific examples include aromatic hydrocarbons (e.g., toluene, xylene), aliphatic hydrocarbons (e.g., hexane, heptane), halogenated hydrocarbons (e.g., methylene chloride, chlorobenzene), ethers (e.g., diethyl ether, tetrahydrofuran, methyl tert-butyl ether, cyclopentyl methyl ether), and ketones (e.g., 1-phenylethanone, benzophenone).

The amount of such a solvent to be used may be selected as appropriate depending on the reaction conditions, etc. The reaction may optionally be conducted under stirring conditions.

The amount of the catalyst to be used, the reaction temperature and the reaction time may be those as discussed above for hydrogenation reduction from ketones into alcohols.

After completion of the reaction, commonly used purification techniques such as extraction, filtration, crystallization, distillation, and various types of chromatography may be used alone or in combination, as appropriate, to obtain a desired product.

During oxidation of alcohols into carbonyl compounds, additives may also be added as appropriate, as in the case of hydrogenation reaction of ketones, and examples of additives include the same additives as discussed above for hydrogenation reduction from ketones into alcohols. The same goes for oxidation of hemiacetals into carbonyl compounds by dehydrogenation of hemiacetals. The same also goes for oxidation of hemiaminals into carbonyl compounds by dehydrogenation of hemiaminals.

Subsequently, an explanation will be made of a method for manufacturing alkylamines by dehydrogenation condensation between alcohols and amines.

Such a method for manufacturing alkylamines by dehydrogenation condensation between alcohols and amines in the present invention is as shown in the following scheme (Eq. 8), (Eq. 9) or (Eq. 10):

[Formula 48]

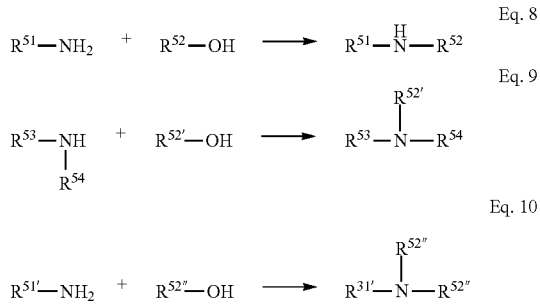

In schemes (Eq. 8), (Eq. 9) and (Eq. 10), $R^{51}$, $R^{51'}$, $R^{53}$ and $R^{54}$ are each independently selected from an alkyl group, an aryl group, an aralkyl group, an alkenyl group, an alkynyl group, an alkyloxy group, an aryloxy group, an aralkyloxy group or a heteroaryl group, and these alkyl, aryl, aralkyl, alkenyl, alkynyl, alkyloxy, aryloxy, aralkyloxy and heteroaryl groups are optionally substituted. $R^{52}$, $R^{52'}$ and $R^{52''}$ are each independently selected from an alkyl group, an aryl group, an aralkyl group, an alkenyl group, an alkynyl group or a heteroaryl group, and these alkyl, aryl, aralkyl, alkenyl, alkynyl and heteroaryl groups are optionally substituted. Moreover, $R^{51}$ and $R^{52}$ in the reaction product appearing in scheme (Eq. 8) may be joined together to form a ring. Likewise, $R^{53}$ and $R^{54}$, or $R^{52'}$ and $R^{53}$ and/or $R^{54}$ in the reaction product appearing in scheme (Eq. 9) may be joined together to form a ring, while $R^{51'}$ and $R^{52''}$, or $R^{51'}$ and $R^{52''}$ and $R^{52''}$ in the reaction product appearing in scheme (Eq. 10) may be joined together to form a ring.

An explanation will be made of $R^{51}$, $R^{51'}$, $R^{52}$, $R^{52'}$, $R^{52''}$, $R^{53}$ and $R^{54}$ in schemes (Eq. 8), (Eq. 9) and (Eq. 10). The alkyl, aryl, aralkyl, alkenyl, alkynyl, alkyloxy, aryloxy, aralkyloxy and heteroaryl groups intended in $R^{51}$, $R^{51'}$, $R^{53}$ and $R^{54}$ include an alkyl group, an aryl group, an aralkyl group, an alkenyl group, an alkynyl group, an alkyloxy group, an aryloxy group, an aralkyloxy group and a heteroaryl group as discussed above in the explanation of $R^1$ and $R^2$ in general formula ($G^P$).

Substituents which may be substituted on these alkyl, aryl, aralkyl, alkenyl, alkynyl, alkyloxy, aryloxy, aralkyloxy and heteroaryl groups include an alkyl group, an aryl group, an aralkyl group, an alkenyl group, an alkynyl group, an alkyloxy group, an aryloxy group, an aralkyloxy group, a halogen atom, a silyl group, a heteroaryl group, an optionally protected hydroxyl group and an amino group as discussed above in the explanation of $R^1$ and $R^2$ in general formula ($G^P$).

The alkyl, aryl, aralkyl, alkenyl, alkynyl and heteroaryl groups intended in $R^{52}$, $R^{52'}$ and $R^{52''}$ include an alkyl group, an aryl group, an aralkyl group, an alkenyl group, an alkynyl group and a heteroaryl group as discussed above in the explanation of $R^1$ and $R^2$ in general formula ($G^P$).

Substituents which may be substituted on these alkyl, aryl, aralkyl, alkenyl, alkynyl and heteroaryl groups include an alkyl group, an aryl group, an aralkyl group, an alkenyl group, an alkynyl group, an alkyloxy group, an aryloxy group, an aralkyloxy group, a halogen atom, a silyl group, a heteroaryl group, an optionally protected hydroxyl group and an amino group as discussed above in the explanation of $R^1$ and $R^2$ in general formula ($G^P$).

In scheme (Eq. 8), when $R^{51}$ and $R^{52}$ in the reaction product are joined together to form a ring, such a ring is exemplified by those as discussed above in the explanation of general formula ($G^P$) where $R^1$ and $R^2$ are joined together to form a ring.

In scheme (Eq. 9), when $R^{53}$ and $R^{54}$, or $R^{52'}$ and $R^{53}$ and/or $R^{54}$ in the reaction product are joined together to form a ring, such a ring is exemplified by those as discussed above in the explanation of general formula ($G^P$) where $R^1$ and $R^2$ are joined together to form a ring.

In scheme (Eq. 10), when $R^{51'}$ and $R^{52''}$, and further $R^{51'}$ and $R^{52''}$ in the reaction product are joined together to form a ring, such a ring is exemplified by those as discussed above in the explanation of general formula ($G^P$) where $R^1$ and $R^2$ are joined together to form a ring.

The method for manufacturing alkylamines by dehydrogenation condensation between alcohols and amines in the present invention may be accomplished preferably in the absence or presence of a solvent.

When using a solvent, solvents preferred for use are those in which a substrate can be dissolved, and a single solvent or a mixed solvent is used for this purpose. Specific examples include aromatic hydrocarbons (e.g., toluene, xylene), aliphatic hydrocarbons (e.g., hexane, heptane), halogenated hydrocarbons (e.g., methylene chloride, chlorobenzene), ethers (e.g., diethyl ether, tetrahydrofuran, methyl tert-butyl ether, cyclopentyl methyl ether) and so on.

The amount of such a solvent to be used may be selected as appropriate depending on the reaction conditions, etc. The reaction may optionally be conducted under stirring conditions.

The method for manufacturing alkylamines by dehydrogenation condensation between alcohols and amines in the present invention does not particularly require any hydrogen donor, but a hydrogen donor may be used. Examples of a hydrogen donor available for use in the method of the present invention include a hydrogen gas, formic acid, a primary alcohol (e.g., methanol, ethanol, butanol) and a secondary alcohol (e.g., isopropanol), etc.

When using a hydrogen donor, the pressure of a hydrogen gas is 0.1 MPa to 5 MPa, preferably 0.5 MPa to 3 MPa.

The amount of the catalyst to be used, the reaction temperature and the reaction time may be those as discussed above for hydrogenation reduction from ketones into alcohols.

After completion of the reaction, commonly used purification techniques such as extraction, filtration, crystallization, distillation, and various types of chromatography may be used alone or in combination, as appropriate, to obtain a desired product.

In the method for manufacturing alkylamines by dehydrogenation condensation between alcohols and amines, additives may also be added as appropriate, as in the case of hydrogenation reduction of ketones, and examples of additives include the same additives as discussed above for hydrogenation reduction from ketones into alcohols.

EXAMPLES

The present invention will be further described in more detail by way of the following examples and comparative examples, which are not intended to limit the present invention. In these examples and comparative examples, the instruments and conditions used for measurement of physical properties are as shown below.

1) Proton nuclear magnetic resonance spectroscopy ($^1$H NMR): 400 MR/DD2 (resonance frequency: 400 MHz, Agilent), internal standard: tetramethylsilane (0 ppm (singlet peak) or residual light solvent (chloroform: 7.26 ppm (singlet peak))

2) Phosphorus-31 nuclear magnetic resonance spectroscopy ($^{31}$P NMR): 400 MR/DD2 (resonance frequency: 161 MHz, Agilent), external standard: phosphoric acid in heavy water (0 ppm (singlet peak))

3) Gas chromatography (GC): GC-4000 system (GL Sciences Inc., Japan), column: InertCap5 (GL Sciences Inc., Japan), sample inlet: 250° C., sample detector: 280° C., initial temperature: 70° C., initial temperature retention time: 2 minutes, temperature rise rate 1: 10° C./minute, final temperature: 280° C., final temperature retention time: 5 minutes 4) High-resolution mass spectrometry (HRMS): LCMS-I T-TOF system (Shimadzu Corporation, Japan)

It should be noted that substrates and solvents and others were charged under a nitrogen stream, reactions were conducted under a nitrogen atmosphere, and reaction mixture work-up and crude product purification were conducted in air, unless otherwise specified.

<Example 1> Synthesis of Compound $7^A$, Route 1 amine)-ethyl bromide (structural formula $17^C$) (2.0 g, 8.92 mmoL, 1.0 equivalent) and N,N-dimethylformamide (DMF) (25.6 mL). The resulting mixture was heated to 120° C. and stirred for 8 hours. After the reaction mixture was cooled to 5° C., ethyl acetate (EtOAc) (30 mL) and water (30 mL) were sequentially added to separate the organic layer. After the aqueous layer was extracted twice with ethyl acetate (30 mL), the organic layers were combined and washed with saturated aqueous sodium chloride (30 mL). The organic layer was dried over anhydrous sodium sulfate and then concentrated under reduced pressure. The resulting residue was purified by silica gel column chromatography (eluent: hexane/ethyl acetate=10/1) to give the titled compound ($17^B$) as a white solid (2.72 g). Isolated yield: 52.1%.

$^1$H-NMR (400 MHz, CDCl$_3$): δ=7.41-7.27 (m, 10H), 5.28 (br s, 1H), 3.04 (d, J=2.4 Hz, 2H), 2.56-2.46 (m, 6H), 2.04-2.02 (m, 4H), 1.43 (s, 9H).

$^{31}$P-NMR (161 MHz, CDCl$_3$): δ=−20.4.

Second Step: Synthesis of Compound $7^A$

A 100 mL four-necked round-bottomed flask was equipped with a magnetic stirrer bar, a condenser tube and a thermometer, purged with nitrogen, and then charged sequentially with compound $17^B$ obtained in the first step (0.5 g, 0.855 mmoL) and ethyl acetate (EtOAc) (16.0 mL), followed by addition of 4 M aqueous hydrochloric acid (8.0 mL) under conditions of an internal temperature of 25° C. The resulting two-layer mixture was heated to 80° C. and stirred for 3.5 hours. After the reaction mixture was cooled to 5° C., saturated aqueous sodium bicarbonate was added

[Formula 49]

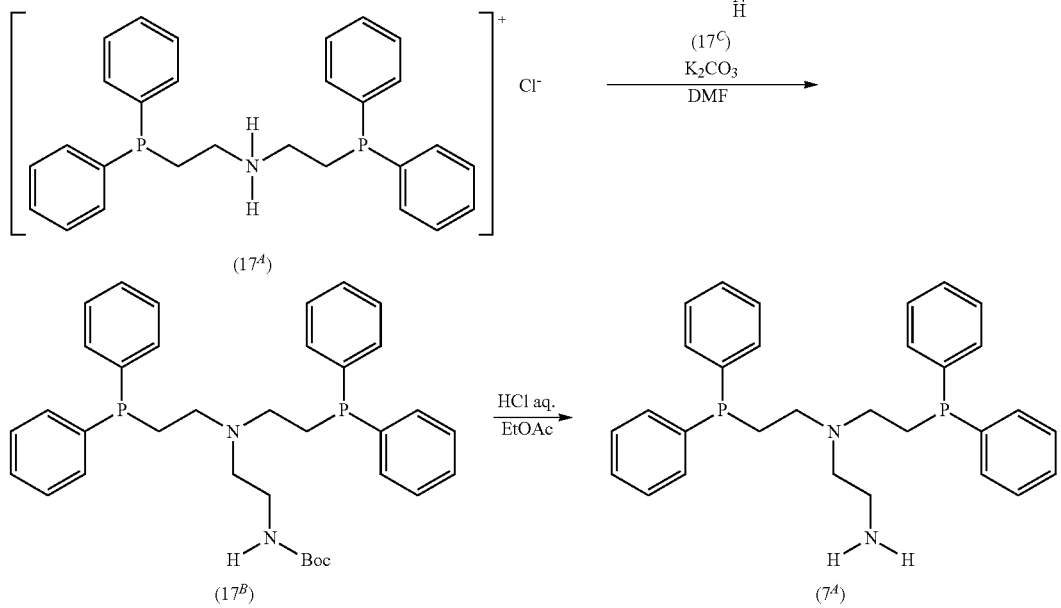

First Step: Synthesis of Compound $17^B$

A 100 mL four-necked round-bottomed flask was equipped with a magnetic stirrer bar, a condenser tube and a thermometer, purged with nitrogen, and then charged sequentially with bis[(2-diphenylphosphino)ethyl]amine hydrochloride (4.27 g, 8.92 mmoL, 1.0 equivalent), potassium carbonate (3.7 g, 26.8 mmoL, 3.0 equivalents), 2-(Bocuntil the aqueous layer reached pH=8, and the organic layer was then separated. After the aqueous layer was extracted twice with ethyl acetate (50 mL), the organic layers were combined and washed with saturated aqueous sodium chloride (30 mL). The organic layer was dried over anhydrous sodium sulfate and then concentrated under reduced pressure. The resulting residue was purified by silica gel column chromatography (eluent: hexane/ethyl acetate=10/1) to give the titled compound (7A) as a colorless oil (0.4 g).
Isolated yield: 96.5%.

$^1$H-NMR (400 MHz, CDCl$_3$): δ=7.42-7.28 (m, 20H), 2.58-2.50 (m, 6H), 2.45-2.42 (m, 2H), 2.10-2.04 (m, 4H).

$^{31}$P-NMR (161 MHz, CDCl$_3$): δ=−20.8.

HRMS (ESI, m/z) calculated for C$_{30}$H$_{35}$N$_2$P$_2$ ([M+H]$^+$) 485.2275. found 485.2265.

<Example 2> Synthesis of Compound 7$^A$, Route 2 eter, purged with nitrogen, and then charged sequentially with bis[(2-diphenylphosphino)ethyl]amine hydrochloride (20.0 g, 0.0419 moL, 1.0 equivalent), N-Boc-glycine (structural formula 17$^E$) (7.3 g, 0.0419 moL, 1.0 equivalent), 2-chloro-4,6-dimethoxy-1,3,5-triazine (structural formula 17$^F$) (74 g, 0.0419 moL, 1.0 equivalent), acetonitrile (400 mL) and 4-methylmorpholine (10.6 g, 0.105 moL, 2.5 equivalents). The resulting mixture was heated to 30° C. and stirred for 7 hours.

After the reaction mixture was concentrated under reduced pressure, the resulting residue was purified by silica

[Formula 50]

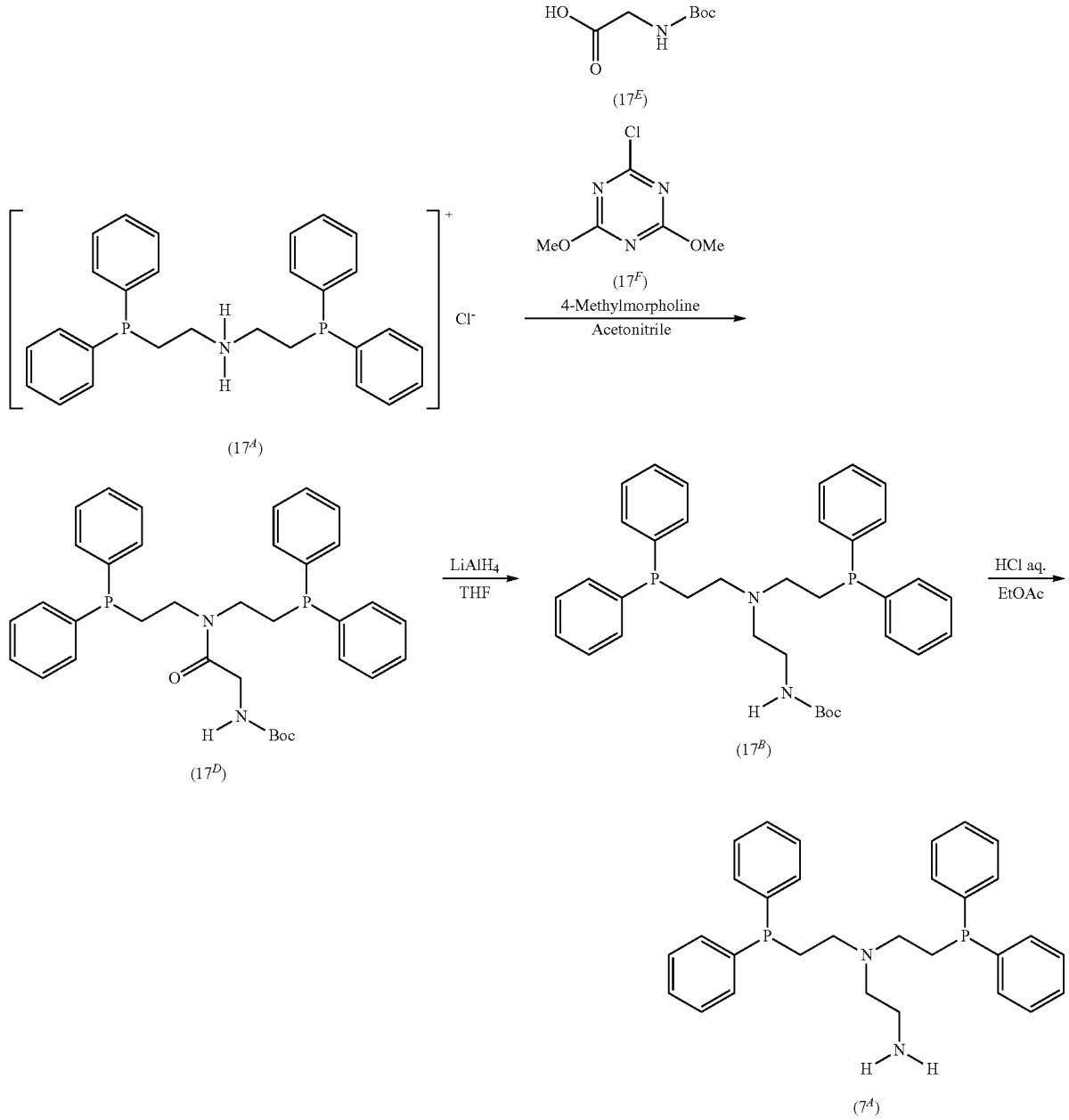

First Step: Synthesis of compound 17$^D$

A 1 L four-necked round-bottomed flask was equipped with an overhead stirrer, a condenser tube and a thermomgel column chromatography (ethyl acetate) to give the titled compound (17D) as a colorless liquid (24.7 g). Isolated yield: 98.7%.

$^1$H-NMR (400 MHz, CDCl$_3$): δ=7.41-7.30 (m, 20H), 5.38 (br s, 1H), 3.72 (d, J=2.4 Hz, 2H), 3.43-3.38 (m, 2H), 3.20-3.16 (m, 2H), 2.29-2.19 (m, 4H), 1.44 (s, 9H).

$^{31}$P-NMR (161 MHz, CDCl$_3$): δ=−20.6.

Second Step: Synthesis of compound 17$^B$

A 300 mL four-necked round-bottomed flask was equipped with an overhead stirrer, a condenser tube and a thermometer, purged with nitrogen, and then charged sequentially with compound (17$^D$) (11.5 g, 0.0192 moL, 1.0 equivalent) and tetrahydrofuran (100 mL). The resulting mixture was cooled to 2° C. in an ice bath. A tetrahydrofuran solution of lithium aluminum hydride (2.5 moL/L, 7.7 mL, 1.0 equivalent) was added dropwise, and after completion of the dropwise addition, the resulting mixture was heated to 15° C. and stirred for 6 hours. The reaction mixture was cooled to 2° C. in an ice bath, and H$_2$O (100 mL) was added to stop the reaction. After the resulting aqueous layer was extracted twice with ethyl acetate (100 mL), the organic layers were combined and washed with saturated aqueous sodium chloride (30 mL). After the organic layer was dried over anhydrous sodium sulfate and concentrated under reduced pressure, the resulting residue was purified by silica gel column chromatography (ethyl acetate/hexane=1:1) to give the titled compound (17$^B$) as a white solid (8.7 g). Isolated yield: 77.3%.

$^1$H-NMR (400 MHz, CDCl$_3$): δ=7.41-7.27 (m, 10H), 5.28 (br s, 1H), 3.04 (d, J=2.4 Hz, 2H), 2.56-2.46 (m, 6H), 2.04-2.02 (m, 4H), 1.43 (s, 9H).

$^{31}$P-NMR (161 MHz, CDCl$_3$): δ=−20.4.

Third Step: Synthesis of compound 7$^A$

A 100 mL four-necked round-bottomed flask was equipped with a magnetic stirrer bar, a condenser tube and a thermometer, purged with nitrogen, and then charged sequentially with compound 17$^B$ obtained in the second step (0.5 g, 0.855 mmoL) and ethyl acetate (EtOAc) (16.0 mL), followed by addition of 4 M aqueous hydrochloric acid (8.0 mL) under conditions of an internal temperature of 25° C. The resulting two-layer mixture was heated to 80° C. and stirred for 3.5 hours.

After the reaction mixture was cooled to 5° C., saturated aqueous sodium bicarbonate was added until the aqueous layer reached pH=8, and the organic layer was then separated. After the aqueous layer was extracted twice with ethyl acetate (50 mL), the organic layers were combined and washed with saturated aqueous sodium chloride (30 mL). The organic layer was dried over anhydrous sodium sulfate and then concentrated under reduced pressure. The resulting residue was purified by silica gel column chromatography (eluent: hexane/ethyl acetate=10/1) to give the titled compound (7A) as a white solid (0.4 g). Isolated yield: 96.5%.

$^1$H-NMR (400 MHz, CDCl$_3$): δ=7.42-7.28 (m, 20H), 2.58-2.50 (m, 6H), 2.45-2.42 (m, 2H), 2.10-2.04 (m, 4H).

$^{31}$P-NMR (161 MHz, CDCl$_3$): δ=−20.2.

HRMS (ESI, m/z) calculated for C$_{30}$H$_{35}$N$_2$P$_2$ ([M+H]$^+$) 485.2275. found 485.2265.

<Example 3> Synthesis of Compound 6$^A$-1, Route 1

[Formula 51]

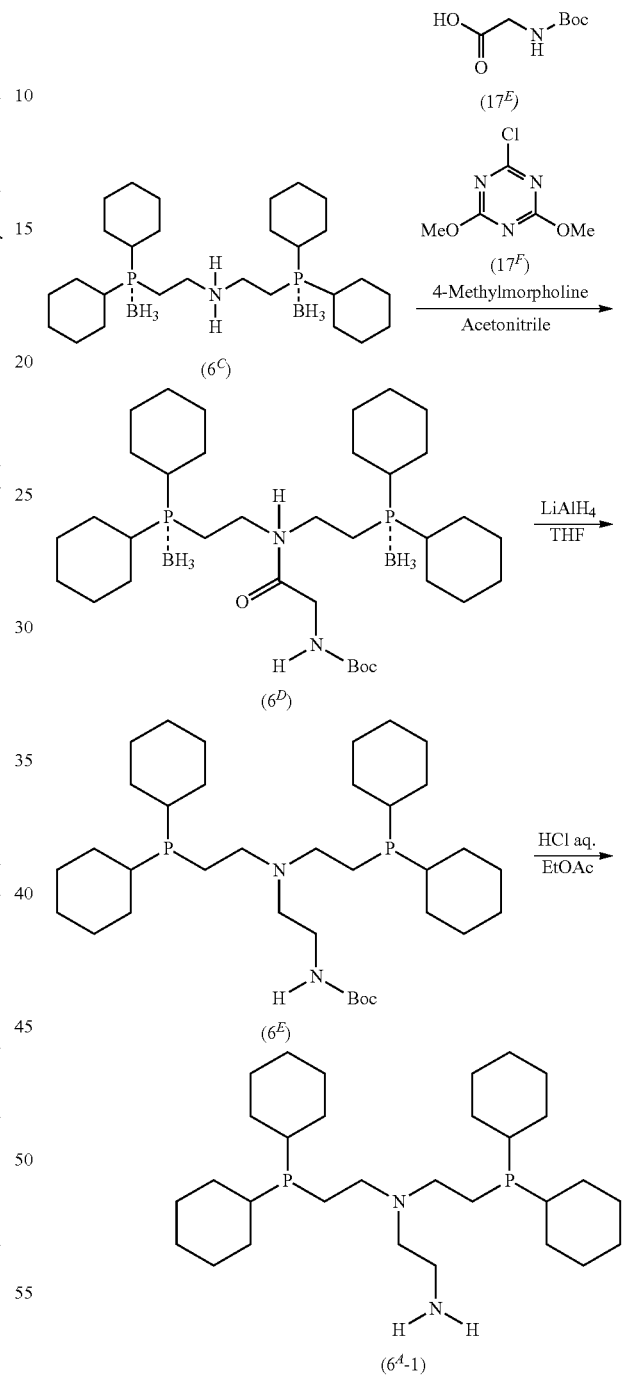

First Step: Synthesis of Compound 6$^D$

A 1 L four-necked round-bottomed flask was equipped with an overhead stirrer, a condenser tube and a thermometer, purged with nitrogen, and then charged sequentially with compound 6$^C$ (1.0 g, 2.03 mmoL, 1.0 equivalent), N-Boc-glycine (structural formula 17$^E$) (355.1 mg, 2.03 mmoL, 1.0 equivalent), 2-chloro-4,6-dimethoxy-1,3,5-triazine (structural formula 17$^F$) (355.9 mg, 2.03 mmoL, 1.0 equivalent), acetonitrile (100 mL) and 4-methylmorpholine (922.6 mg, 9.122 mmoL, 4.5 equivalents). The resulting mixture was heated to 30° C. and stirred for 7 hours. After the reaction mixture was concentrated under reduced pressure, the resulting residue was purified by silica gel column chromatography (ethyl acetate) to give the titled compound ($6^D$) as a white solid (0.7 g). Isolated yield: 55.4%.

$^1$H-NMR (400 MHz, CDCl$_3$): δ=3.94-3.93 (m, 2H), 3.54-3.43 (m, 4H), 1.88-1.63 (m, 28H), 1.45 (s, 9H), 1.38-1.20 (m, 20H).

$^{31}$P-NMR (161 MHz, CDCl$_3$): δ=−23.7.

HRMS (APCI, m/z) calculated for C$_{35}$H$_{65}$N$_2$O$_3$P$_2$ ([M+H]$^+$) 623.8635. found 623.4464.

Second Step: Synthesis of compound $6^E$

A 100 mL four-necked round-bottomed flask was equipped with an overhead stirrer, a condenser tube and a thermometer, purged with nitrogen, and then charged sequentially with compound ($6^D$) (0.7 g, 1.08 mmoL, 1.0 equivalent) and tetrahydrofuran (21 mL). The resulting mixture was cooled to 2° C. in an ice bath. A tetrahydrofuran solution of lithium aluminum hydride (2.5 moL/L, 0.86 mL, 2.0 equivalents) was added dropwise, and after completion of the dropwise addition, the resulting mixture was heated to 15° C. and stirred for 4 hours. The reaction mixture was cooled to 2° C. in an ice bath, and H$_2$O (2 mL) was added to stop the reaction, followed by addition of ethyl acetate (50 mL). The organic layer was dried over anhydrous sodium sulfate. The solids were removed by filtration, and the filtrate was concentrated under reduced pressure to give the titled compound ($6^E$) as a colorless liquid crude product (0.5 g).

$^1$H-NMR (400 MHz, CDCl$_3$): δ=3.18-3.17 (m, 2H), 2.76-2.71 (m, 4H), 2.57-2.54 (m, 2H), 1.88-1.64 (m, 28H), 1.45 (s, 9H), 1.36-1.23 (m, 20H).

$^{31}$P-NMR (161 MHz, CDCl$_3$): δ=−24.2.

HRMS (ESI, m/z) calculated for C$_{35}$H$_{67}$N$_2$O$_2$P$_2$([M+H]$^+$) 609.4678. found 609.4673.

Third Step: Synthesis of Compound $6^A$-1

A 100 mL four-necked round-bottomed flask was equipped with a magnetic stirrer bar, a condenser tube and a thermometer, purged with nitrogen, and then charged sequentially with compound $6^E$ obtained in the second step (0.5 g, 0.821 mmoL) and ethyl acetate (EtOAc) (10.0 mL), followed by addition of 4 M aqueous hydrochloric acid (5.0 mL) under conditions of an internal temperature of 20° C. The resulting two-layer mixture was heated to 60° C. and stirred for 4 hours.

After the reaction mixture was cooled to 5° C., 5 M aqueous sodium hydroxide was added until the aqueous layer reached pH=8, and the organic layer was then separated. After the aqueous layer was extracted three times with ethyl acetate (30 mL), the organic layers were combined and washed with saturated aqueous sodium chloride (30 mL). The organic layer was dried over anhydrous sodium sulfate and then concentrated under reduced pressure to give the titled compound ($6^A$-1) as a white solid crude product (0.38 g).

$^1$H-NMR (400 MHz, CDCl$_3$): δ=2.79-2.72 (m, 6H), 2.55-2.52 (m, 2H), 1.83-1.61 (m, 28H), 1.34-1.24 (m, 20H).

$^{31}$P-NMR (161 MHz, CDCl$_3$): δ=−22.2.

HRMS (APPI, m/z) calculated for C$_{30}$H$_{59}$N$_2$P$_2$ ([M+H]$^+$) 509.4153. found 509.4158.

<Example 4> Synthesis of Compound $6^A$-4, Route 1

[Formula 52]

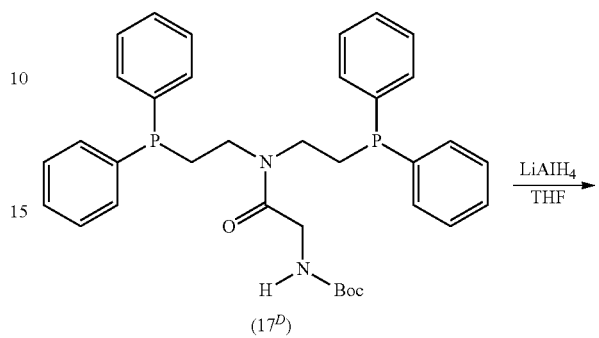

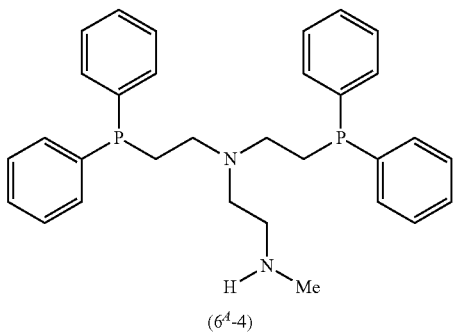

A 300 mL four-necked round-bottomed flask was equipped with an overhead stirrer, a condenser tube and a thermometer, purged with nitrogen, and then charged sequentially with compound ($17^D$) (7.0 g, 0.0117 moL, 1.0 equivalent) and tetrahydrofuran (60 mL). The resulting mixture was cooled to 2° C. in an ice bath. A tetrahydrofuran solution of lithium aluminum hydride (2.5 moL/L, 4.9 mL, 1.0 equivalent) was added dropwise, and after completion of the dropwise addition, the resulting mixture was heated to 60° C. and stirred for 6 hours. The reaction mixture was cooled to 2° C. in an ice bath, and H$_2$O (5 mL) was added to stop the reaction, followed by addition of ethyl acetate (100 mL). The organic layer was dried over anhydrous sodium sulfate. The solids were removed by filtration, and the filtrate was concentrated under reduced pressure to give the titled compound ($6^A$-4) as a colorless liquid crude product (5.1 g).

$^1$H-NMR (400 MHz, CDCl$_3$): δ=7.43-7.27 (m, 20H), 2.58-2.50 (m, 6H), 2.50-2.42 (m, 2H), 2.33 (s, 3H), 2.10-2.06 (m, 4H).

$^{31}$P-NMR (161 MHz, CDCl$_3$): δ=−19.9.

HRMS (ESI, m/z) calculated for C$_{31}$H$_{36}$N$_2$P$_2$ ([M+H]$^+$) 499.2432. found 499.2421.

<Example 5> Synthesis of Compound 7[B], Route 1

[Formula 53]

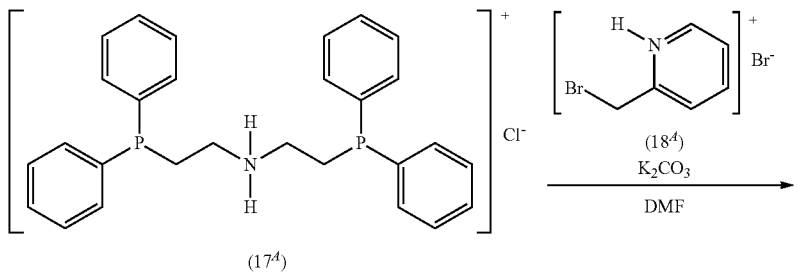

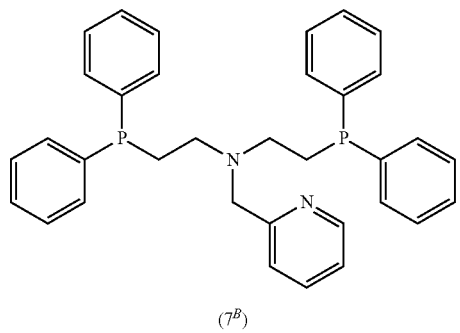

Synthesis of Compound 7[B]

A 100 mL four-necked round-bottomed flask was equipped with a magnetic stirrer bar, a condenser tube and a thermometer, purged with nitrogen, and then charged sequentially with bis[(2-diphenylphosphino)ethyl]amine hydrochloride (1.75 g, 3.95 mmoL, 1.0 equivalent), potassium carbonate (1.64 g, 11.9 mmoL, 3.0 equivalents), 2-(bromomethyl)-pyridine hydrobromide (18[A]) (1.0 g, 3.95 mmoL, 1.0 equivalent) and N,N-dimethylformamide (DMF) (10.5 mL). The resulting mixture was heated to 100° C. and stirred for 3 hours. After the reaction mixture was cooled to 5° C., ethyl acetate (EtOAc) (30 mL) and saturated aqueous sodium bicarbonate (30 mL) were sequentially added to separate the organic layer. After the aqueous layer was extracted twice with ethyl acetate (30 mL), the organic layers were combined and washed with saturated aqueous sodium chloride (30 mL). The organic layer was dried over anhydrous sodium sulfate and then concentrated under reduced pressure to give the titled compound (7[B]) as a brown liquid crude product (0.67 g).

$^1$H-NMR (400 MHz, CDCl$_3$): δ=8.46-8.45 (m, 1H), 7.41-7.26 (m, 22H), 7.11-7.08 (m, 1H), 3.74 (s, 2H), 2.66-2.61 (m, 4H), 2.28-2.12 (m, 4H).

$^{31}$P-NMR (161 MHz, CDCl$_3$): δ=−7.8.

HRMS (ESI, m/z) calculated for C$_{34}$H$_{34}$N$_2$P$_2$ ([M+H]$^+$) 533.2270. found 533.2268.

<Example 6> Synthesis of Compound 18[D]

[Formula 54]

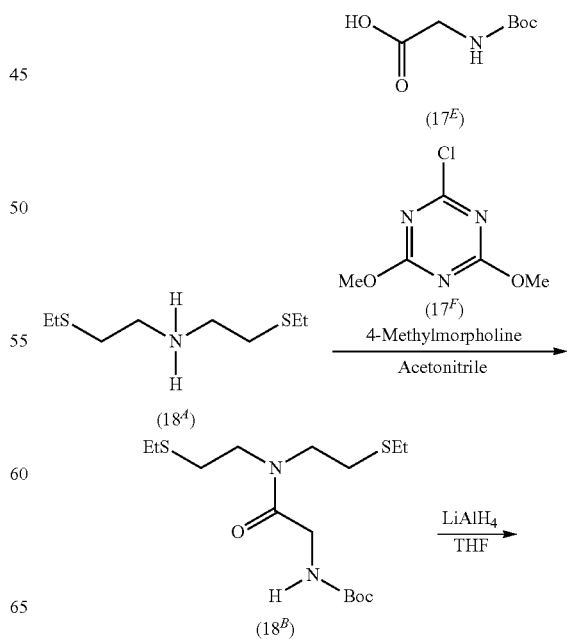

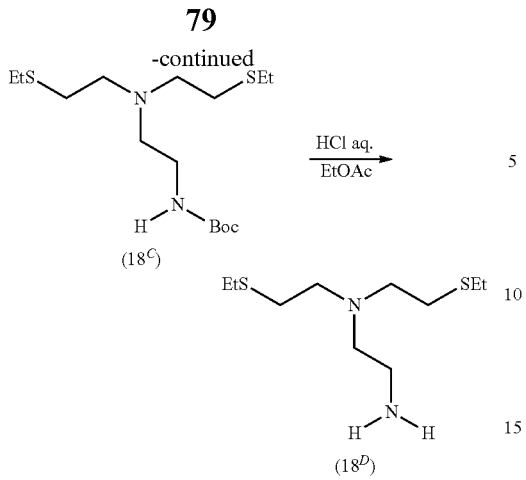

First Step: Synthesis of Compound 18$^B$

A 100 mL four-necked round-bottomed flask was equipped with an overhead stirrer, a condenser tube and a thermometer, purged with nitrogen, and then charged sequentially with bis[(2-ethylthio)ethyl]amine (structural formula 18$^A$) (1.67 g, 8.64 mmoL, 1.0 equivalent), N-Boc-glycine (structural formula 17$^E$) (1.51 g, 8.64 mmoL, 1.0 equivalent), 2-chloro-4,6-dimethoxy-1,3,5-triazine (structural formula 17$^F$) (1.52 g, 8.64 mmoL, 1.0 equivalent), acetonitrile (33.4 mL) and 4-methylmorpholine (2.18 g, 21.6 mmoL, 2.5 equivalents). The resulting mixture was heated to 30° C. and stirred for 8 hours. After the reaction mixture was concentrated under reduced pressure, the resulting residue was purified by silica gel column chromatography (ethyl acetate) to give the titled compound (18$^B$) as a colorless liquid (2.84 g). Isolated yield: 93.8%.

$^1$H-NMR (400 MHz, CDCl$_3$): δ=5.48 (br s, 1H), 4.05-3.96 (m, 2H), 3.56-3.44 (m, 2H), 2.73-2.68 (m, 4H), 2.62-2.55 (m, 4H), 1.45 (s, 9H), 1.30-1.24 (m, 6H).

Second Step: Synthesis of Compound 18$^C$

A 100 mL four-necked round-bottomed flask was equipped with an overhead stirrer, a condenser tube and a thermometer, purged with nitrogen, and then charged sequentially with compound (18$^B$) (1.42 g, 4.05 mmoL, 1.0 equivalent) and tetrahydrofuran (20 mL). The resulting mixture was cooled to 2° C. in an ice bath. A tetrahydrofuran solution of lithium aluminum hydride (2.5 moL/L, 3.2 mL, 2.0 equivalents) was added dropwise, and after completion of the dropwise addition, the resulting mixture was heated to 15° C. and stirred for 4 hours. The reaction mixture was cooled to 2° C. in an ice bath, and H$_2$O (5 mL) was added to stop the reaction, followed by addition of ethyl acetate (50 mL). The organic layer was dried over anhydrous sodium sulfate and further concentrated under reduced pressure to give the titled compound (18$^C$) as a colorless liquid crude product (0.76 g).

$^1$H-NMR (400 MHz, CDCl$_3$): δ=2.72-2.64 (m, 6H), 2.62-2.53 (m, 10H), 1.45 (s, 9H), 1.45-1.25 (m, 6H).

Third Step: Synthesis of Compound 18$^D$

A 100 mL four-necked round-bottomed flask was equipped with a magnetic stirrer bar, a condenser tube and a thermometer, purged with nitrogen, and then charged sequentially with compound 18$^C$ obtained in the second step (0.76 g, 2.26 mmoL) and ethyl acetate (EtOAc) (15.2 mL), followed by addition of 4 M aqueous hydrochloric acid (7.6 mL) under conditions of an internal temperature of 20° C. The resulting two-layer mixture was heated to 60° C. and stirred for 4 hours. After the reaction mixture was cooled to 5° C., 5 M aqueous sodium hydroxide was added until the aqueous layer reached pH=8, and the organic layer was then separated. After the aqueous layer was extracted three times with ethyl acetate (30 mL), the organic layers were combined and washed with saturated aqueous sodium chloride (30 mL). The organic layer was dried over anhydrous sodium sulfate and then concentrated under reduced pressure to give the titled compound (18D) as a colorless liquid crude product (0.50 g).

$^1$H-NMR (400 MHz, CDCl$_3$): δ=2.75-2.68 (m, 6H), 2.64-2.53 (m, 10H), 1.28-1.24 (m, 6H).

HRMS (APPI, m/z) calculated for C$_{10}$H$_{24}$N$_2$S$_2$ ([M+H]$^+$) 237.1454. found 237.1458.

<Example 7> Synthesis of Compound 19$^B$, Route 1

[Formula 55]

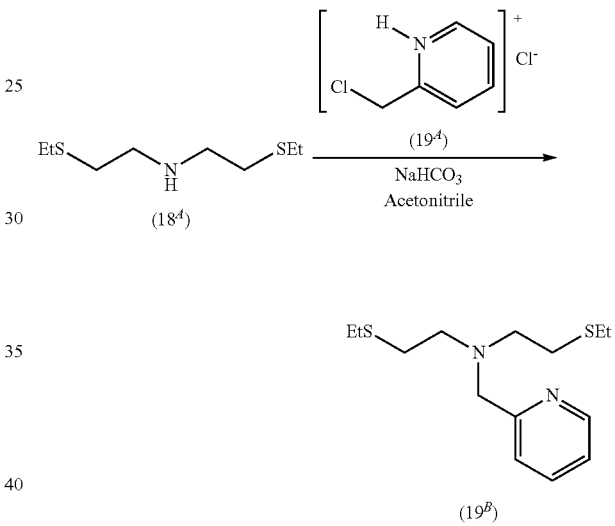

Synthesis of Compound 19$^B$

A 100 mL four-necked round-bottomed flask was equipped with an overhead stirrer, a condenser tube and a thermometer, purged with nitrogen, and then charged sequentially with bis[(2-diphenylphosphino)ethyl]amine hydrochloride (1.82 g, 9.41 mmoL, 1.0 equivalent), sodium bicarbonate (2.37 g, 28.2 mmoL, 3.0 equivalents), 2-(chloromethyl)-pyridine hydrochloride (19$^A$) (1.62 g, 9.88 mmoL, 1.05 equivalents) and acetonitrile (18.2 mL). The resulting mixture was heated to 70° C. and stirred for 7 hours. The precipitated solids were removed by filtration. After the filtrate was concentrated under reduced pressure, the resulting residue was purified by silica gel column chromatography (ethyl acetate:hexane=3:1) to give the titled compound (19$^B$) as a brown liquid (1.12 g). Isolated yield: 41.8%.

$^1$H-NMR (400 MHz, CDCl$_3$): δ=2.75-2.68 (m, 6H), 7.73-7.64 (m, 1H), 7.54-7.51 (m, 1H), 7.17-7.14 (m, 1H), 3.82 (s, 2H), 2.81-2.75 (m, 4H), 2.81-2.75 (m, 4H), 2.73-2.63 (m, 4H), 1.29-1.19 (m, 6H).

HRMS (APPI, m/z) calculated for C$_{14}$H$_{24}$N$_2$S$_2$ ([M+H]$^+$) 285.1454. found 285.1461.

Example 8

Synthesis of Compound 8$^Y$

[Formula 56]

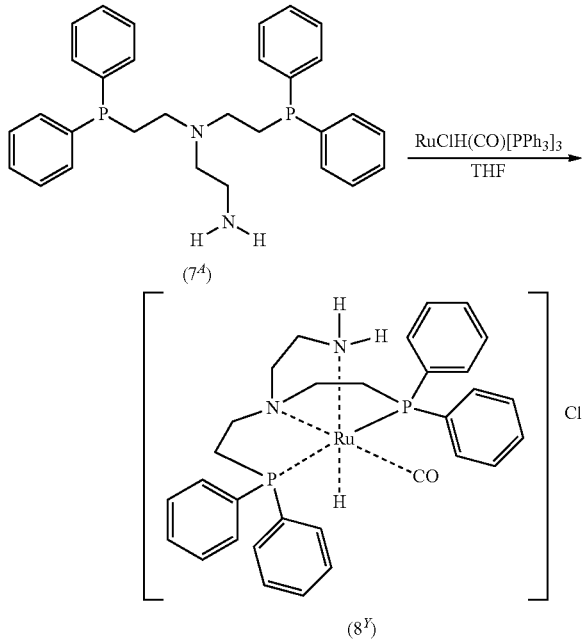

A 50 mL four-necked round-bottomed flask was equipped with a magnetic stirrer bar, a condenser tube and a thermometer, purged with nitrogen, and then charged sequentially with RuClH(CO)(PPh$_3$)$_3$ (197 mg, 0.206 mmoL, 1.0 equivalent), compound 7$^A$ obtained in the second step of Example 1 (100 mg, 0.206 mmoL) and tetrahydrofuran (THF) (4.0 mL). The resulting yellow suspension was stirred under reflux for 5 hours. After the reaction, the resulting yellow suspension was cooled to 5° C. and subjected to suction filtration. The crystals collected by filtration were then washed with tetrahydrofuran and heated to dryness under reduced pressure to give the titled compound (8$^Y$) as a white powder (20 mg) (this compound is designated as 8$^Y$-1). Isolated yield: 14.6%. Subsequently, the filtrate was concentrated under reduced pressure, and the resulting residue was diluted with tetrahydrofuran (5.0 mL) and stirred under reflux to become homogeneous. When the resulting homogeneous solution was cooled to 30° C., crystals were precipitated again to form a suspension. To the resulting yellow suspension, toluene (3.0 mL) was added dropwise, and after completion of the dropwise addition, the mixture was stirred for 1 hour under conditions of 15° C. The resulting yellow suspension was subjected to suction filtration, and the crystals collected by filtration were then washed with tetrahydrofuran and heated to dryness under reduced pressure to give the titled compound (8$^Y$) as a white powder (22 mg) (this compound is designated as 8$^Y$-2). Isolated yield: 16.1%.

Compound 8$^Y$-1
$^1$H-NMR (400 MHz, CD$_2$Cl$_2$): see FIG. 1.
$^{31}$P-NMR (161 MHz, CD$_2$Cl$_2$): δ=56.1 (s, 1P).
HRMS (ESI, m/z) calculated for C$_{31}$H$_{35}$N$_2$OP$_2$Ru ([M−HCl]$^{2+}$) 615.1268. found 615.1201.

Figure 2:
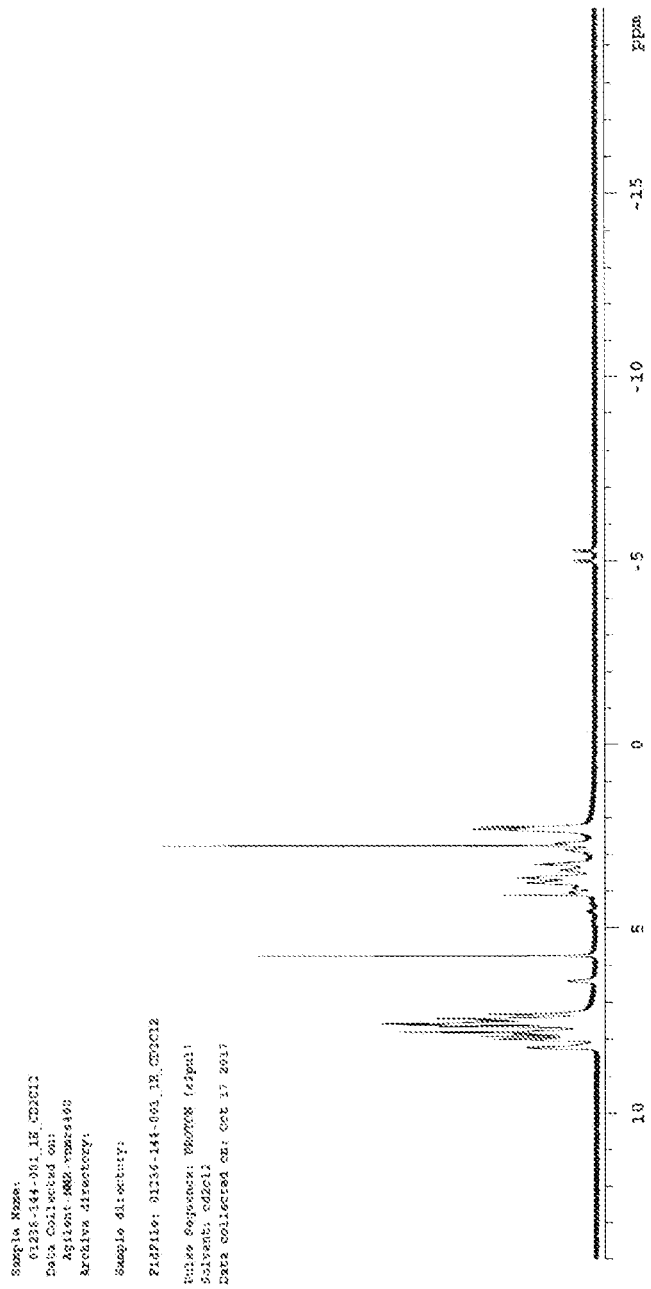
FIG. 2 shows a $^1$H-NMR spectrum of complex $8^Y$-2 obtained in Example 8.

Compound 8$^Y$-2
$^1$H-NMR (400 MHz, CD$_2$Cl$_2$): see FIG. 2.
$^{31}$P-NMR (161 MHz, CD$_2$Cl$_2$): δ=67.6 (d, J=8.9 Hz, 1P), 44.0 (t, J=8.8 Hz, 1P).
HRMS (ESI, m/z) calculated for C$_{31}$H$_{35}$N$_2$OP$_2$Ru ([M−HCl]$^{2+}$) 615.1268. found 615.1263.

Figure 4:
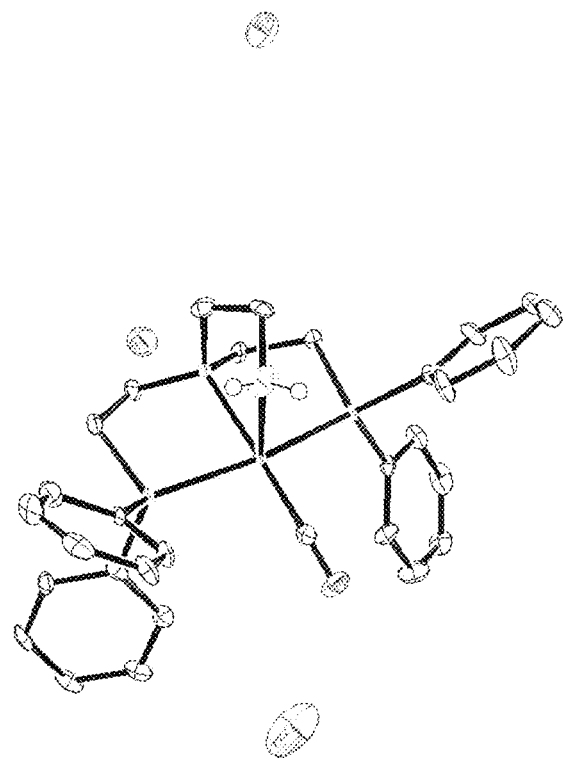
FIG. 4 shows an ORTEP view of complex $8^Y$-1 obtained in Example 8, as determined by X-ray crystal structure analysis.

Further, as for compound 8$^Y$-1 obtained in this example, a single crystal was prepared with tetrahydrofuran-hexane and determined for its structure by X-ray crystal structure analysis. See FIG. 4.

Example 9

Synthesis of Compound 8$^{AC-1}$

[Formula 57]

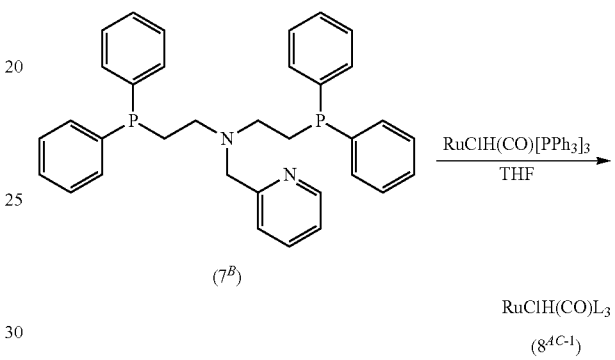

A 50 mL four-necked round-bottomed flask was equipped with a magnetic stirrer bar, a condenser tube and a thermometer, purged with nitrogen, and then charged sequentially with RuClH(CO)(PPh$_3$)$_3$ (537 mg, 0.563 mmoL, 1.0 equivalent), compound 7B obtained in Example 5 (300 mg, 0.563 mmoL) and toluene (20.0 mL). The resulting mixture was stirred under reflux for 6 hours. After cooling to 30° C., diethyl ether (10 mL) was added dropwise to obtain a dark brown suspension. The resulting suspension was stirred at 20° C. for 3 hours. After the reaction, the resulting dark brown suspension was subjected to suction filtration, and the crystals collected by filtration were then washed with diethyl ether and heated to dryness under reduced pressure to give the titled compound (8$^{AC-1}$) as a dark brown powder (200 mg).

Figure 3:
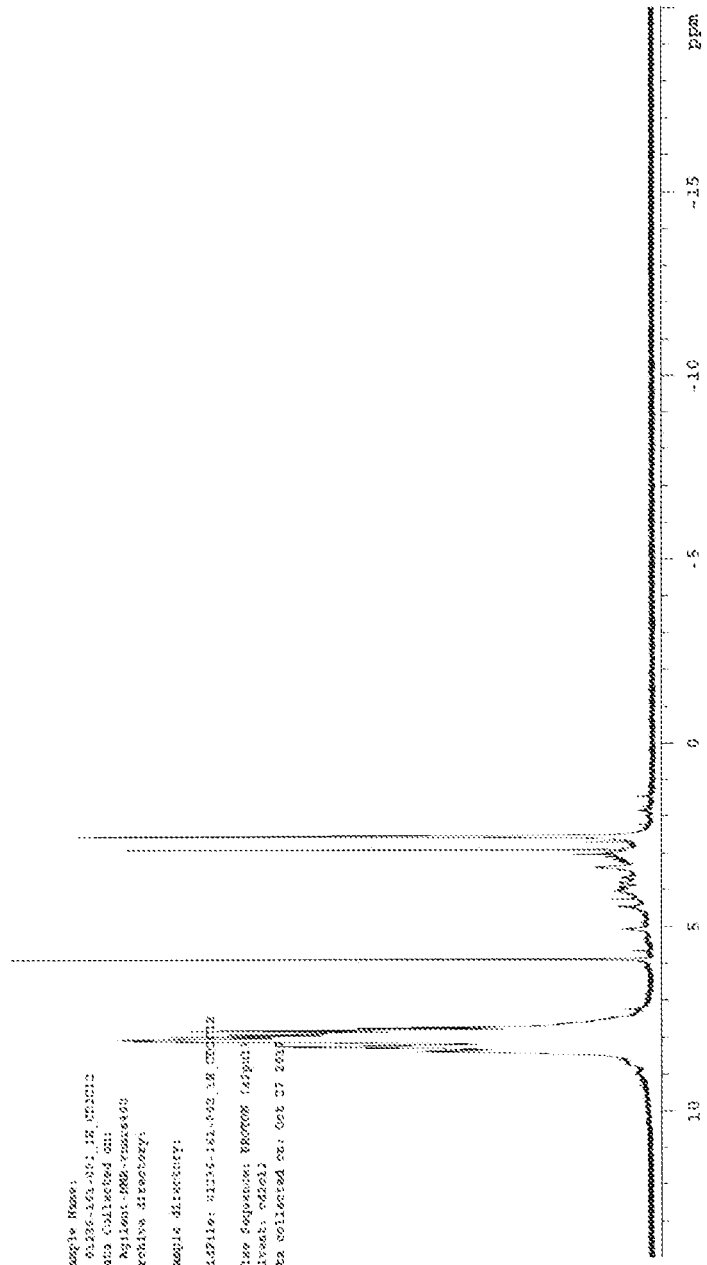
FIG. 3 shows a $^1$H-NMR spectrum of complex $8^{AC}$-1 obtained in Example 9.

Isolated yield: 63.5%.
$^1$H-NMR (400 MHz, CD$_2$Cl$_2$): see FIG. 3.
$^{31}$P-NMR (161 MHz, CD$_2$Cl$_2$): δ=27.7 (s, 1P)

Example 10

Synthesis of Compound $8^{Z-1}$

[Formula 58]

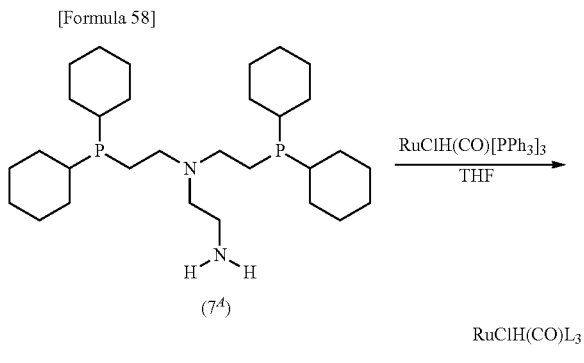

(7$^A$)

RuClH(CO)[PPh$_3$]$_3$ / THF →

RuClH(CO)L$_3$ ($8^{Z-1}$)

L$_3$ =

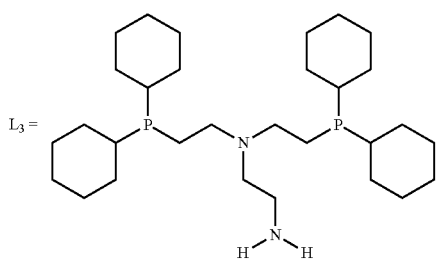

A 50 mL four-necked round-bottomed flask was equipped with a magnetic stirrer bar, a condenser tube and a thermometer, purged with nitrogen, and then charged sequentially with RuClH(CO)(PPh$_3$)$_3$ (197 mg, 0.206 mmoL, 1.0 equivalent), compound 7$^A$ obtained in the third step of Example 2 (100 mg, 0.206 mmoL) and tetrahydrofuran (THF) (4.0 mL). The resulting yellow suspension was stirred under reflux for 5 hours. After the reaction, the resulting yellow suspension was cooled to 5° C. and subjected to suction filtration. The crystals collected by filtration were then washed with tetrahydrofuran and heated to dryness under reduced pressure to give the titled compound ($8^{Z-1}$) as a white powder (20 mg). Isolated yield: 14.6%.

Example 11

Synthesis of Compound $8^{AK-1}$

[Formula 59]

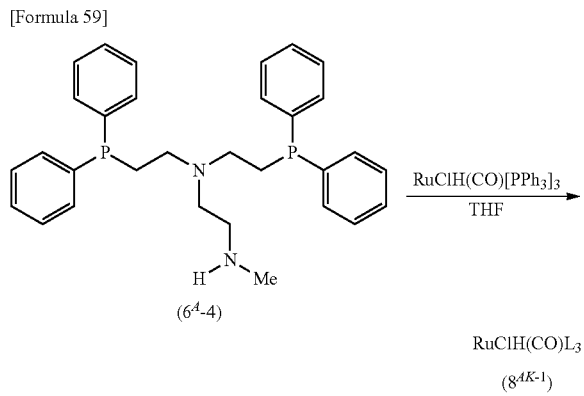

(6$^{A-4}$)

RuClH(CO)[PPh$_3$]$_3$ / THF →

RuClH(CO)L$_3$ ($8^{AK-1}$)

L$^3$ =

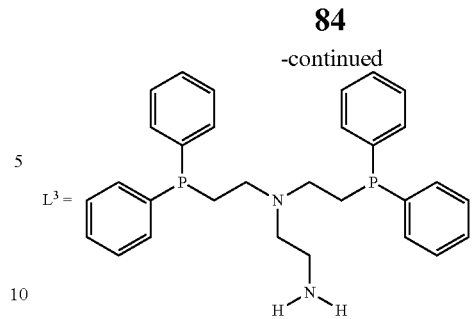

A 50 mL four-necked round-bottomed flask was equipped with a magnetic stirrer bar, a condenser tube and a thermometer, purged with nitrogen, and then charged sequentially with RuClH(CO)(PPh$_3$)$_3$ (1.53 g, 1.61 mmoL, 1.0 equivalent), compound 6$^{A-4}$ obtained in Example 4 (0.80 g, 1.61 mmoL, 1.0 equivalent) and tetrahydrofuran (THF) (20.0 mL). The resulting yellow suspension was stirred under reflux for 3 hours. After the reaction, the resulting yellow suspension was cooled to 5° C. and subjected to suction filtration. The crystals collected by filtration were then washed with tetrahydrofuran and heated to dryness under reduced pressure to give the titled compound ($8^{AK-1}$) as a white powder (466 mg). Isolated yield: 43.7%.

$^1$H-NMR (400 MHz, CD$_2$Cl$_2$): δ=7.87-7.66 (m, 8H), 7.45-7.34 (m, 12H), 3.73-3.70 (m, 1H), 3.41-3.28 (m, 4H), 3.07-3.02 (s, 3H), 2.94-2.91 (m, 2H), 2.79-2.63 (m, 4H), −14.5 to −14.6 (m, 1H).

$^{31}$P-NMR (161 MHz, CD$_2$Cl$_2$): δ=51.3 (s, 1P).

HRMS (FD, m/z) calculated for C$_{32}$H$_{37}$N$_2$OP$_2$Ru ([M−Cl]$^+$) 629.1425. found 629.1462.

Example 12

Synthesis of Compound $9^S$

[Formula 60]

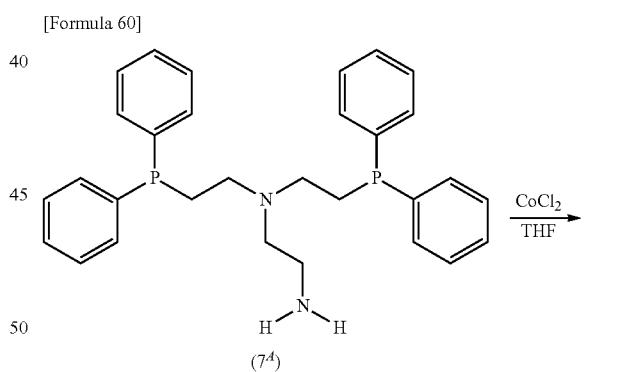

(7$^A$)

CoCl$_2$ / THF →

CoCl$_2$L$^3$ ($9^S$)

L$^3$ =

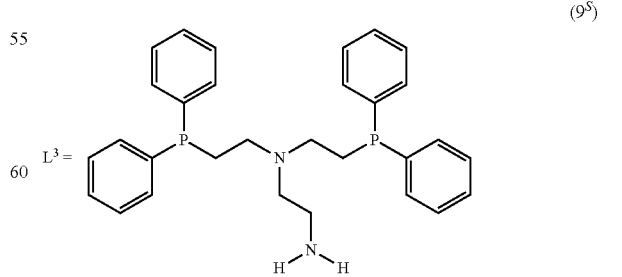

A 50 mL four-necked round-bottomed flask was equipped with a magnetic stirrer bar, a condenser tube and a thermometer, purged with nitrogen, and then charged sequentially with anhydrous $CoCl_2$ (100 mg, 1.54 mmoL, 1.0 equivalent), compound $7^A$ obtained in the third step of Example 2 (373 mg, 1.54 mmoL) and tetrahydrofuran (THF) (5.0 mL). The resulting dark blue solution was stirred under reflux for 6 hours. After the reaction, the resulting dark blue suspension was allowed to stand at 30° C. for 16 hours, the supernatant was removed with a syringe, and the remaining residue was washed with tetrahydrofuran and heated to dryness under reduced pressure to give the titled compound ($9^S$) as a dark blue solid (400 mg). Isolated yield: 84.5%.

Example 13

Synthesis of Compound $11^M$

[Formula 61]

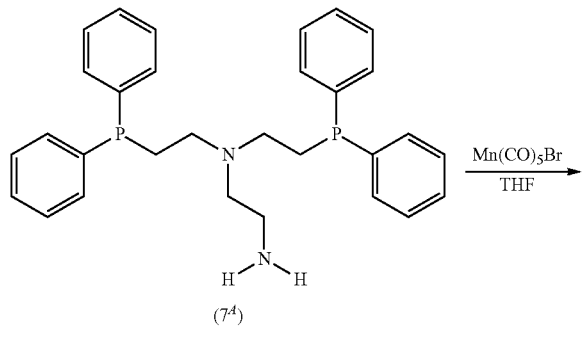

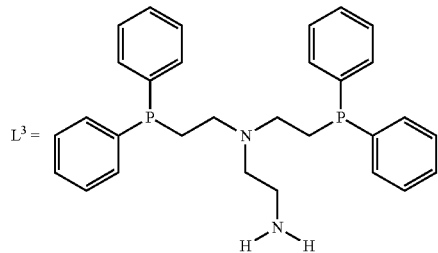

A 50 mL four-necked round-bottomed flask was equipped with a magnetic stirrer bar, a condenser tube and a thermometer, purged with nitrogen, and then charged sequentially with bromopentacarbonylmanganese ($Mn(CO)_5Br$) (200 mg, 0.73 mmoL, 1.0 equivalent), compound $7^A$ obtained in the third step of Example 2 (406 mg, 0.84 mmoL) and tetrahydrofuran (THF) (10.0 mL). The resulting yellow suspension was stirred under reflux for 3 hours. After the reaction, the resulting yellow suspension was evaporated to dryness under reduced pressure to give the titled compound ($11^M$) as an orange powder crude product (420 mg).

$^{31}$P-NMR (161 MHz, $CD_2Cl_2$): δ=76.1 (s, 1P).

HRMS (ESI, m/z) calculated for $C_{32}H_{34}MnN_2O_2P_2$ ([M-Br]$^+$) 595.1476. found 595.1471.

Example 14

Synthesis of Compound $18^E$

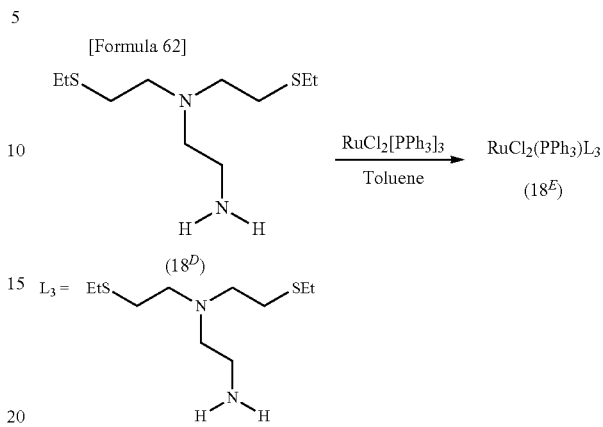

A 50 mL four-necked round-bottomed flask was equipped with a magnetic stirrer bar, a condenser tube and a thermometer, purged with nitrogen, and then charged sequentially with tris(triphenylphosphine)ruthenium(II) dichloride ($RuCl_2(PPh_3)_3$) (406 mg, 0.42 mmoL, 1.0 equivalent), compound 180 obtained in Example 6 (100 mg, 0.42 mmoL), toluene (1.4 mL) and tetrahydrofuran (THF) (0.5 mL). The resulting brown solution was stirred under reflux for 3 hours. After the reaction, the resulting brown suspension was cooled to 5° C. and subjected to suction filtration. The crystals collected by filtration were then washed with tetrahydrofuran and heated to dryness under reduced pressure to give the titled compound ($18^E$) as a brown powder (120 mg). Isolated yield: 42.3%.

HRMS (ESI, m/z) calculated for $C_{34}H_{34}N_2PRuS_2$ ([M]$^+$) 683.1019. found 683.1018.

Example 15

Synthesis of Compound $19^C$

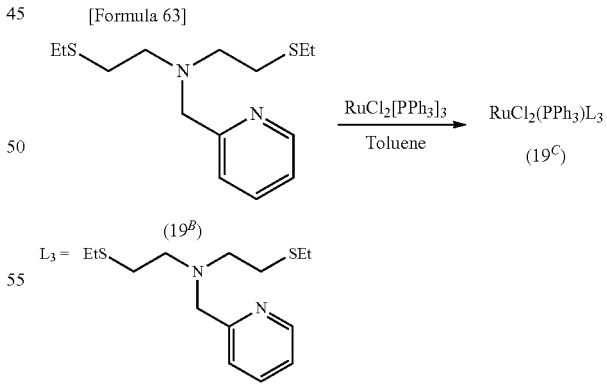

A 50 mL four-necked round-bottomed flask was equipped with a magnetic stirrer bar, a condenser tube and a thermometer, purged with nitrogen, and then charged sequentially with tris(triphenylphosphine)ruthenium(II) dichloride ($RuCl_2(PPh_3)_3$) (337 mg, 0.35 mmoL, 1.0 equivalent), compound $19^B$ obtained in Example 7 (100 mg, 0.35 mmoL) and toluene (1.2 mL). The resulting brown solution was stirred under reflux for 2 hours. After the reaction, the resulting brown suspension was cooled to 5° C. and subjected to suction filtration. The crystals collected by filtration were then washed with tetrahydrofuran and heated to dryness under reduced pressure to give the titled compound ($19^C$) as a brown powder (180 mg). Isolated yield: 71.5%.
HRMS (ESI, m/z) calculated for $C_{32}H_{39}ClN_2PRuS_2$ ($[M]^+$) 683.1019. found 683.1018.

Example 16

Synthesis of Benzyl Alcohol by Hydrogenation Reaction of Methyl Benzoate

A 300 mL stainless steel autoclave was charged with compound $8^Y$-1 obtained in Example 8 (6.8 mg, 0.02 mol %) and sodium methoxide (NaOMe) (270 mg, 5.0 mmol, 0.1 equivalents) and purged with nitrogen, and then charged sequentially with tetrahydrofuran (50.0 mL) and methyl benzoate (6.81 g, 50 mmol, 1.0 equivalent) and purged with hydrogen ($H_2$), and further pressurized with a $H_2$ gas to 5 MPa, followed by stirring at 100° C. for 6 hours to give the desired benzyl alcohol. Conversion: 91.2% (as measured by GC analysis).

Example 17

Synthesis of Benzyl Alcohol by Hydrogenation Reaction of Methyl Benzoate

A 300 mL stainless steel autoclave was charged with compound $8^Y$-1 obtained in Example 8 (3.4 mg, 0.01 mol %) and sodium methoxide (NaOMe) (270 mg, 5.0 mmol, 0.1 equivalents) and purged with nitrogen, and then charged sequentially with tetrahydrofuran (50.0 mL) and methyl benzoate (6.81 g, 50 mmol, 1.0 equivalent) and purged with hydrogen ($H_2$), and further pressurized with a $H_2$ gas to 5 MPa, followed by stirring at 100° C. for 6 hours to give the desired benzyl alcohol. Conversion: 87.5% (as measured by GC analysis).

Example 18

Synthesis of Benzyl Alcohol by Hydrogenation Reaction of Methyl Benzoate

A 50 mL stainless steel autoclave was charged with compound $8^{AC-1}$ obtained in Example 9 (7.0 mg, 0.2 mol %) and sodium methoxide (NaOMe) (54 mg, 1.0 mmol, 0.2 equivalents) and purged with nitrogen, and then charged sequentially with tetrahydrofuran (5.0 mL) and methyl benzoate (681 mg, 5.0 mmol, 1.0 equivalent) and purged with hydrogen ($H_2$), and further pressurized with a $H_2$ gas to 5 MPa, followed by stirring at 100° C. for 4 hours to give the desired benzyl alcohol. Conversion: 24.2% (as measured by GC analysis).

Example 19

Synthesis of Benzyl Alcohol by Hydrogenation Reaction of N,N-Dimethylbenzamide

A 50 mL stainless steel autoclave was charged with compound $8^Y$-1 obtained in Example 8 (3.3 mg, 0.2 mol %) and potassium tert-butoxide (KOtBu) (28 mg, 0.25 mmol, 0.1 equivalents) and purged with nitrogen, and then charged sequentially with tetrahydrofuran (2.5 mL) and N,N-dimethylbenzamide (373 mg, 2.5 mmol, 1.0 equivalent) and purged with hydrogen ($H_2$), and further pressurized with a $H_2$ gas to 5 MPa, followed by stirring at 100° C. for 6 hours to give the desired benzyl alcohol. Conversion: 45.4% (as measured by GC analysis).

Example 20

Synthesis of Benzyl Alcohol by Hydrogenation Reaction of N,N-Dimethylbenzamide

A 50 mL stainless steel autoclave was charged with compound $8^Y$-2 obtained in Example 8 (3.3 mg, 0.2 mol %) and potassium tert-butoxide ($KO^tBu$) (28 mg, 0.25 mmol, 0.1 equivalents) and purged with nitrogen, and then charged sequentially with tetrahydrofuran (2.5 mL) and N,N-dimethylbenzamide (373 mg, 2.5 mmol, 1.0 equivalent) and purged with hydrogen ($H_2$), and further pressurized with a $H_2$ gas to 5 MPa, followed by stirring at 100° C. for 6 hours to give the desired benzyl alcohol. Conversion: 76.0% (as measured by GC analysis).

Example 21

Synthesis of Benzyl Benzoate and Benzaldehyde by Dehydrogenation Reaction of Benzyl Alcohol A 30 mL three-necked round-bottomed flask was equipped with a magnetic stirrer bar, a condenser tube and a thermometer, purged with nitrogen, and then charged sequentially with compound $8^Y$-1 obtained in Example 8 (3.3 mg, 1.0 mol %), potassium tert-butoxide (KOtBu) (8.4 mg, 0.075 mmol, 0.15 equivalents) and toluene (1.0 mL). The resulting mixture was stirred under reflux for 8 hours to give the desired benzyl benzoate and benzaldehyde. Conversion: 91.5% and selectivity (benzyl benzoate): 98.4% (as measured by GC analysis).

Example 22

Synthesis of Benzyl Benzoate and Benzaldehyde by Dehydrogenation Reaction of Benzyl Alcohol A 30 mL three-necked round-bottomed flask was equipped with a magnetic stirrer bar, a condenser tube and a thermometer, purged with nitrogen, and then charged sequentially with compound $8^{AC-1}$ obtained in Example 9 (3.5 mg, 1.0 mol %), potassium tert-butoxide (KOtBu) (8.4 mg, 0.075 mmol, 0.15 equivalents) and toluene (1.0 mL). The resulting mixture was stirred under reflux for 8 hours to give the desired benzyl benzoate and benzaldehyde. Conversion: 29.9% and selectivity (benzyl benzoate): 86.2% (as measured by GC analysis).

Example 23

Synthesis of N-Benzylbenzamide and N-Benzylidenebenzylamine by Dehydrogenation Condensation Reaction Between Benzyl Alcohol and Benzylamine A 30 mL three-necked round-bottomed flask was equipped with a magnetic stirrer bar, a condenser tube and a thermometer, purged with nitrogen, and then charged sequentially with compound 8-1 obtained in Example 8 (3.3 mg, 1.0 mol %), potassium tert-butoxide ($KO^tBu$) (11.2 mg, 0.05 mmol, 0.1 equivalents), benzyl alcohol (54.1 mg, 0.5 mmoL, 1.0 equivalent), benzylamine (53.6 mg, 0.5 mmoL, 1.0 equivalent) and toluene (2.0 mL). The resulting mixture was stirred under reflux for 6 hours to give the desired N-benzylbenzamide and N-benzylidenebenzylamine. Conversion: 96.5% and selectivity (N-benzylidenebenzylamine): 72.6% (as measured by GC analysis).

Example 24

Synthesis of N-Benzylbenzamide and N-Benzylidenebenzylamine by Dehydrogenation Condensation Reaction Between Benzyl Alcohol and Benzylamine A 30 mL three-necked round-bottomed flask was equipped with a magnetic stirrer bar, a condenser tube and a thermometer, purged with nitrogen, and then charged sequentially with compound $8^Y$-2 obtained in Example 8 (3.3 mg, 1.0 mol %), potassium tert-butoxide (KO$^t$Bu) (11.2 mg, 0.05 mmol, 0.1 equivalents), benzyl alcohol (54.1 mg, 0.5 mmoL, 1.0 equivalent), benzylamine (53.6 mg, 0.5 mmoL, 1.0 equivalent) and toluene (2.0 mL). The resulting mixture was stirred under reflux for 6 hours to give the desired N-benzylbenzamide and N-benzylidenebenzylamine. Conversion: 96.0% and selectivity (N-benzylidenebenzylamine): 70.8% (as measured by GC analysis).

Example 25

Synthesis of Benzyl Alcohol by Hydrogenation Reaction of Benzyl Benzoate (Hydrogenation Reaction in Various Solvents Using Compound $8^Y$-1 or Compound $8^Y$-2 as a Catalyst)

A 100 mL stainless steel autoclave was charged with compound $8^Y$-1 or compound $8^Y$-2 obtained in Example 8 and potassium tert-butoxide (KOt-Bu) (112.2 mg, 1.0 mmol, 0.2 equivalents) and purged with nitrogen, and then charged sequentially with tetrahydrofuran (29.4 mL) and benzyl benzoate (1.06 g, 5 mmol, 1.0 equivalent) and purged with hydrogen (112), and further pressurized with a H$_2$ gas to 5 MPa, followed by stirring at 100° C. for 6 hours to give the desired benzyl alcohol. The conversion was determined under the conditions indicated in the table below (as measured by GC analysis).

TABLE 1

| Entry | Catalyst (moL %) | Solvent (0.17M) | KOt-Bu (equivalent) | Conversion (%) |
|---|---|---|---|---|
| 1 | $8^Y$-1 (0.02) | THF | 0.2 | 100 |
| 2 | $8^Y$-2 (0.02) | THF | 0.2 | 100 |
| 3 | $8^Y$-1 (0.05) | Toluene | 0.2 | 98.5 |
| 4 | $8^Y$-2 (0.05) | Toluene | 0.2 | 100 |
| 5 | $8^Y$-1 (0.05) | 1,4-Dioxane | 0.2 | 100 |
| 6 | $8^Y$-1 (0.1) | MeOH | 0.2 | 82.1 |
| 7 | $8^Y$-2 (0.1) | MeOH | 0.2 | 86.5 |
| 8 | $8^Y$-1 (0.1) | EtOH | 0.2 | 73.2 |
| 9 | $8^Y$-1 (0.1) | EtOH | 0.2 | 77.9 |
| 10 | $8^Y$-1 (0.1) | 2-Propanol | 0.2 | 99.5 |

Example 26

Synthesis of Benzyl Alcohol by Hydrogenation Reaction of Benzyl Benzoate

A 100 mL stainless steel autoclave was charged with compound $8^{Z-1}$ obtained in Example 10 (3.4 mg, 0.1 mol %) and potassium tert-butoxide (KOt-Bu) (112.2 mg, 1.0 mmol, 0.2 equivalents) and purged with nitrogen, and then charged sequentially with tetrahydrofuran (29.4 mL) and benzyl benzoate (1.06 g, 5.0 mmol, 1.0 equivalent) and purged with hydrogen (112), and further pressurized with a H$_2$ gas to 5 MPa, followed by stirring at 100° C. for 6 hours to give the desired benzyl alcohol. Conversion: 100% (as measured by GC analysis).

Example 27

Synthesis of Benzyl Alcohol by Hydrogenation Reaction of Benzyl Benzoate

A 100 mL stainless steel autoclave was charged with compound $8^{AK-1}$ obtained in Example 11 (3.3 mg, 0.1 mol %) and potassium tert-butoxide (KOt-Bu) (112.2 mg, 1.0 mmol, 0.2 equivalents) and purged with nitrogen, and then charged sequentially with tetrahydrofuran (29.4 mL) and benzyl benzoate (1.06 g, 5.0 mmol, 1.0 equivalent) and purged with hydrogen (H$_2$), and further pressurized with a H$_2$ gas to 5 MPa, followed by stirring at 100° C. for 6 hours to give the desired benzyl alcohol. Conversion: 100% (as measured by GC analysis).

Example 28

Synthesis of Benzyl Alcohol by Hydrogenation Reaction of Benzyl Benzoate

A 100 mL stainless steel autoclave was charged with compound 18' obtained in Example 14 (33.5 mg, 1.0 mol %) and potassium tert-butoxide (KOt-Bu) (112.2 mg, 1.0 mmol, 0.2 equivalents) and purged with nitrogen, and then charged sequentially with tetrahydrofuran (29.4 mL) and benzyl benzoate (1.06 g, 5.0 mmol, 1.0 equivalent) and purged with hydrogen (H$_2$), and further pressurized with a H$_2$ gas to 5 MPa, followed by stirring at 100° C. for 6 hours to give the desired benzyl alcohol. Conversion: 100% (as measured by GC analysis).

Example 29

Synthesis of 1-Phenylethyl Alcohol by Hydrogenation Reaction of Acetophenone

A 100 mL stainless steel autoclave was charged with compound $19^C$ obtained in Example 15 (35.9 mg, 1.0 mol %) and potassium tert-butoxide (KOt-Bu) (112.2 mg, 1.0 mmol, 0.2 equivalents) and purged with nitrogen, and then charged sequentially with tetrahydrofuran (29.4 mL) and benzyl benzoate (1.06 g, 5.0 mmol, 1.0 equivalent) and purged with hydrogen (H$_2$), and further pressurized with a H$_2$ gas to 5 MPa, followed by stirring at 100° C. for 6 hours to give the desired 1-phenylethyl alcohol. Conversion: 95.6% (as measured by GC analysis).

Example 30

Synthesis of Benzyl Alcohol by Hydrogenation Reaction of Benzyl Benzoate

A 50 mL stainless steel autoclave was charged with compound 11M obtained in Example 13 (3.2 mg, 1.0 mol %) and potassium tert-butoxide (KOt-Bu) (11.2 mg, 0.1 mmol, 0.2 equivalents) and purged with nitrogen, and then charged sequentially with tetrahydrofuran (2.8 mL) and benzyl benzoate (106 mg, 0.5 mmol, 1.0 equivalent) and purged with hydrogen (H$_2$), and further pressurized with a H$_2$ gas to 5 MPa, followed by stirring at 100° C. for 6 hours to give the desired benzyl alcohol. Conversion: 54.7% (as measured by GC analysis).

Example 31

Synthesis of N-Benzylbenzamide and N-Benzylidenebenzylamine by Dehydrogenation Condensation Reaction Between Benzyl Alcohol and Benzylamine A 30 mL three-necked round-bottomed flask was equipped with a magnetic stirrer bar, a condenser tube and a thermometer, purged with nitrogen, and then charged sequentially with compound $11^M$ obtained in Example 13 (3.2 mg, 1.0 mol %), potassium tert-butoxide (KO$^t$Bu) (11.2 mg, 0.05 mmol, 0.2 equivalents), benzyl alcohol (54.1 mg, 0.5 mmoL, 1.0 equivalent), benzylamine (53.6 mg, 0.5 moL, 1.0 equivalent) and toluene (2.0 mL). The resulting mixture was stirred under reflux for 6 hours to give the desired N-benzylbenzamide and N-benzylidenebenzylamine. Conversion: 21.6% and selectivity (N-benzylidenebenzylamine): 100% (as measured by GC analysis).

Example 32

Synthesis of Benzyl Alcohol by Hydrogenation Reaction of Benzyl Benzoate

A 50 mL stainless steel autoclave was charged with compound $9^S$ obtained in Example 12 (3.1 mg, 1.0 mol %) and potassium tert-butoxide (KOt-Bu) (22.4 mg, 0.2 mmol, 0.4 equivalents) and purged with nitrogen, and then charged sequentially with tetrahydrofuran (2.8 mL) and benzyl benzoate (106 mg, 0.5 mmol, 1.0 equivalent) and purged with hydrogen ($H_2$), and further pressurized with a 112 gas to 5 MPa, followed by stirring at 150° C. for 6 hours to give the desired benzyl alcohol. Conversion: 41.0% (as measured by GC analysis).

Example 33

Synthesis of Benzyl Alcohol by Hydrogenation Reaction of Dibenzyl Carbonate

A 50 mL stainless steel autoclave was charged with compound $8^Y$-1 obtained in Example 8 (9.8 mg, 3.0 mol %) and potassium tert-butoxide (KOt-Bu) (11.2 mg, 0.1 mmol, 0.2 equivalents) and purged with nitrogen, and then charged sequentially with tetrahydrofuran (2.8 mL) and dibenzyl carbonate (121 mg, 0.5 mmol, 1.0 equivalent) and purged with hydrogen ($H_2$), and further pressurized with a $H_2$ gas to 5 MPa, followed by stirring at 150° C. for 6 hours to give the desired benzyl alcohol. Conversion: 94.6% (as measured by GC analysis).

Example 34

Synthesis of Benzyl Alcohol by Hydrogenation Reaction of N-Benzyl Benzylcarbamate A 50 mL stainless steel autoclave was charged with compound $8^Y$-1 obtained in Example 8 (3.3 mg, 1.0 mol %) and potassium tert-butoxide (KOt-Bu) (11.2 mg, 0.1 mmol, 0.2 equivalents) and purged with nitrogen, and then charged sequentially with tetrahydrofuran (2.8 mL) and N-benzyl benzylcarbamate (121 mg, 0.5 mmol, 1.0 equivalent) and purged with hydrogen ($H_2$), and further pressurized with a $H_2$ gas to 5 MPa, followed by stirring at 150° C. for 6 hours to give the desired benzyl alcohol. Conversion: 55.7% (as measured by GC analysis).

Comparative Example 1

Synthesis of Benzyl Alcohol by Hydrogenation Reaction of Methyl Benzoate

[Formula 64]

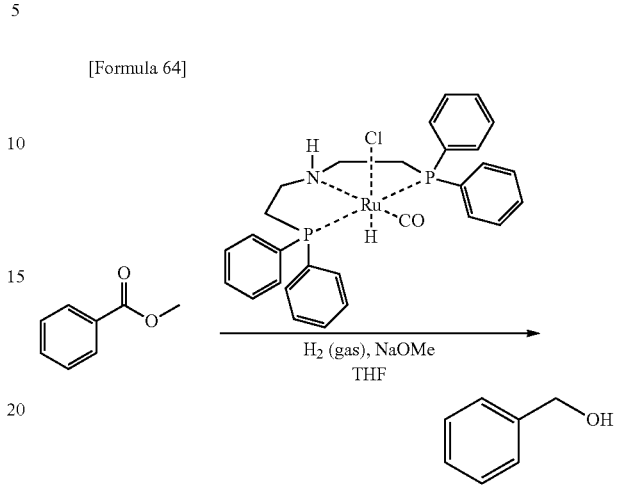

A 300 mL stainless steel autoclave was charged with the ruthenium complex appearing in Patent Literature 1 (6.1 mg, 0.02 mol %) and sodium methoxide (NaOMe) (270 mg, 5.0 mmol, 0.1 equivalents) and purged with nitrogen, and then charged sequentially with tetrahydrofuran (50.0 mL) and methyl benzoate (6.81 g, 50 mmol, 1.0 equivalent) and purged with hydrogen ($H_2$), and further pressurized with a $H_2$ gas to 5 MPa, followed by stirring at 100° C. for 6 hours to give the desired benzyl alcohol. Conversion: 33.3% (as measured by GC analysis).

Comparative Example 2

Synthesis of Benzyl Alcohol by Hydrogenation Reaction of N,N-Dimethylbenzamide

[Formula 65]

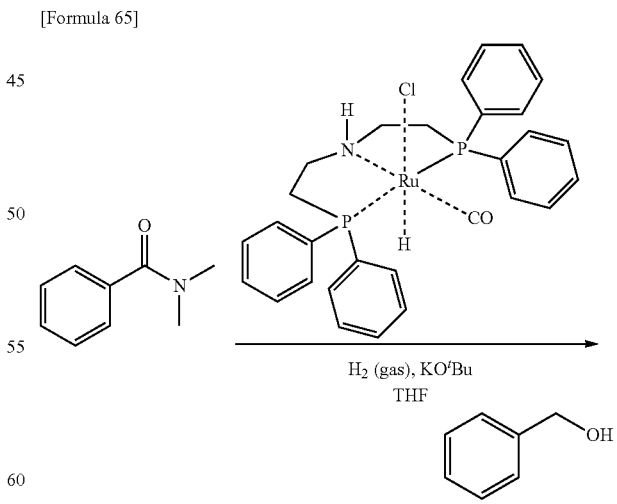

A 50 mL stainless steel autoclave was charged with the ruthenium complex appearing in Patent Literature 1 (3.0 mg, 0.2 mol %) and potassium tert-butoxide (KO$^t$Bu) (28 mg, 0.25 mmol, 0.1 equivalents) and purged with nitrogen, and then charged sequentially with tetrahydrofuran (2.5 mL) and N,N-dimethylbenzamide (373 mg, 2.5 mmol, 1.0 equivalent) and purged with hydrogen (H₂), and further pressurized with a H₂ gas to 5 MPa, followed by stirring at 100° C. for 6 hours to give the desired benzyl alcohol. Conversion: 0.2% (as measured by GC analysis).

Comparative Example 3

Synthesis of Benzyl Benzoate and Benzaldehyde by Dehydrogenation Reaction of Benzyl Alcohol

[Formula 66]

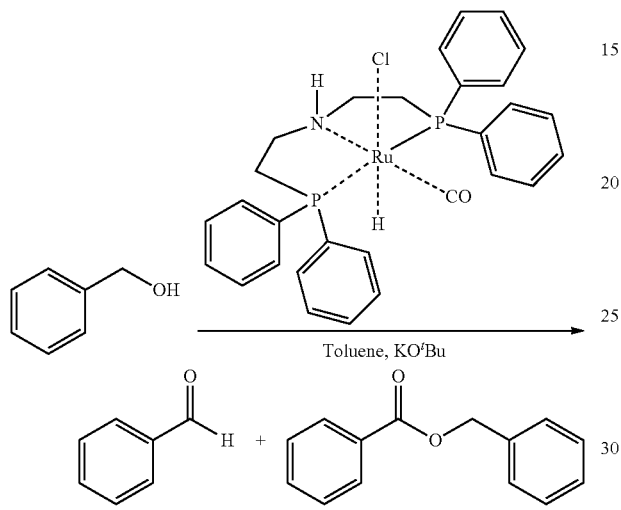

(Charge and Reaction) A 30 mL three-necked round-bottomed flask was equipped with a magnetic stirrer bar, a condenser tube and a thermometer, purged with nitrogen, and then charged sequentially with the ruthenium complex appearing in Patent Literature 1 (3.0 mg, 1.0 mol %), potassium tert-butoxide (KO$^t$Bu) (8.4 mg, 0.075 mmol, 0.15 equivalents) and toluene (1.0 mL). The resulting mixture was stirred under reflux for 8 hours to give the desired benzyl benzoate and benzaldehyde. Conversion: 48.7% and selectivity (benzyl benzoate): 93.8% (as measured by GC analysis).

Comparative Example 4

Synthesis of Benzyl Benzoate and Benzaldehyde by Dehydrogenation Reaction of Benzyl Alcohol

[Formula 67]

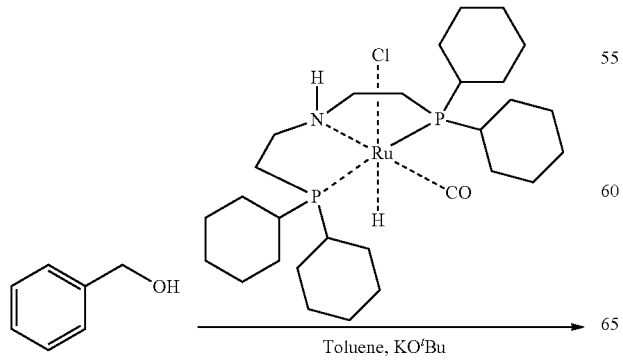

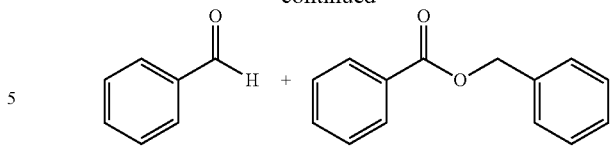

(Charge and Reaction) A 30 mL three-necked round-bottomed flask was equipped with a magnetic stirrer bar, a condenser tube and a thermometer, purged with nitrogen, and then charged sequentially with the ruthenium complex appearing in Patent Literature 1 whose substituents on the phosphorus atoms were replaced with cyclohexyl groups (3.2 mg, 1.0 mol %), potassium tert-butoxide (KO$^t$Bu) (8.4 mg, 0.075 mmol, 0.15 equivalents) and toluene (1.0 mL). The resulting mixture was stirred under reflux for 8 hours to give the desired benzyl benzoate and benzaldehyde. Conversion: 32.6% and selectivity (benzyl benzoate): 84.3% (as measured by GC analysis).

Comparative Example 5

Synthesis of Benzyl Benzoate and Benzaldehyde by Dehydrogenation Reaction of Benzyl Alcohol

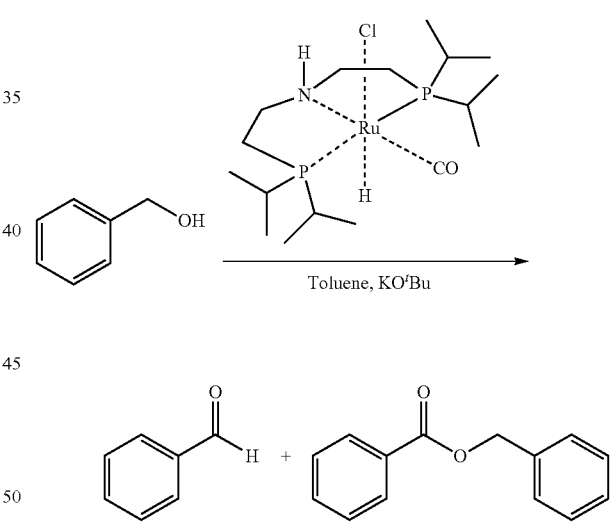

[Formula 68]

(Charge and Reaction) A 30 mL three-necked round-bottomed flask was equipped with a magnetic stirrer bar, a condenser tube and a thermometer, purged with nitrogen, and then charged sequentially with the ruthenium complex appearing in Patent Literature 1 whose substituents on the phosphorus atoms were replaced with isopropyl groups (2.4 mg, 1.0 mol %), potassium tert-butoxide (KO$^t$Bu) (8.4 mg, 0.075 mmol, 0.15 equivalents) and toluene (1.0 mL). The resulting mixture was stirred under reflux for 8 hours to give the desired benzyl benzoate and benzaldehyde. Conversion: 98.6% and selectivity (benzyl benzoate): 98.9% (as measured by GC analysis).

Comparative Example 6

Synthesis of Benzyl Benzoate and Benzaldehyde by Dehydrogenation Reaction of Benzyl Alcohol

[Formula 69]

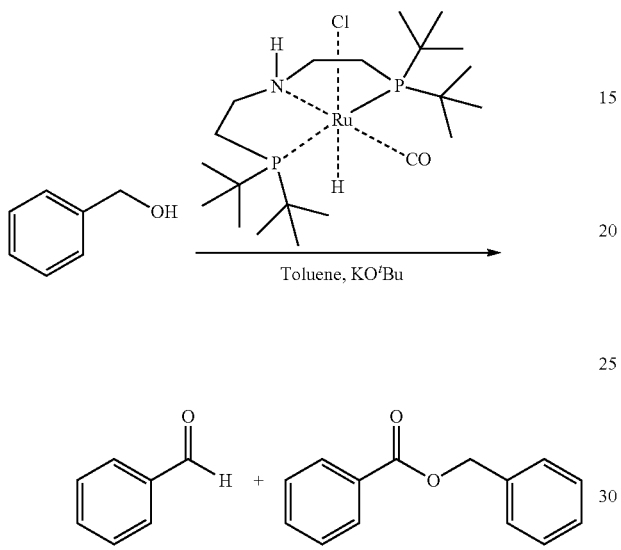

(Charge and Reaction) A 30 mL three-necked round-bottomed flask was equipped with a magnetic stirrer bar, a condenser tube and a thermometer, purged with nitrogen, and then charged sequentially with the ruthenium complex appearing in Patent Literature 1 whose substituents on the phosphorus atoms were replaced with t-butyl groups (2.6 mg, 1.0 mol %), potassium tert-butoxide (KO$^t$Bu) (8.4 mg, 0.075 mmol, 0.15 equivalents) and toluene (1.0 mL). The resulting mixture was stirred under reflux for 8 hours to give the desired benzyl benzoate and benzaldehyde. Conversion: 23.9% and selectivity (benzyl benzoate): 12.4% (as measured by GC analysis).

INDUSTRIAL APPLICABILITY

The present invention provides a novel transition metal complex having a tetradentate ligand which can be easily prepared from readily available inorganic compounds. The novel transition metal complex of the present invention catalyzes hydrogenation reduction of ketones, esters and amides in the presence of a hydrogen donor, and also catalyzes oxidation reaction of alcohols, and alkylation reaction of amines using alcohols as carbon sources. The transition metal complex of the present invention not only shows high catalytic activity even under relatively mild reaction conditions, but is also easy to handle, and is therefore suitable for industrial use. Thus, the transition metal complex of the present invention, and reactions using the same are useful in the field of organic industrial chemistry.

The invention claimed is:

1. A ruthenium complex having a ligand having one of the following formulas:

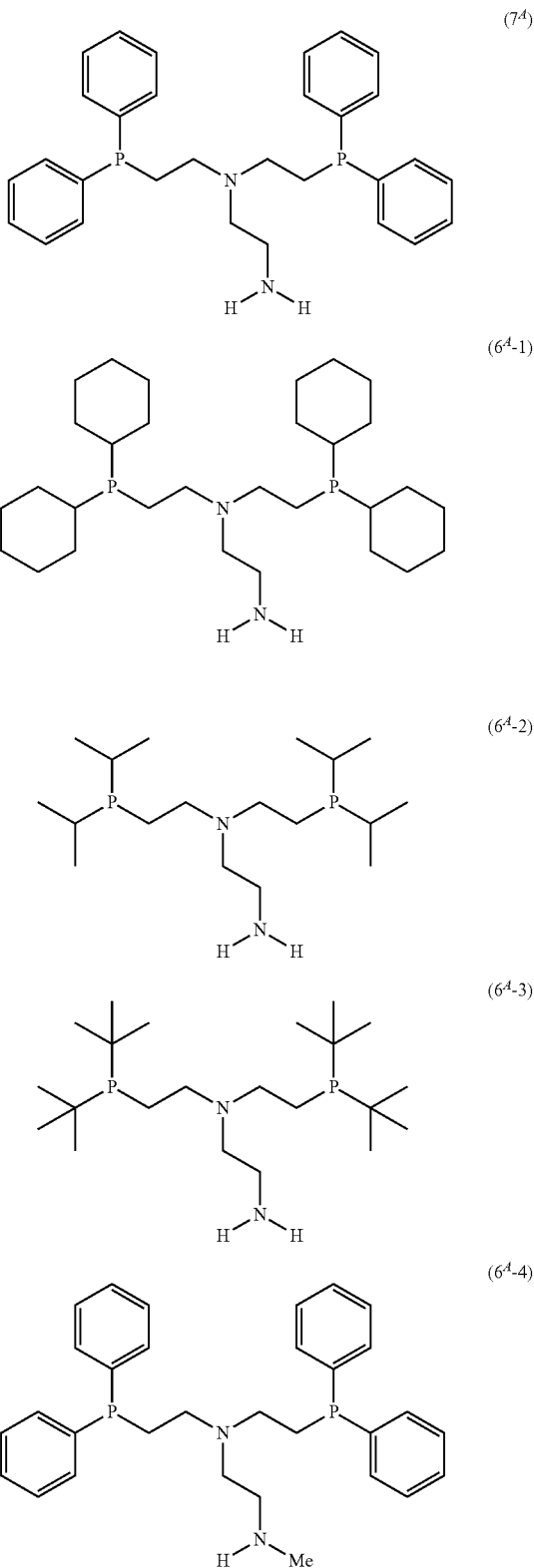

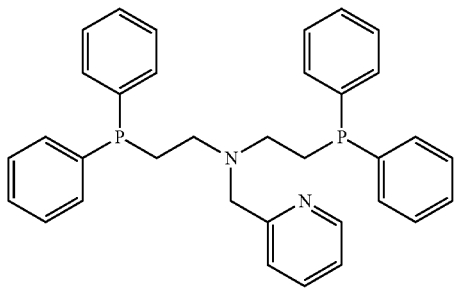

(7^B)

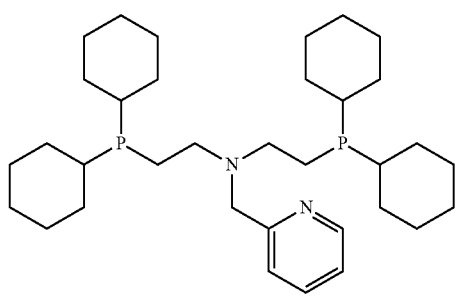

(6^B-1)

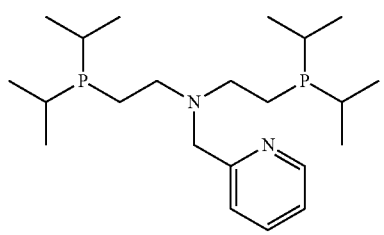

(6^B-2)

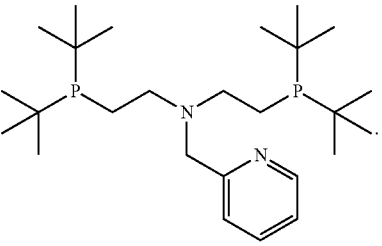

(6^B-3)

2. The ruthenium complex of claim 1, wherein the ligand has the formula (7^A).

3. The ruthenium complex of claim 1, wherein the ligand has the formula (6^A-1).

4. The ruthenium complex of claim 1, wherein the ligand has the formula (6^A-2).

5. The ruthenium complex of claim 1, wherein the ligand has the formula (6^A-3).

6. The ruthenium complex of claim 1, wherein the ligand has the formula (6^A-4).

7. The ruthenium complex of claim 1, wherein the ligand has the formula (7^B).

8. The ruthenium complex of claim 1, wherein the ligand has the formula (6^B-1).

9. The ruthenium complex of claim 1, wherein the ligand has the formula (6^B-2).

10. The ruthenium complex of claim 1, wherein the ligand has the formula (6^B-3).

11. A method for manufacturing alcohols, aldehydes or hemiacetals, the method comprising hydrogenation reduction of esters in the presence of the ruthenium complex according to claim 1.

12. A method for manufacturing alcohols, aldehydes, hemiaminals or amines, the method comprising hydrogenation reduction of amides in the presence of the ruthenium complex according to claim 1.

13. A method for manufacturing carbonyl compounds, the method comprising dehydrogenation of alcohols, hemiacetals or hemiaminals in the presence of the ruthenium complex according to claim 1.

14. A method for manufacturing alkylamines, the method comprising dehydration condensation between alcohols and amines in the presence of the ruthenium complex according to claim 1.

* * * * *